US007097995B2

(12) United States Patent
Jiang et al.

(10) Patent No.: US 7,097,995 B2
(45) Date of Patent: Aug. 29, 2006

(54) CHEMILUMINESCENT ACRIDINIUM COMPOUNDS AND ANALOGUES THEREOF AS SUBSTRATES OF HYDROLYTIC ENZYMES

(75) Inventors: Qingping Jiang, Northborough, MA (US); Anand Natrajan, Manchester, NH (US); David J. Sharpe, Foxboro, MA (US); Wen-Jee Wong, Weston, MA (US); Say-Jong Law, Westwood, MA (US)

(73) Assignee: Bayer Corp., Tarrytown, NY (US)

( * ) Notice: Subject to any disclaimer, the term of this patent is extended or adjusted under 35 U.S.C. 154(b) by 105 days.

(21) Appl. No.: 10/928,300

(22) Filed: Aug. 27, 2004

(65) Prior Publication Data
US 2005/0032147 A1 Feb. 10, 2005

Related U.S. Application Data

(63) Continuation of application No. 09/626,566, filed on Jul. 27, 2000, now Pat. No. 6,783,948.

(60) Provisional application No. 60/146,648, filed on Jul. 30, 1999.

(51) Int. Cl.
C12Q 1/34 (2006.01)
(52) U.S. Cl. .......................... 435/18; 546/102
(58) Field of Classification Search .................. None
See application file for complete search history.

(56) References Cited

U.S. PATENT DOCUMENTS

| | | | | |
|---|---|---|---|---|
| 4,745,181 A | 5/1988 | Law et al. | ................... | 530/387 |
| 4,810,636 A | 3/1989 | Corey | ................... | 435/14 |
| 4,927,769 A | 5/1990 | Chang et al. | ................... | 436/518 |
| 4,931,223 A | 6/1990 | Bronstein et al. | ................... | 252/700 |
| 4,959,182 A | 9/1990 | Schaap | ................... | 252/700 |
| 5,004,565 A | 4/1991 | Schaap | ................... | 252/700 |
| 5,013,827 A | 5/1991 | Schaap | ................... | 536/17.3 |
| 5,112,960 A | 5/1992 | Bronstein et al. | ................... | 536/18.1 |
| 5,145,772 A | 9/1992 | Voyta et al. | ................... | 435/4 |
| 5,306,621 A | 4/1994 | Kricka | ................... | 435/7.91 |
| 5,326,882 A | 7/1994 | Bronstein et al. | ................... | 549/16 |
| 5,393,469 A | 2/1995 | Akhavan-Tafti | ................... | 252/700 |
| 5,451,347 A | 9/1995 | Akhavan-Tafti et al. | ................... | 252/700 |
| 5,468,646 A | 11/1995 | Mattingly et al. | ................... | 436/501 |
| 5,484,556 A | 1/1996 | Akhavan-Tafti et al. | ................... | 252/700 |
| 5,589,328 A | 12/1996 | Mahant | ................... | 435/4 |
| 5,656,426 A | 8/1997 | Law et al. | ................... | 435/6 |
| 5,721,370 A | 2/1998 | Akhavan-Tafti et al. | ................... | 549/218 |
| 5,772,926 A | 6/1998 | Akhavan-Tafti | ................... | 252/700 |
| 5,869,699 A | 2/1999 | Bronstein et al. | ................... | 549/219 |
| 5,892,064 A | 4/1999 | Schaap et al. | ................... | 549/510 |
| 5,936,101 A | 8/1999 | Akhavan-Tafti et al. | ................... | 549/332 |
| 5,965,736 A | 10/1999 | Akhavan-Tafti | ................... | 548/110 |
| 6,285,127 B1 * | 9/2001 | Khan et al. | ................... | 313/582 |
| 6,355,803 B1 * | 3/2002 | Natrajan et al. | ................... | 546/102 |
| 6,783,948 B1 * | 8/2004 | Jiang et al. | ................... | 435/18 |
| 2003/0219844 A1 * | 11/2003 | Waldrop et al. | ........... | 435/7.92 |
| 2004/0063147 A1 * | 4/2004 | Natrajan et al. | ............. | 435/7.1 |
| 2005/0255528 A1 * | 11/2005 | Evangelista et al. | ......... | 435/7.1 |

FOREIGN PATENT DOCUMENTS

| | | |
|---|---|---|
| EP | 0 401 001 A2 | 12/1990 |
| EP | 0 516 948 A1 | 12/1992 |
| EP | 0 943 618 A2 | 3/1999 |
| WO | WO 90/07511 | 7/1990 |
| WO | WO 94/02486 | 2/1994 |
| WO | WO 94/10258 | 5/1994 |
| WO | WO 96/07911 | 3/1996 |
| WO | WO 97/26245 | 7/1997 |
| WO | WO 98/56765 | 12/1998 |
| WO | WO 99/09012 | 2/1999 |
| WO | WO 00/06164 | 2/2000 |
| WO | WO 00/09487 | 2/2000 |

OTHER PUBLICATIONS

Kazumi Sasamoto et al., *A Chemiluminogenic Substrate for N-Acetyl-β-D-glucosaminidase, o-Aminophthalylhydrazido-N-acetyl-β-D-glucosaminide*, Chem. Pharm. Bull. 38(5) 1323-1325 (1990).

(Continued)

*Primary Examiner*—Ralph Gitomer
(74) *Attorney, Agent, or Firm*—Rupa Sen; Weingarten, Schurgin, Gagnebin & Lebovici LLP

(57) ABSTRACT

A chemiluminescent substrate of a hydrolytic enzyme having the following general Formula I is disclosed, as follows:

Lumi-M-P Formula I where "Lumi" is a chemiluminescent moiety capable of producing light (a) by itself, (b) with MP attached and (c) with M attached. Examples of Lumi include chemiluminescent acridinium compounds, benzacridinium compounds, quinolinium compounds, isoquinolinium compounds, phenanthridinium compounds, and lucigenin compounds, spiroacridan compounds, luminol compounds and isoluminol compounds. M is a multivalent heteroatom having at least one lone pair of electrons selected from oxygen, nitrogen and sulfur, directly attached to the light emitting moiety of Lumi at one end and to P at the other end. P is a group that can be readily removed by hydrolytic enzymes. An enzymatic reaction utilizing the above compound is the following:

Reaction A

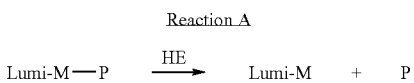

where HE is a hydrolytic enzyme. Lumi-M is a chemiluminescent product having physical and/or chemical properties different from those of Lumi-M-P.

12 Claims, 32 Drawing Sheets

OTHER PUBLICATIONS

Kazumi Sasamoto et al., *A New Chemiluminogenic Substrate for N-β-D-glucosaminidase, 4'-(6'-Diethylaminobenzofuranyl)phthalylhydrazido-N-acetyl-β-D-glucosaminide*, Chem. Pharm Bull. 39(2) 411-416 (1991).

T. Kinkel et al., *Synthesis and Properties of New Luminescent Acridinium-9-carboxylic Acid Derivatives and their Application in Luminescence Immunoasays (LIA)*, Jour. of Bioluminescence and Chemiluminescence, vol. 4 136-139 (1989).

Wolf Dieter Engel et al., *CEDIA * in vitro diagnostics with a novel homogeneous immunoassay technique*, Jour. Of Immunological Methods, 150 99-102 (1992).

Larry J. Kricka, *Ultrasensitive Immunoassay Techniques*, Clin. Biochem., vol. 26, 325-331 (1993).

David Wild et al., *Components, Ch. 2 in Wild, The Immonoassay Handbook* , (1994), Stockton Press, 4 W. 34th St., NY, NY, 10010, USA.

A. Paul Schaap et al., *Chemical and Enzymatic Triggering of 1,2-Dioxetanes.2: Fluoride-Induced Chemiluminescence from Tert-Butyldimethylsilyloxy-Substituted Dioxetanes*, (1987), Tetrahedron Letters vol. 28, No. 11, 1155-1158.

Brian R. Clark et al., *Chapter 8 Enzyme-Linked Immunosorbent Assay (ELISA): Theoretical and Practical Aspects*, 167-247 in Maggio, (1980) CRC Press, Inc., 2000 N.W. 24th St., Boca Raton, FL 33431.

Renault, Jean, et al., *"Héterocycles á fonction quinone. I. Acridinediones-1,4 á action antitumorale potentielle"*; Eur. Jour. of Medicinal Chemistry—Chimica Therapeutica, vol. 16, No. 1, Jan.-Feb., 1981-16, pp. 24-34.

* cited by examiner

CHEMILUMINESCENT ACRIDINIUM COMPOUNDS AND ANALOGUES THEREOF AS SUBSTRATES OF HYDROLYTIC ENZYMES

CROSS REFERENCE TO RELATED APPLICATIONS

This application is a continuation of U.S. patent application Ser. No. 09/626,566 filed on Jul. 27, 2000 now U.S. Pat. No. 6,783,948 and further claims priority of U.S. Provisional Application No. 60/146,648, filed Jul. 30, 1999, both of which are hereby incorporated herein by reference.

STATEMENT REGARDING FEDERALLY SPONSORED RESEARCH OR DEVELOPMENT

N/A

FIELD OF THE INVENTION

This invention relates to novel chemiluminescent compounds that are substrates of hydrolytic enzymes, the chemiluminescent products of which have distinctly different light emission characteristics (i.e., emission wavelength, kinetics, or quantum yield). This invention also relates to a light-releasing reagent composition that reacts preferentially with the chemiluminescent substrate or with the chemiluminescent product in the mixture of the two, to generate a discernible signal that can be quantified. This invention further relates to detection methods comprising a novel acridinium-based chemiluminescent substrate, a hydrolytic enzyme and a signal-releasing reagent. This invention furthermore relates to detection devices in conjunction with the use of novel chemiluminescent substrates and hydrolytic enzymes, which include a red-sensitive photomultiplier tube or a charge-coupled device, and a light-filtering device to maximize the detection of chemiluminescent product signal. Further, this invention relates to the use of these novel chemiluminescent substrates in assays to detect, quantitatively or qualitatively, a hydrolytic enzyme of interest that is present either as a label or as a marker of a biological sample. Finally, this invention relates to the process and intermediates for the preparation of these novel chemiluminescent substrates.

BACKGROUND OF THE INVENTION

The detection of hydrolytic enzymes has been extensively used in diagnostic assays ranging from immunoassays, nucleic acid assays, receptor assays, and other assays, primarily due to their high sensitivity and non-radioactivity. The hydrolytic enzymes include phosphatases, glycosidases, peptidases, proteases, and esterases. By far, most commonly used are phosphatases and glycosidases. For instance, alkaline phosphatase has been extensively used as a label in various enzyme-linked immunosorbent assays (ELISAs) due to its high turn-over rate, excellent thermal stability and ease of use. Many glycosidases, such as β-galactosidase and β-glucuronidase, have also been used in ELISA due to their very high selectivity for the hydrolysis of their preferred substrates. On the other hand, some hydrolytic enzymes play important functions by themselves in biological processes of the human body and microorganisms. Therefore, direct detection of these markers is another important aspect of diagnostics.

In connection with the detection of hydrolytic enzymes, there are three types of substrates: chromogenic, fluorogenic and chemiluminescent substrates. Among them, chemiluminescent substrates offer the best enzyme detection sensitivity due to the intrinsic advantages of higher detectability of chemiluminescent product, or lower substrate and instrumental backgrounds, and less interference from biological samples. Therefore, there has been a steady trend towards developing chemiluminescent substrates and applying them in a variety of diagnostics.

Stable Dioxetanes

One class of widely used chemiluminescent substrates for hydrolytic enzymes are stable dioxetanes (Bronstein et al., U.S. Pat. Nos. 4,931,223, 5,112,960, 5,145,772 and 5,326,882; Schaap et al., U.S. Pat. Nos. 5,892,064, 4,959,182 and 5,004,565; and Akhavan-Tafti et al., U.S. Pat. No. 5,721,370). Here, the thermally stable protective group on the phenolic moiety of the dioxetane substrates is cleaved by a hydrolytic enzyme of interest, such as alkaline phosphatase (AP) or β-galactosidase, depending on whether the protective group is a phosphoryl or β-D-galactopyranosidyl group. The newly generated dioxetane phenoxide anion undergoes auto-decomposition to a methoxycarbonylphenoxide in an electronically excited state. The latter then emits light at $\lambda$max~470 nm.

In an aqueous environment where virtually all biological assays are performed, the decomposition of the dioxetanes produces chemiluminescence in a very low quantum yield, typically about 0.01%, and a slow kinetics with $t_{1/2}$ 1~10 minutes. This is quite different from the decomposition of the dioxetanes in an organic environment. For instance, the dioxetane having the phenol moiety protected by an acetyl group or a silyl group, upon treatment with a base or fluoride, exhibits quantum yield up to 25% in DMSO and 9.4% in acetonitrile, respectively, and $t_{1/2}$ is about 5 sec. at 25° C. Schaap, et al., *Tetrahedron Letters*, 28(11), 1155, (1987) and WO 90/07511 A.

Voyta et al., (U.S. Pat. No. 5,145,772) disclosed a method of intermolecular enhancement of quantum yield of the dioxetane products using polymeric ammonium salts, which provide a hydrophobic environment for the phenoxide produced by the enzyme.

Akhavan-Tafti et al., reported methods of intermolecular enhancement of quantum yield of the dioxetane products using polymeric phosphonium salts (U.S. Pat. No. 5,393,469) and dicationic surfactants (U.S. Pat. Nos. 5,451,347 and 5,484,556).

Schaap et al., (U.S. Pat. Nos. 4,959,182 and 5,004,565) disclosed another method for increasing quantum yield of the dioxetane products using fluorescent co-surfactants as energy acceptors. The resonance energy embodied in the excited phenoxide produced by the enzyme is effectively transferred to the fluorescent co-surfactants. Instead of emitting light at $\lambda$max 470 nm characteristic of the dioxetane, this system emits light at $\lambda$max 530 nm as a result of energy transfer to the highly efficient fluorophore, fluorescein.

Another approach for improving quantum yield of the dioxetanes, disclosed by Schaap et al., (U.S. Pat. No. 5,013,827), is to covalently attach a fluorophore having high quantum yield to the light emitting phenoxide moiety. The resonance energy from the excited phenoxide is intramolecularly transferred to the attached fluorophore. The latter in turn emits light at its own wavelength. It is claimed that such dioxetane-fluorophore conjugates exhibit quantum yield as high as 2%.

Wang et al., (WO 94/10258) unveiled a class of electron-rich, aryl-substituted dioxetane compounds in which the aryl group is poly-substituted with a suitable electron-donating group so that intense luminescence is observed.

Akhavan-Tafti et al., (U.S. Pat. No. 5,721,370) provided a group of stable chemiluminescent dioxetane compounds with improved water solubility and storage stability. The compounds are substituted with two or more hydrophilic groups disposed on the dioxetane structure and an additional fluorine atom or lower alkyl group.

Schaap et al., (U.S. Pat. No. 5,892,064) disclosed a class of chemiluminescent dioxetane compounds substituted on the dioxetane ring with two nonspirofused alkyl groups.

Urdea at al. (EP Application 0401001 A2) described another sub-class of dioxetane compounds that can be triggered by sequential treatment with two different activating enzymes to generate light. The system rests on the principle that the dioxetane substrates have two protecting groups that can be removed sequentially by different processes to produce an excited phenoxide, and the removal of the first protecting group is triggered by the enzyme used as a label in the assay.

Luminol Substrates

Sasamoto at al., *Chem. Pharm. Bull.*, 38(5), 1323 (1990) and *Chem. Pharm. Bull.*, 39(2), 411 (1991), reported that o-aminophthalhydrazide-N-acetyl-β-D-glucosaminide (Luminol-NAG) and 4'-(6'-diethylaminobenzofuranyl)-phthalhydrazide-N-acetyl-β-D-glucosaminide, both being the non-luminescent forms of luminol, are substrates of N-acetyl-β-D-glucosaminidase. Upon the action of the enzyme on these substrates, luminol or luminol derivative is generated, which then can be detected by triggering with 0.1% hydrogen peroxide and a peroxidase (POD) or Fe(III)-TCPP complex catalyst to release a chemiluminescent signal.

Enzyme-Modulated Protected Enhancer and Anti-Enhancer

Kricka (U.S. Pat. No. 5,306,621) disclosed that light intensity of certain peroxidase-catalyzed chemiluminescent reactions can be modulated by AP that acts on a pro-enhancer or a pro-anti-enhancer. For example, the intensity of a chemiluminescent reaction containing luminol, horseradish peroxide and hydrogen peroxide can be enhanced by an enhancer (4-iodophenol) liberated by the enzymatic action of AP on a pro-enhancer (4-iodophenol phosphate), thus enabling AP to be assayed. Alternatively, in the same above reaction where additional enhancer (4-iodophenol) is present, the light intensity can be decreased by an anti-enhancer (4-nitrophenol) generated by the enzymatic action of AP on a pro-anti-enhancer (4-nitrophenol phosphate). In the latter format, the presence of AP can be assayed by measuring the reduction in the light intensity.

Similar to the above, an assay using enzyme-triggerable protected enhancer for quantitation of hydrolytic enzymes was also unveiled by Akhanvan-Tafti in EP Application 0516948 A1.

Akhanvan-Tafti et al., (WO 96/07911) disclosed another method of detecting hydrolytic enzymes based on the principle of the protected enhancer, where the light emitting species is generated from the oxidation of acridan by peroxidase and peroxide.

Acridene Enol Phosphate

Akhanvan-Tafti et al., (U.S. Pat. No. 5,772,926 and WO 97/26245) disclosed a class of heterocyclic, enol phosphate compounds represented by the non-luminescent acridene enol phosphate. Upon the reaction with a phosphatase enzyme, acridene enol phosphate is converted to the dephosphoryl enolate, which reacts with molecular oxygen to produce light (see scheme below). It was also disclosed that the light output was greatly enhanced by the addition of a cationic aromatic compound to the assay system.

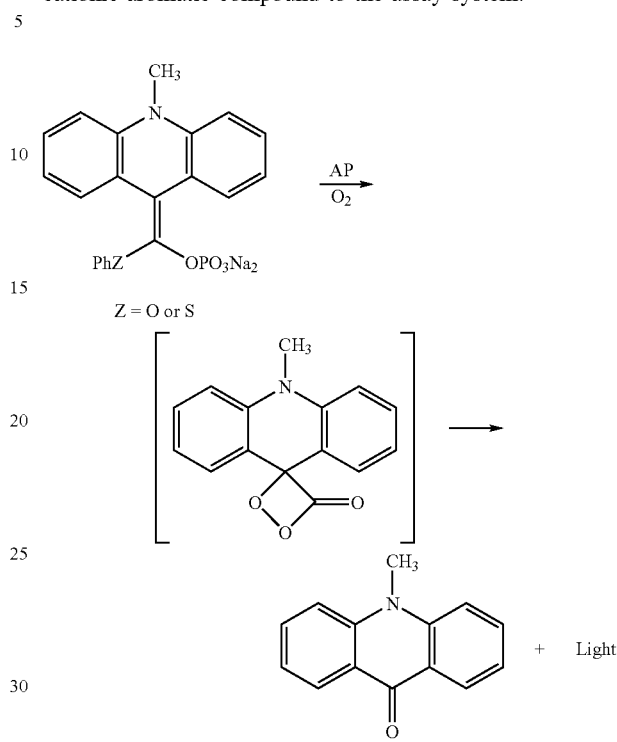

Other Chemiluminescent Substrates for Hydrolytic Enzymes

Vijay (U.S. Pat. No. 5,589,328) disclosed chemiluminescent assays that detect or quantify hydrolytic enzymes, such as alkaline phosphatase, that catalyze the hydrolysis of indoxyl esters. The assay includes the steps of reacting a test sample with an indoxyl ester and then immediately or within a short time (typically less than about 15 minutes) measuring the resulting chemiluminescence. The resulting chemiluminescence may be amplified by adding a chemiluminescent enhancing reagent.

Among the above chemiluminescent hydrolytic enzyme methods, the dioxetane system appears to be the most sensitive detection system and therefore has been increasingly used in various assays. Despite its widespread use, this system has an inherent drawback in that background chemiluminescence in the absence of enzyme is observed due to slow thermal decomposition and non-enzymatic hydrolysis of the dioxetane. Another intrinsic disadvantage is that the phenoxide, once generated by enzymatic reaction, is extremely unstable and readily undergoes decomposition to release light. In this sense, the phenoxide, the light emitting species, is never "accumulated" during the enzymatic reaction. Therefore, it is one of the major goals of this invention to provide new chemiluminescent substrates whose derived chemiluminescent products have distinguishable emission profiles and whose total signal can be accumulated during the enzymatic reaction, thereby providing an alternative and sensitive detection method for hydrolytic enzymes.

BRIEF SUMMARY OF THE INVENTION

It is an object of this invention to provide chemiluminescent compounds that are substrates of hydrolytic enzymes.

Said chemiluminescent substrates upon treatment with a hydrolytic enzyme convert to the corresponding chemiluminescent products that have distinctly different light emission characteristics.

It is another object of this invention to provide acridinium-based chemiluminescent compounds that are substrates of hydrolytic enzymes. Said chemiluminescent substrates contain a phenolic moiety or enol moiety in the molecule that is masked by a group, which is thermally and hydrolytically stable. Upon treatment with a hydrolytic enzyme, said chemiluminescent substrates convert to the corresponding acridinium-based chemiluminescent products that have distinctly different light emission characteristics.

It is also an object of this invention that said chemiluminescent substrates and products have distinctly different light emission characteristics, thereby allowing the separation or distinction of the signal of the substrate from the signal of the product, or vice versa when both substrate and product are present in the same test vessel.

It is another object of this invention that said chemiluminescent products generated by hydrolytic enzymes have emission maxima different from those of their corresponding chemiluminescent substrates.

It is another object of this invention that said chemiluminescent products generated by hydrolytic enzymes have quantum yields different from those of their corresponding chemiluminescent substrates.

It is another object of this invention that said chemiluminescent products generated by hydrolytic enzymes have light-emitting kinetics different from those of their corresponding chemiluminescent substrates.

It is another object of this invention that said chemiluminescent products generated by hydrolytic enzymes have physical and chemical properties different from those of their corresponding chemiluminescent substrates. Said physical and chemical properties include, but are not limited to, the fundamental net charge distribution, dipole moment, π-bond orders, free energy, or the apparent hydrophobicity/hydrophilicity, solubility, affinity and other properties that are otherwise apparent to those who are skilled in the art.

It is another object of this invention that said chemiluminescent substrates are structurally manipulated such that the distinction of the light emission characteristics can be further enlarged.

It is yet another object of this invention that chemiluminescent products resulting from the action of hydrolytic enzymes on chemiluminescent substrates do not undergo substantial decomposition during the enzymatic reaction, and thus can be accumulated until triggered by a light-releasing reagent.

The combined objects and advantages of this invention indicated above are attained by:

A. Firstly, a chemiluminescent substrate of hydrolytic enzyme having the following general Formula I, as follows:

Lumi-M-P              Formula I where "Lumi" is a chemiluminescent moiety capable of producing light (a) by itself, (b) with MP attached and (c) with M attached. Lumi includes, but is not limited to, chemiluminescent acridinium compounds (e.g., acridinium esters, acridinium carboxyamides, acridinium thioesters and acridinium oxime esters), benzacridinium compounds, quinolinium compounds, isoquinolinium compounds, phenanthridinium compounds, and lucigenin compounds, or the reduced (e.g., acridans) or non-N-alkylated forms (e.g., acridines) of the above, as well as spiroacridan compounds, luminol compounds and isoluminol compounds and the like. M is a multivalent heteroatom having at least one lone pair of electrons selected from oxygen, nitrogen and sulfur, directly attached to the light emitting moiety of Lumi at one end and to P at the other end. (When M alone is attached to Lumi to form Lumi-M, it does, of course, have either a proton or a counterion associated with it or is in the form of an ion.) P is a group that can be readily removed by hydrolytic enzymes, as discussed in more detail hereinafter.

The light emitting moiety of Lumi is well known. For example, when Lumi is an acridinium compound or luminol, the light emitting moiety is the acridinium nucleus or phthaloyl moiety, respectively.

B. Secondly, an enzymatic reaction having the following general reaction A, as follows:

Reaction A

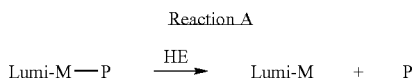

where HE is a hydrolytic enzyme, such as phosphatase, glycosidase, peptidase, protease, esterase, sulfatase or guanidinobenzoatase. Lumi-M-P is a chemiluminescent substrate of a hydrolytic enzyme. Lumi-M is a chemiluminescent product having physical and/or chemical properties different from those of Lumi-M-P. Said physical and/or chemical properties include emission wavelength, quantum yield, light emission kinetics, fundamental net charge distribution, dipole moment, π-bond orders, free energy, or apparent hydrophobicity/hydrophilicity, solubility, affinity and other properties.

C. Light releasing reactions which take place on both Lumi-M-P and Lumi-M.

It is one object of this invention to provide novel light-releasing reagent compositions and reagent addition protocols for triggering light emission from chemiluminescent substrates and products that surprisingly result in better distinction between the signals of the chemiluminescent substrates and products. Said light-releasing reagent compositions can be a single reagent and/or multiple reagents, and addition of said multiple reagents to the reaction vessel can be synchronous or sequential. According to the invention, the light releasing reactions may take place on both Lumi-M-P and Lumi-M, as shown in Formula I.

It is another object of this invention that said light-releasing reagent compositions comprise one or more peroxides or peroxide equivalents, and said peroxides or peroxide equivalents include, but are not limited to, hydrogen peroxide.

It is yet another object of this invention that said light-releasing reagent compositions interact with said chemiluminescent substrate and product differentially so that the differentiation between the two signals is optimized.

It is yet another object of this invention that said light-releasing reagent compositions contain one or more enhancers selected from organic, inorganic or polymeric compounds with a broad range of molecular weights, which differentially enhance the light output from either the substrate or the product.

It is yet another object of this invention that said light-releasing reagent compositions contain also one or more quenchers, blockers or inhibitors selected from organic, inorganic or polymeric compounds with a broad range of molecular weights such that they differentially quench, block or reduce the light output from either the substrate or the product.

The combined objects and advantages of this invention indicated above are attained by a light-releasing reagent composition. Said light releasing reagent composition consists of two separate reagents, which are sequentially added to a solution containing the chemiluminescent substrate and/or product. The first reagent contains acidic hydrogen peroxide solution, and the second reagent contains an alkaline solution with one or more detergents. Alternatively, to the advantage of better distinction between the signals of certain chemiluminescent substrates and their products, the first reagent contains an alkaline solution with one or more detergents, and the second reagent contains hydrogen peroxide solution.

It is another object of this invention to provide optimal light detection methods for said chemiluminescent reactions, so that the differentiation between light emissions of the substrate and product is optimized for specific applications. Said optimal detection methods comprise the use of a light detection apparatus, which includes a luminometer, a Charge-Coupled Device (CCD) camera, an X-ray film, and a high-speed photographic film. Said luminometer comprises a blue-sensitive photomultiplier tube (PMT), or a red-sensitive PMT, or other PMTs optimized for specific applications. Said optimal light detection methods also include the use of an optical filtering device to block or reduce unwanted light emission either from the substrate or from the product. Said optimal detection methods further include a method and/or a device for detecting or registering light in a sequential manner that eliminates or reduces unwanted signal from the substrate.

The combined objects and advantages of this invention indicated above are attained by one or more light detection methods. One preferred light detection method comprises the use of a PMT and a long wave pass filter in an enzymatic reaction to detect the chemiluminescent signal from the product that emits light at a wavelength longer than that of the substrate. Another said light detection method comprises the use of a red-sensitive PMT at low temperature (i.e., below 4° C.) and a long wave pass filter to improve the detectability of the chemiluminescent product that emits light at a wavelength longer than that of the substrate. Still another said light detection method comprises the use of blue-sensitive PMT and a short wave pass filter to detect the decrease of chemiluminescent signal from the substrate whose emission wavelength is shorter than that of the product. Yet another said light detection method comprises the use of a PMT with or without an optical filter, within a fixed light measuring time, to detect the decrease of chemiluminescent signal from the substrate whose emission kinetics is faster than that of the product.

It is yet another object of this invention to provide methods and assays comprising the use of one or more said chemiluminescent substrates from Formula I, one or more said hydrolytic enzymes, one or more said light-releasing reagent compositions, and one or more said optimal light detection methods.

It is yet another object of this invention to provide methods and assays in using one or more said chemiluminescent substrates to detect, qualitatively or quantitatively, the presence of one or more said hydrolytic enzymes or enzyme conjugates that are present either as labels or as markers of biological samples.

It is a further object of this invention to provide a method that utilize one or more said chemiluminescent substrates from Formula I, and one or more said labeled hydrolytic enzymes to detect, qualitatively and/or quantitatively, the presence of one or more analytes.

Finally, it is also an object of this invention to provide synthetic methods and intermediates related to the syntheses of said chemiluminescent substrates.

DETAILED DESCRIPTION OF THE INVENTION

Figure 1A:
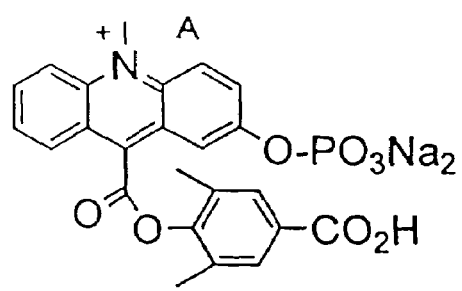
FIGS. 1A–1F show structures of chemiluminescent substrates (2-phos-acridinium esters), capable of short wavelength emission, and their corresponding chemiluminescent products (2-hydroxyl-acridinium esters), capable of long wavelength emission.
Figure 1B:
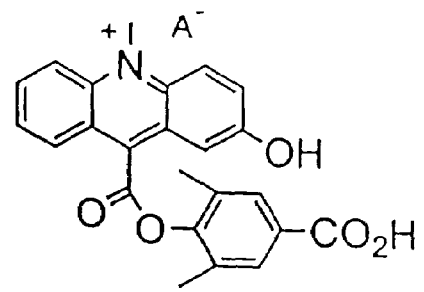
Figure 1C:
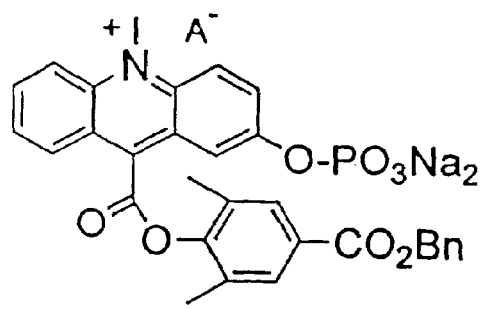
Figure 1D:
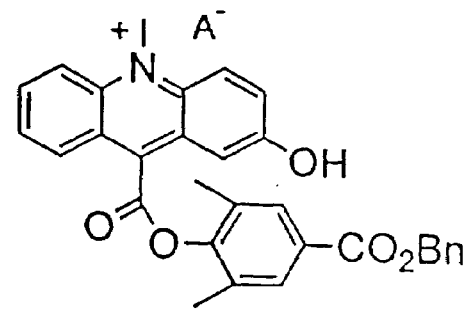
Figure 1E:
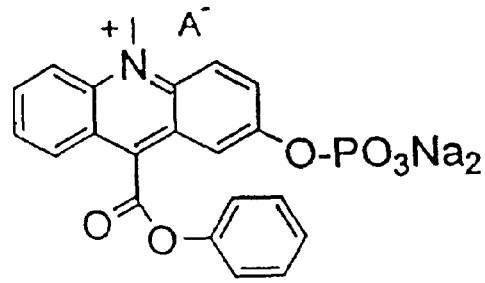
Figure 1F:
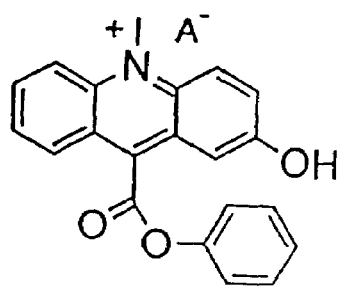
Figure 1G:
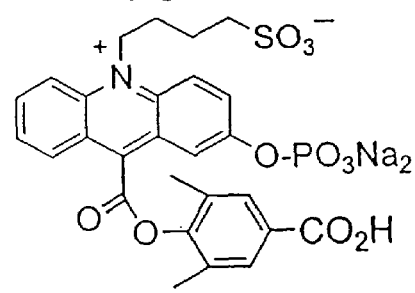
FIGS. 1G–1L show structures of chemiluminescent substrates (2-phos-acridnium esters) capable of short wavelength emission, and their corresponding chemiluminescent products (2-hydroxyl-acridinium esters), capable of long wavelength emission, including spiro compounds (FIGS. 1K–1L).
Figure 1H:
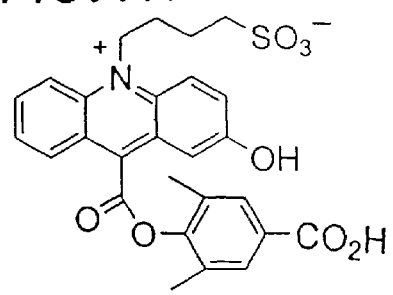
Figure 1I:
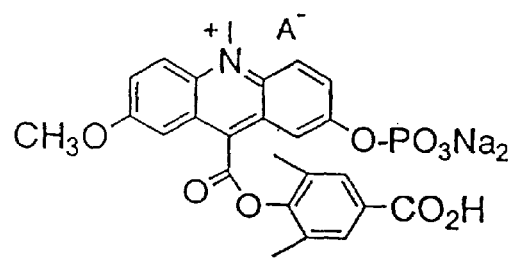
Figure 1J:
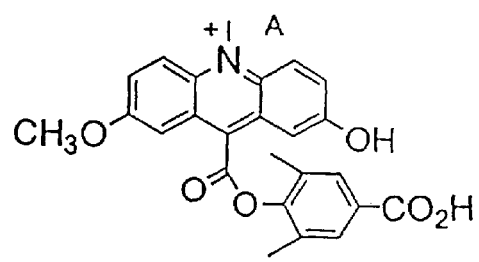
Figure 1K:
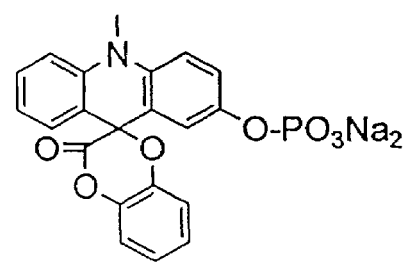
Figure 1L:
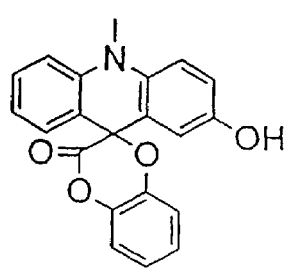
Figure 1M:
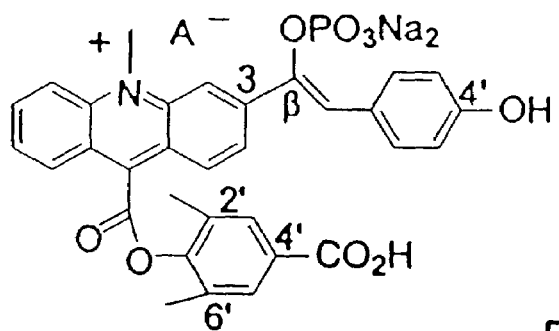
FIGS. 1M–1P show structures of chemiluminescent substrates capable of long wavelength emission and its corresponding products capable of short wavelength emission.
Figure 1N:
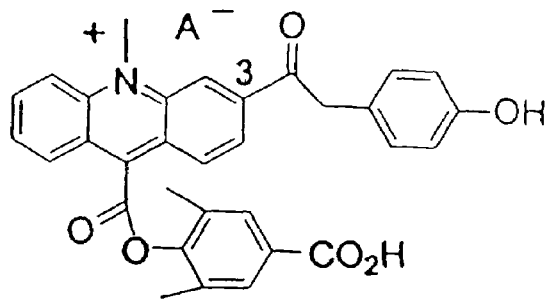
Figure 1O:
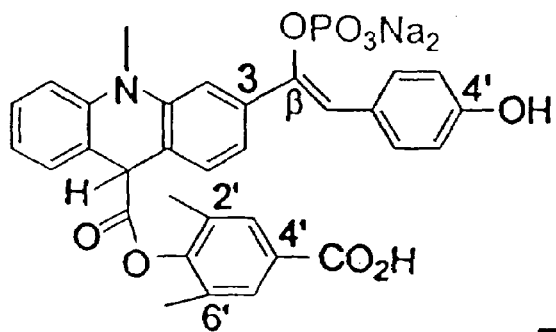
Figure 1P:
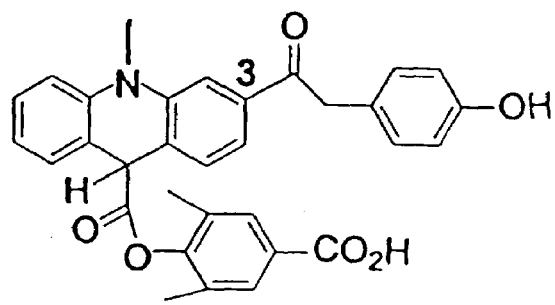
Figure 1Q:
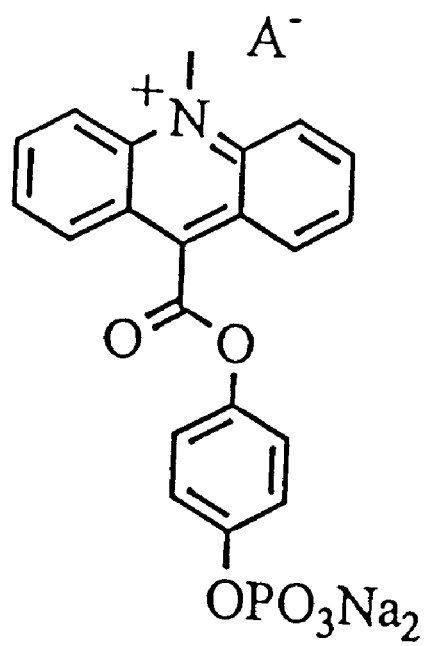
FIGS. 1Q–1R show structures of chemiluminescent substrates and its corresponding product, which have different emission kinetics.
Figure 1R:
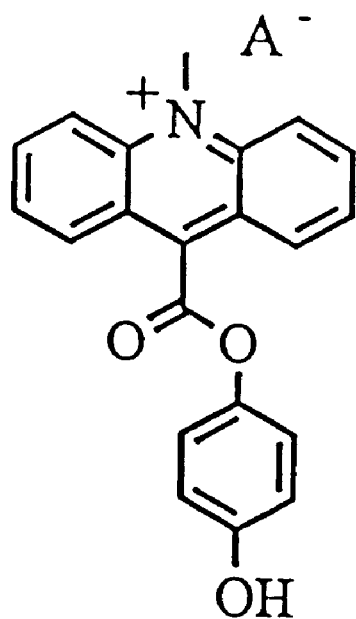

It has been discovered that certain novel chemiluminescent compounds having a general Formula I are substrates of hydrolytic enzymes, with the structure of Formula I shown as follows:

Lumi-M-P  Formula I

As shown in Formula I, Lumi is defined as a chemiluminescent moiety capable of producing light (a) by itself, (b) with MP attached and (c) with only M attached. M is defined as a multivalent heteroatom having at least one lone pair of electrons selected from oxygen, nitrogen and sulfur, wherein M is directly attached to the light emitting moiety of Lumi at one end and to P at the other end. P is a group that can be readily removed by hydrolytic enzymes. When M alone is attached to Lumi to form Lumi-M, M has either a proton or a counterion associated with it or is in the form of an ion.

The chemiluminescent moiety of Lumi includes, but is not limited to, acridinium compounds (including acridinium esters (Law et al., U.S. Pat. No. 4,745,181), acridinium carboxyamides (Mattingly et al., U.S. Pat. No. 5,468,646 and Kinkel et al., *J. Biolumin. Chemilumin.*, 4, 136–139, (1989)), acridinium thioesters (Kinkel et al., *J. Biolumin. Chemilumin.*, 4, 136–139, (1989)) and acridinium oxime esters (Ghitti et al., WO 98/56765)) benzacridinium compounds, quinolinium compounds, isoquinolinium compounds, phenanthridinium compounds, and lucigenin compounds, or the reduced (e.g., acridans) or non-N-alkylated (e.g., acridines) forms of the above, spiroacridan compounds (Singh et al., WO 94/02486), luminol compounds, and isoluminol compounds, as shown below.

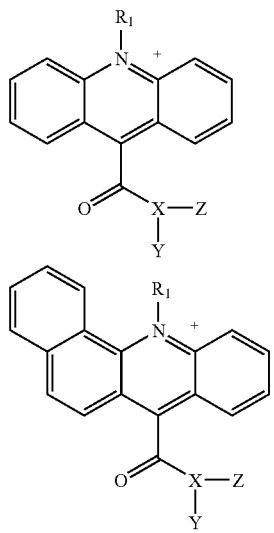

-continued

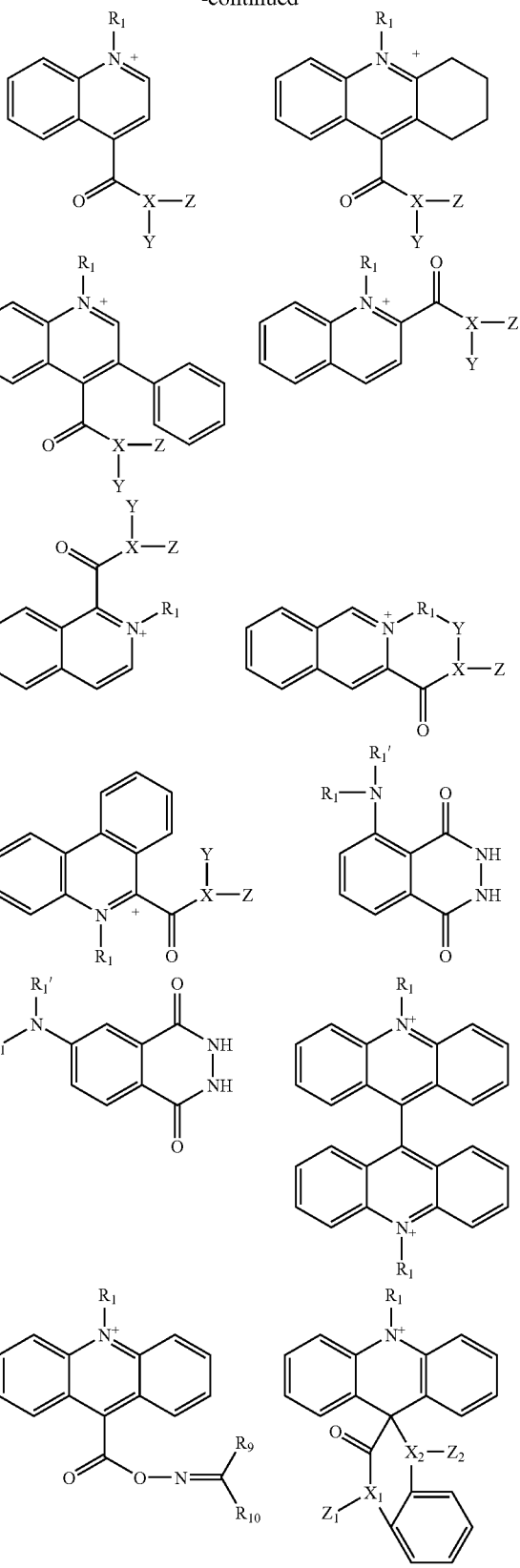

Hydrolytic enzymes that may be used in Reaction A, shown previously, include, but are not limited to, phosphatases: alkaline phosphatase, acidic phosphatase, phospholipase, phosphodiesterase, and pyrophosphatase; glycosidases: β-galactosidase, α-galactosidase, α-(D-)-glucosidase, β-glucosidase, β-glucuronidase, α-mannosidase, N-acetyl-β-D-glucosaminidase, neuraminidase, cellulase, and β-fucosidase; peptidases and proteases: dipeptidylpeptidases I, II and IV, plasminogen activator, calpain, elastase, trypsin, cathepsins B, C, L and O, urokinase, granzyme A, prostatin, thrombin, trypase, follipsin, kallikrein, plasmin, prohormone thiol protease, amyloid A4-generating enzymes, human adenovirus proteinase, kallikrein, and HIV protease; esterases: cholinesterase, and lipase; and sulfatase, and guanidinobenzoatase.

Being thermally and hydrolytically stable in an aqueous environment, the inventive chemiluminescent substrates undergo readily hydrolytic reaction in the presence of hydrolytic enzymes, and the resulting products, as represented by Lumi-M in Reaction A, are also chemiluminescent. It has also been unexpectedly discovered that the light emission characteristics (emission wavelength, kinetics, and quantum yield) of the products differ significantly from those of their corresponding chemiluminescent substrates due to the change in some of the chemical and physical properties of the chemiluminescent products generated by hydrolytic reaction. Those chemical and physical properties include the fundamental net charge distribution, dipole moment, π-bond orders, free energy, or the apparent hydrophobicity/hydrophilicity, solubility, and affinity, etc. As a result, a discernible signal due to one or more of these differences is generated, and thus is useful for qualitative or quantitative determination of the specific hydrolytic enzyme that is involved in the Reaction A, shown previously.

1. Substrates and Products Having Different Emission Wavelength

One preferred class of chemiluminescent substrates selected from Formula I in this invention is related to novel chemiluminescent acridinium compounds represented in Formula II, shown below, with said compounds capable of being chemically triggered to produce light:

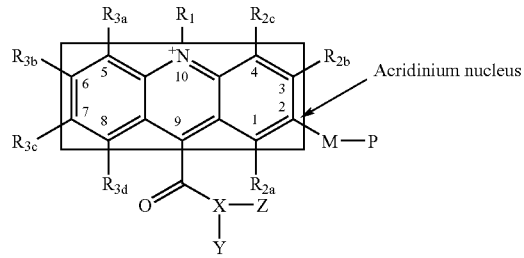

Formula II

As shown in Formula II, P is preferably a group that is thermally and hydrolytically stable in aqueous medium, but is readily removable by a hydrolytic enzyme to form Lumi-M; and M is preferably a multivalent heteroatom having at least one lone pair electrons selected from oxygen, nitrogen and sulfur, and a strong ability of donating electrons to the acridinium nucleus after the removal of P. Preferably, after the removal of the protective group (P) by a hydrolytic enzyme, M becomes ionizable in the medium of the reaction to bear a negative charge, thus strongly donating electrons to the acridinium ring system.

As shown in Formula II, $R_1$ is preferably an alkyl, alkenyl, alkynyl or aralkyl group containing from 0 to 20 heteroatoms; more preferably $R_1$ is methyl and most preferably $R_1$ is sulfoalkyl or an alkyl containing-one or more hydrophilic groups selected from sulfonate, sulfate, —$CO_2H$, phosphonate, ethylene glycol, polyethylene glycol, quaternary ammonium (—$N^+R_3$), or any groups containing one or more of the above (—$N^+R_3$). The inclusion of the hydrophilic moiety in $R_1$ serves to increase water solubility of the molecule.

As shown in Formula II, $C_1$, $C_3$, $C_6$, and $C_8$ peri-positions of the acridinium nucleus may be unsubstituted or substituted. When one or more of said positions are substituted, the substituents ($R_{2a}$, $R_{2b}$, $R_{3b}$, and $R_{3d}$, respectively) are identical or different, selected from —R, substituted or unsubstituted aryl (ArR or Ar), halides, nitro, sulfonate, sulfate, phosphonate, —$CO_2H$, —C(O)OR, cyano (—CN), —SCN, —OR, —SR, —SSR, —C(O)R, —C(O)NHR, ethylene glycol, or polyethyelene glycol. R is selected from the group consisting of alkyl, alkenyl, alkynyl aryl, and aralkyl containing from 0 to 20 heteroatoms.

As shown in Formula II, the $C_4$, $C_5$, and $C_7$ peri-positions of the acridinium nucleus may be unsubstituted or substituted. When one or more of said positions are substituted, the substituents ($R_{2c}$, $R_{3a}$, and $R_{3c}$, respectively) are identical or different and are defined the same as $R_{2a}$, $R_{2b}$, $R_{3b}$, and $R_{3d}$. Alternatively, one of $R_{2c}$, $R_{3a}$ and $R_{3c}$ may be defined as M-P. In this case, $C_2$ peri-position may be unsubstituted or substituted. When it is substituted, the substituents may be defined as $R_{2a}$, $R_{2b}$, $R_{3b}$, and $R_{3d}$.

Alternatively, as shown in Formula II, any two adjacent substituents at the acridinium nucleus peri-positions can be linked as in the following examples, so as to form additional unsaturated carbocyclic and/or heterocyclic rings fused to the attached acridinium nucleus, as shown below.

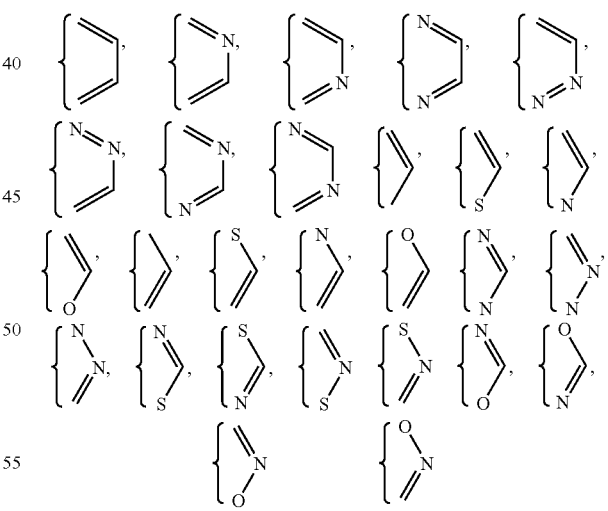

As provided in Formula II, $A^-$ is a counter ion for the electroneutrality of the quaternary nitrogen of the acridinium compounds, which is introduced as a result of quarternerization of the intermediate acridines with alkylating agents, or due to anionic exchange which occurs during the subsequent synthetic steps or in the following work-up of reaction mixtures and purification of the desired compounds in a liquid phase containing excess amounts of other anions. Examples of such counter ions include $CH_3SO_4^-$, $FSO_3^-$, $CF_3SO_3^-$, $C_4F_9SO_3^-$, $CH_3C_6H_4SO_3^-$, halide, $CF_3COO^-$, $CH_3COO^-$, and $NO_3^-$. $A^-$ is typically not present if the $R_1$ substituent contains a strongly ionizable group that can form an anion and pair with the quaternary ammonium cationic moiety.

X is nitrogen, oxygen or sulfur.

When X is oxygen or sulfur, Z is omitted and Y is a substituted or unsubstituted aryl group, and preferably Y is a polysubstituted aryl group of the formula III:

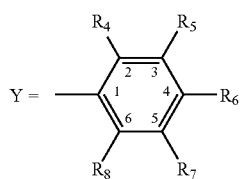

Formula III

As shown in Formula III, $R_4$ and $R_8$ may be identical or different and identified as an alkyl, alkenyl, alkynyl, alkoxyl (—OR), alkylthiol (—SR), or substituted amino groups that serve to stabilize the —COX— linkage between the acridinium nucleus and the Y moiety, through steric and/or electronic effect; preferably $R_4$ and $R_8$ are short chain alkyl groups having from 1 to 10 carbon atoms, more preferably a methyl group, or at least one of $R_4$ and $R_8$ is as defined while the other is a hydrogen or an atom selected from halides. $R_5$, $R_6$ and $R_7$ may be identical or different, selected from hydrogen, —R, substituted or unsubstituted aryl, halides, amino, —NHR, $NR_2$, quaternary ammonium (—$N^+R_3$), hydroxyl, nitro, nitroso, sulfonate, sulfate, cyano (—CN), phosphonate, $CO_2H$, —SCN, —OR, —SR, —SSR, —C(O)R, —C(O)NHR, —NHC(O)R, ethylene glycol, or polyethyelene glycol. Preferably, $R_5$, $R_6$ and $R_7$, identical or different, are a hydrophilic group selected from sulfonate, sulfate, —$CO_2H$, phosphonate, ethylene glycol, polyethylene glycol, quaternary ammonium (—$N^+R_3$), or any groups containing one or more of the above hydrophilic moiety, which serves to increase water solubility of the molecule.

Any adjacent two groups of $R_4$ to $R_8$ in Formula III can form one or more additional fused hydrocarbon aromatic rings or heteroaromatic rings with or without substitutions. The additional fused hydrocarbon aromatic rings and heteroaromatic rings include, but are not limited to, benzene, naphthlene, pyridine, thiophene, furan, and pyrrole, etc.

Alternatively, Formula II can represent another class of Lumi-M-P where Lumi is an acridinium oxime ester (as described in WO 98/56765 hereby incorporated by reference), and M-P are as defined above. When the Lumi is an acridinium oxime ester, said X, Y and Z of Formula II are separately defined.

As shown in Formula II, when X is oxygen, Z is omitted and Y is defined above or —N=$CR_9R_{10}$, wherein $R_9$ and $R_{10}$, are identical or different, and are selected from hydrogen, substituted or non-substituted aryl, alkyl, alkenyl, alkynyl, halide, alkoxyl and aryloxy groups.

As shown in Formula II, when X is nitrogen, then Z is —$SO_2$—Y', Y' has the same definition of Y as defined above, and Y and Y' may be the same or different. Additionally, Y itself can be a branched or straight-chain alkyl containing from 1 to 20 carbons, halogenated or unhalogenated, or can be a substituted aryl, or heterocyclic ring system.

Thus, given the alternatives discussed above, X, Y and Z in Formula II can be defined as follows:

X is nitrogen, oxygen or sulfur; such that, when X is oxygen, Z is omitted and Y is a substituted or unsubstituted aryl group or —N=$CR_9R_{10}$, wherein $R_9$ and $R_{10}$ may be the same or different and are selected from hydrogen, substituted or non-substituted aryl, alkyl, alkenyl, alkynyl, halide, alkoxyl and aryloxy groups;

when X is sulfur, Z is omitted and Y is a substituted or unsubstituted aryl group;

when X is nitrogen, Z is —$SO_2$—Y', Y' being defined the same as Y above; Y is as defined above or can be a branched or straight-chain alkyl containing 0 to 20 carbons, halogenated or unhalogenated, or a substituted aryl, or heterocyclic ring system; and Y and Y' can be the same or different.

Structurally closely related to chemiluminescent acridinium compounds of Formula II are their reduced forms, chemiluminescent acridan compounds, represented as Formula IV, where all substitutions are as defined in Formula II. These compounds can be chemically triggered to produce light via formation of acridinium intermediates and/or via direct oxidation to form electronically excited products, which are the same products of acridinium compounds of Formula II.

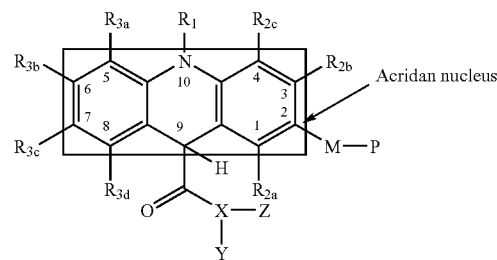

Formula IV

Acridan nucleus

Another class of chemiluminescent substrates structurally related to acridinium substrates of Formula II are spiroacridan compounds having Formula V, wherein $X_1$ and $X_2$ may be identical or different, are selected from the group consisting of oxygen, sulfur and nitrogen, and when $X_1$ and/or $X_2$ are oxygen or sulfur, $Z_1$ and/or $Z_2$ are omitted, when $X_1$ and/or $X_2$ are nitrogen, $Z_1$ and/or $Z_2$ are hydrogen, alkyl, aryl or —$SO_2$—Y'; G is a group connecting $X_1$ and $X_2$ to form a ring having 5 to 10 members; and $R_1$, $R_{2a-c}$, $R_{3a-d}$, M and P are defined in Formula II.

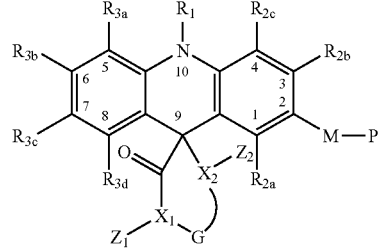

Formula V

Within the chemiluminescent spiroacridan substrates of Formula V is a subclass shown as Formula VI below, where G is singly or multiply substituted ($R_{11}$) or unsubstituted aromatic ring with 0–3 heteroatoms, wherein $R_{11}$ is the group selected from hydrogen, —R, substituted or unsubstituted aryl (ArR or Ar), halides, nitro, sulfonate, sulfate, phosphonate, —$CO_2H$, —C(O)OR, cyano (—CN), —SCN, —OR, —SR, —SSR, —C(O)R, —C(O)NHR, ethylene gly col, or polyethyelene glycol, and said subclass of substrates having Formula VI:

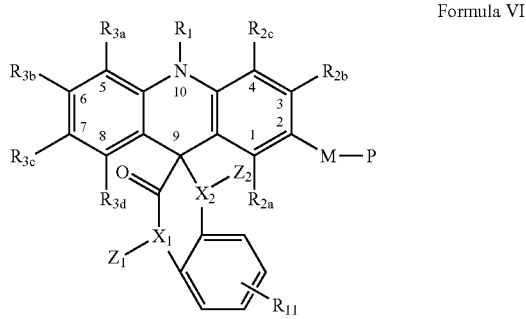

Formula VI

Preferably, novel chemiluminescent acridinium substrates of the present invention of Formula II are a subclass of compounds represented by Formula VII below, wherein multivalent heteroatom M is oxygen (O), and group P is a phosphoryl group, —PO$_3$Na$_2$, where two sodium cations, whose purpose is solely for the eletroneutrality of the molecule, can be exchanged independently with hydrogen, potassium, magnesium, calcium, or other cationic

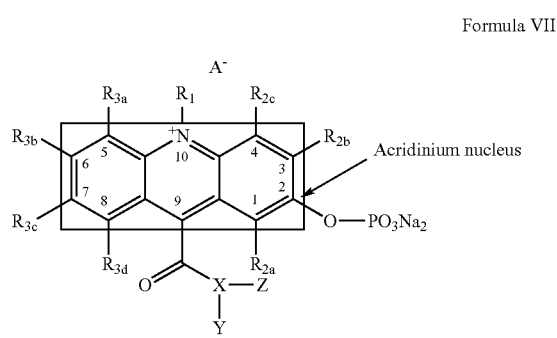

Formula VII

The preferred hydrolytic enzyme (HE) as shown in Scheme I is a hydrolytic phosphatase. Particularly preferred is the use of hydrolytic phosphatase with a compound defined by Formula VII.

Structurally closely related to preferred chemiluminescent acridinium compounds of Formula VII are their reduced forms, chemiluminescent acridans, represented as Formula VIII, where all substitutions are as defined in Formula VII. The compounds of Formula VII may be chemically triggered to produce light via formation of acridinium intermediates and/or via direct oxidation to form electronically excited products, which are the same products of acridinium compounds of Formula VII.

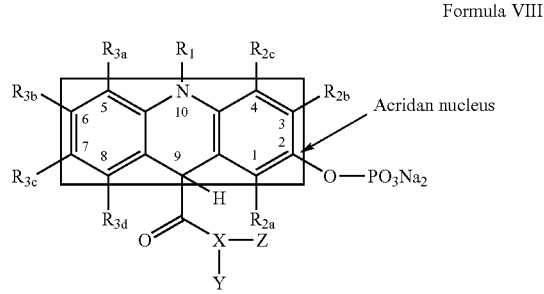

Formula VIII

Another subclass of the compounds structurally related to preferred chemiluminescent acridinium compounds of Formula VII are spiroacridan compounds of Formula IX, wherein, $X_1$, $X_2$, $Z_1$, $Z_2$, R', $R_1$, $R_{2a-c}$, $R_{3a-d}$, M and P are as defined in Formula VI, and two sodium cations are as defined in Formula VII.

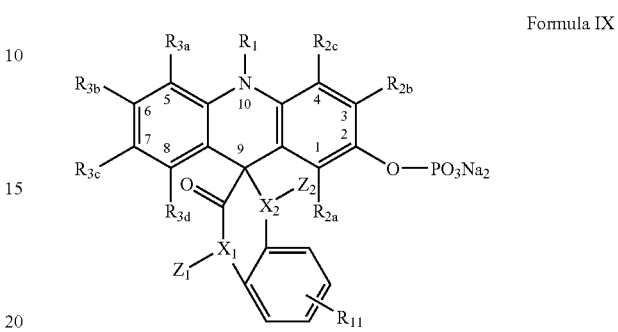

Formula IX

One of the preferred compounds selected from Formula VII, in which $R_{2a-c}$, $R_{3a-d}$, are hydrogen, $R_1$ is methyl, X is oxygen, Z is omitted, and Y is a polysubstituted aryl moiety of Formula III where $R_4$ and $R_8$ are methyl, $R_5$ and $R_7$ are hydrogen, and $R_6$ is carboxyl (—CO$_2$H), is 2-Phos-DMAE, whose structure is shown as 1. (See FIG. 1A. Note: Structure 1 below is also shown in FIG. 1A, attached. Similarly, other structures in this application are referred to by numbers which correspond to the appropriate sequence number in FIG. 1.)

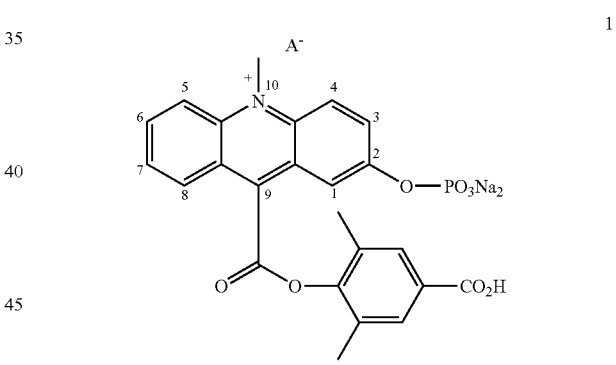

1

Figure 2A:
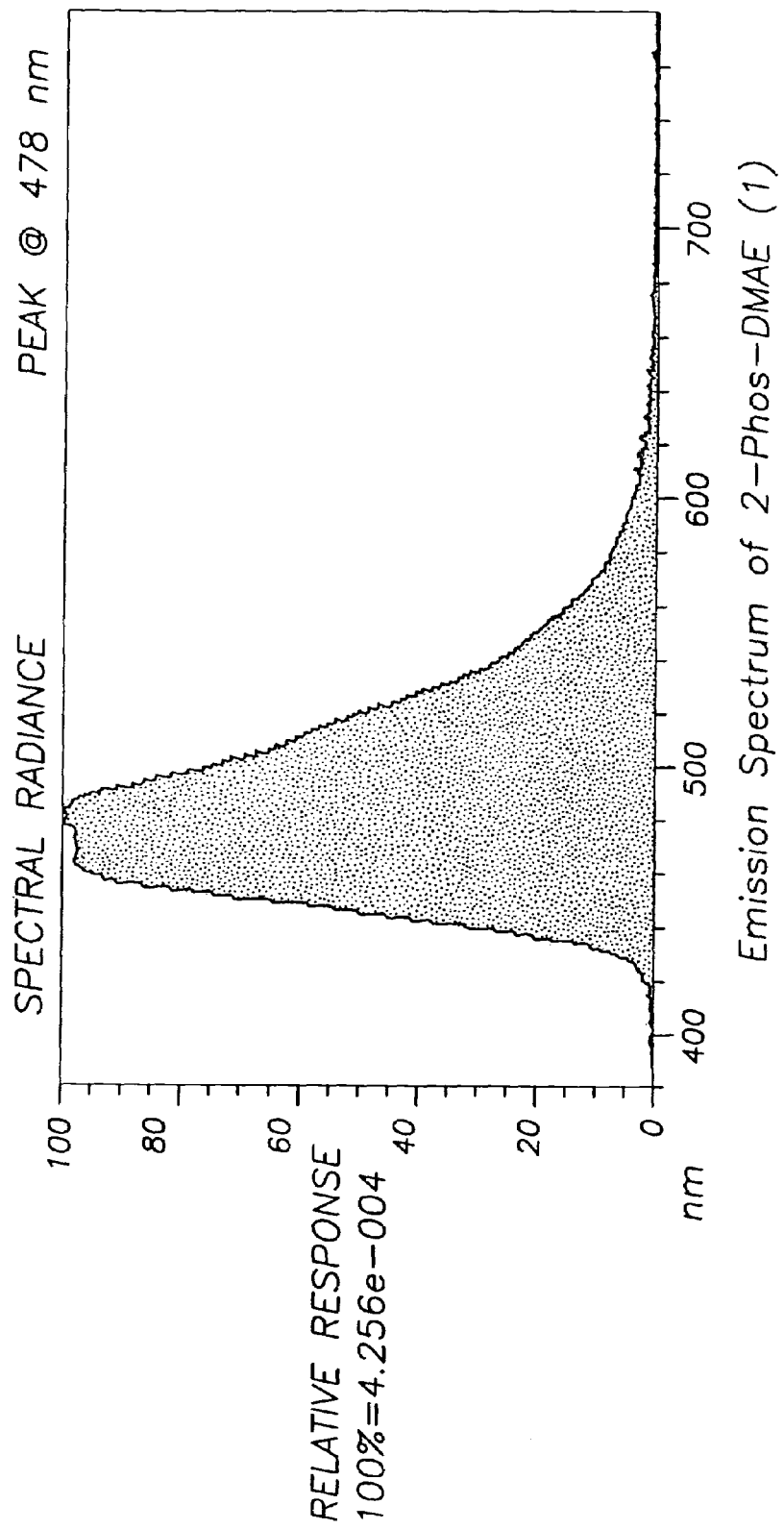
FIGS. 2A–2P are the emission spectra of chemiluminescent substrates (2-phos-acridinium esters) and their corresponding chemiluminescent products (2-hydroxyl-acridinium esters), as well as spectra of chemiluminescent substrates capable of long emission and their corresponding products capable of short emission, determined by a Fast Scanning Spectral System (FSSS) The emission spectra of chemiluminescent substrates and the corresponding products, which have different light emission kinetics, are also shown.
Figure 2B:
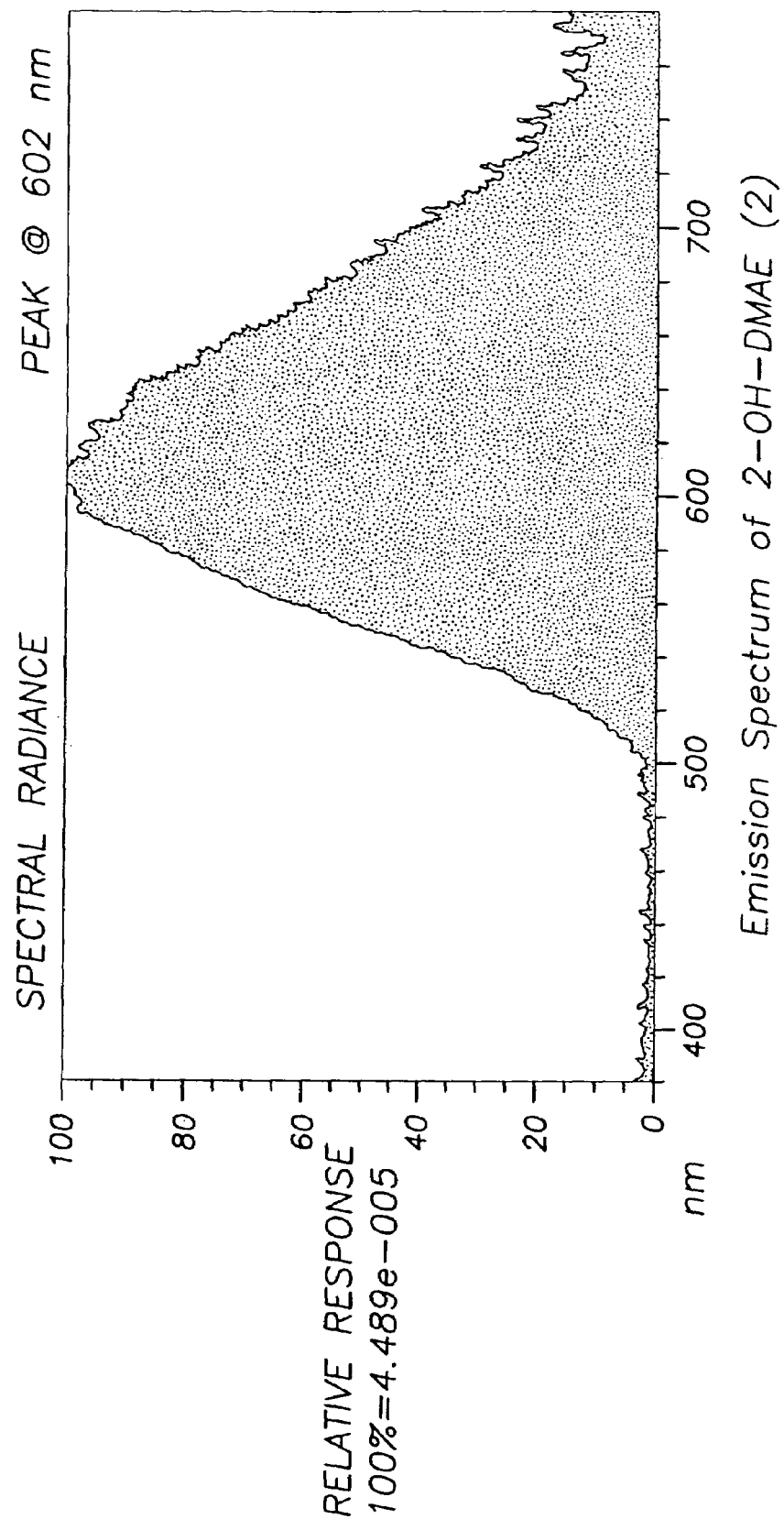
Figure 2C:
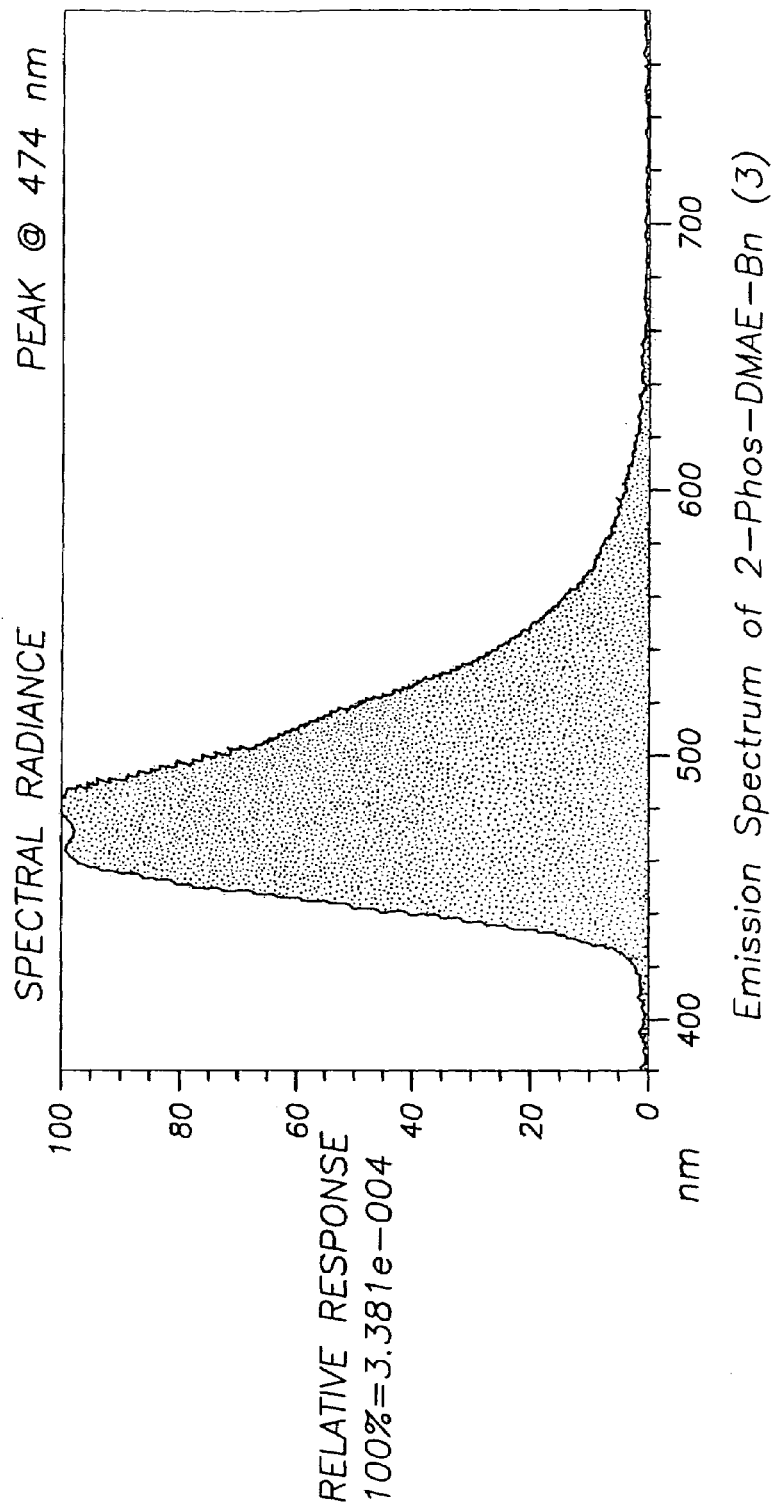
Figure 2D:
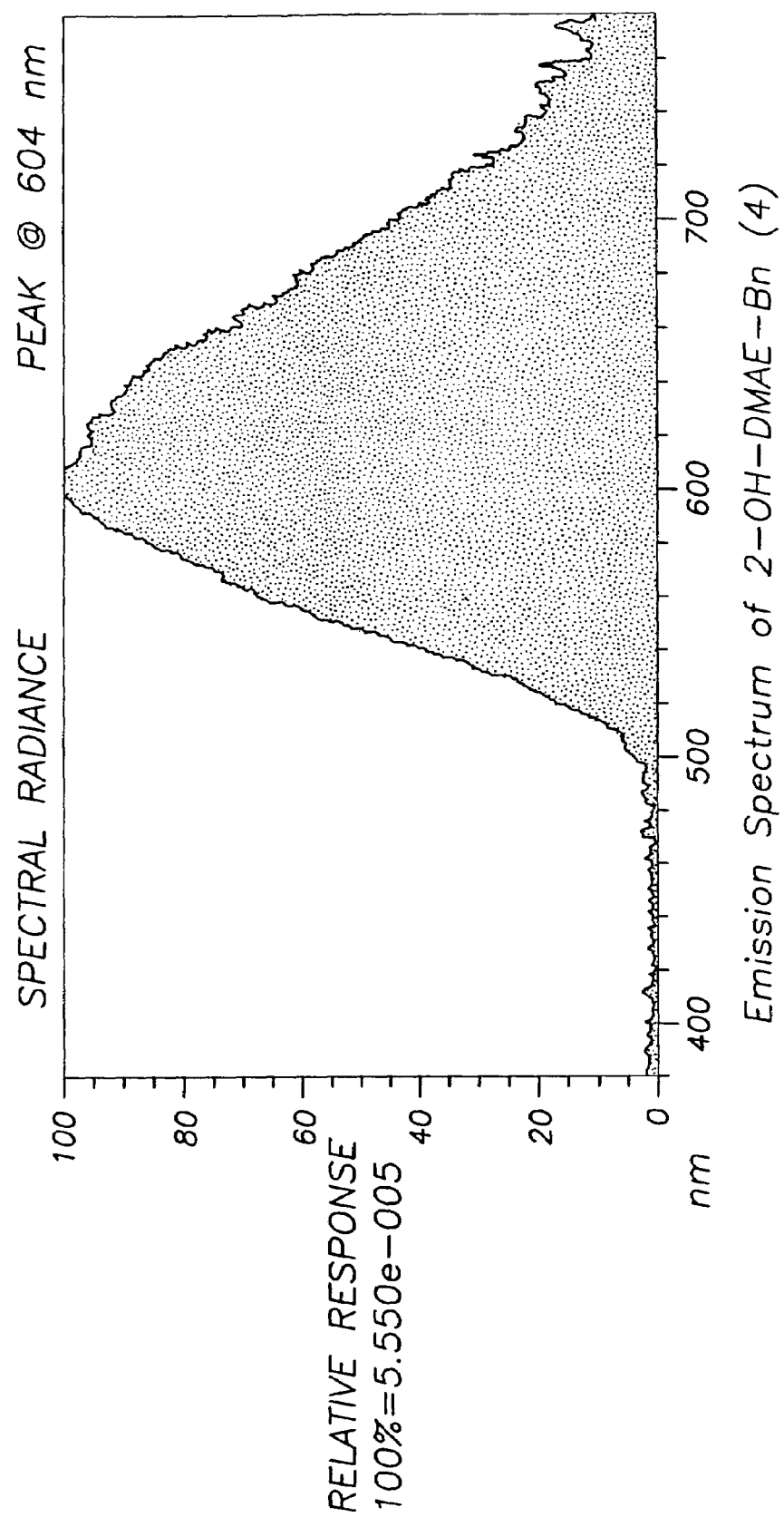
Figure 2E:
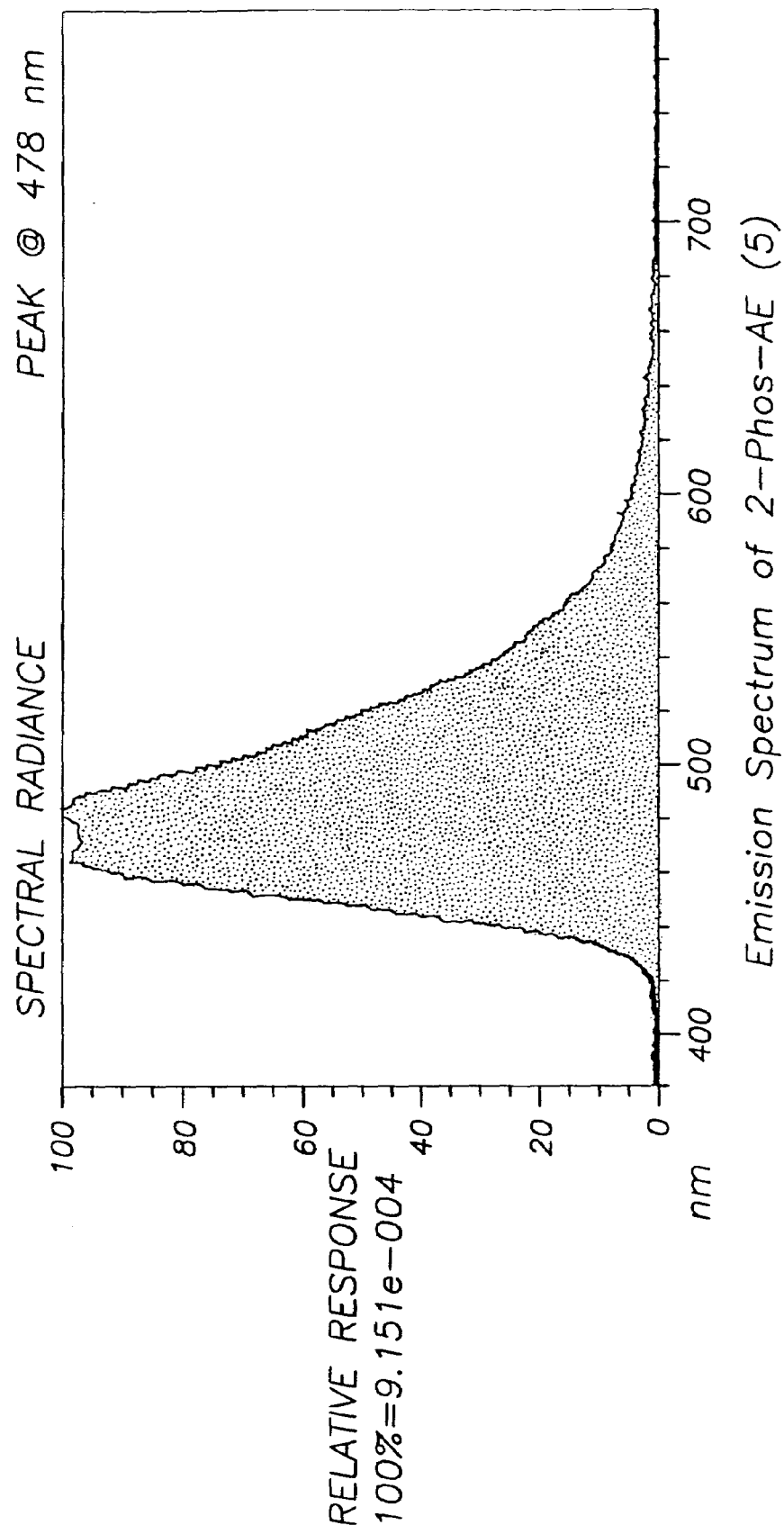
Figure 2F:
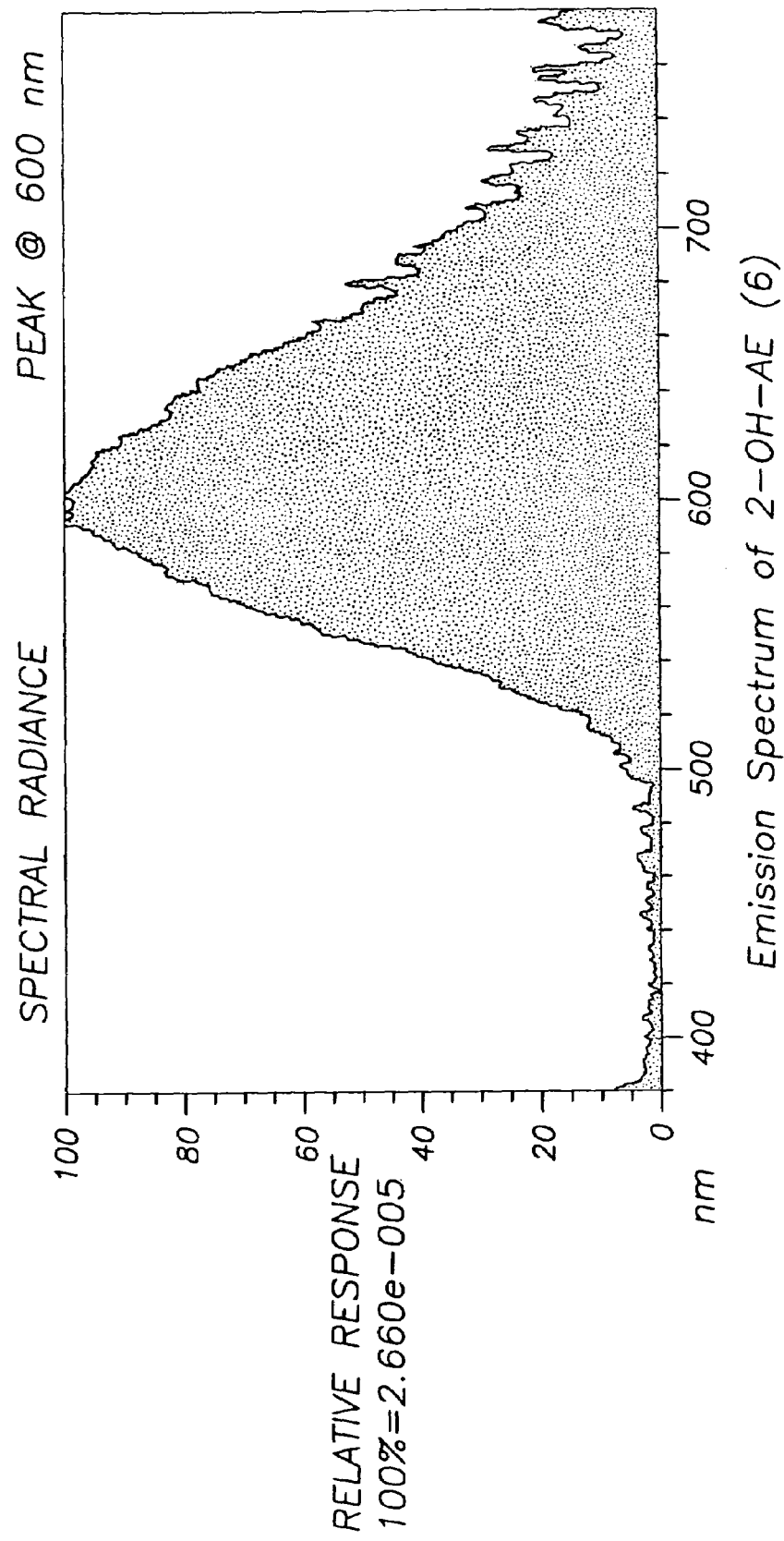
Figure 2G:
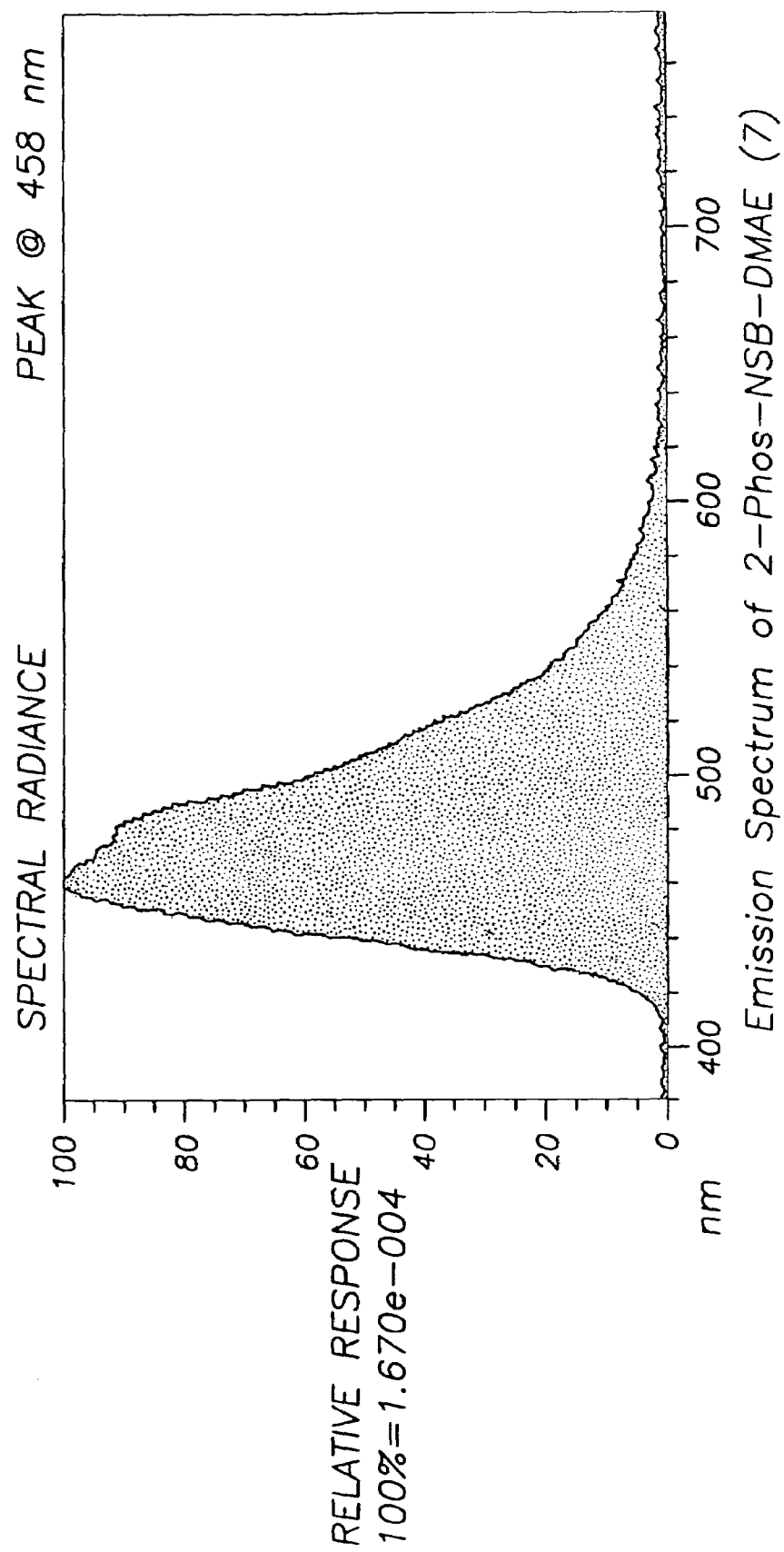
Figure 2H:
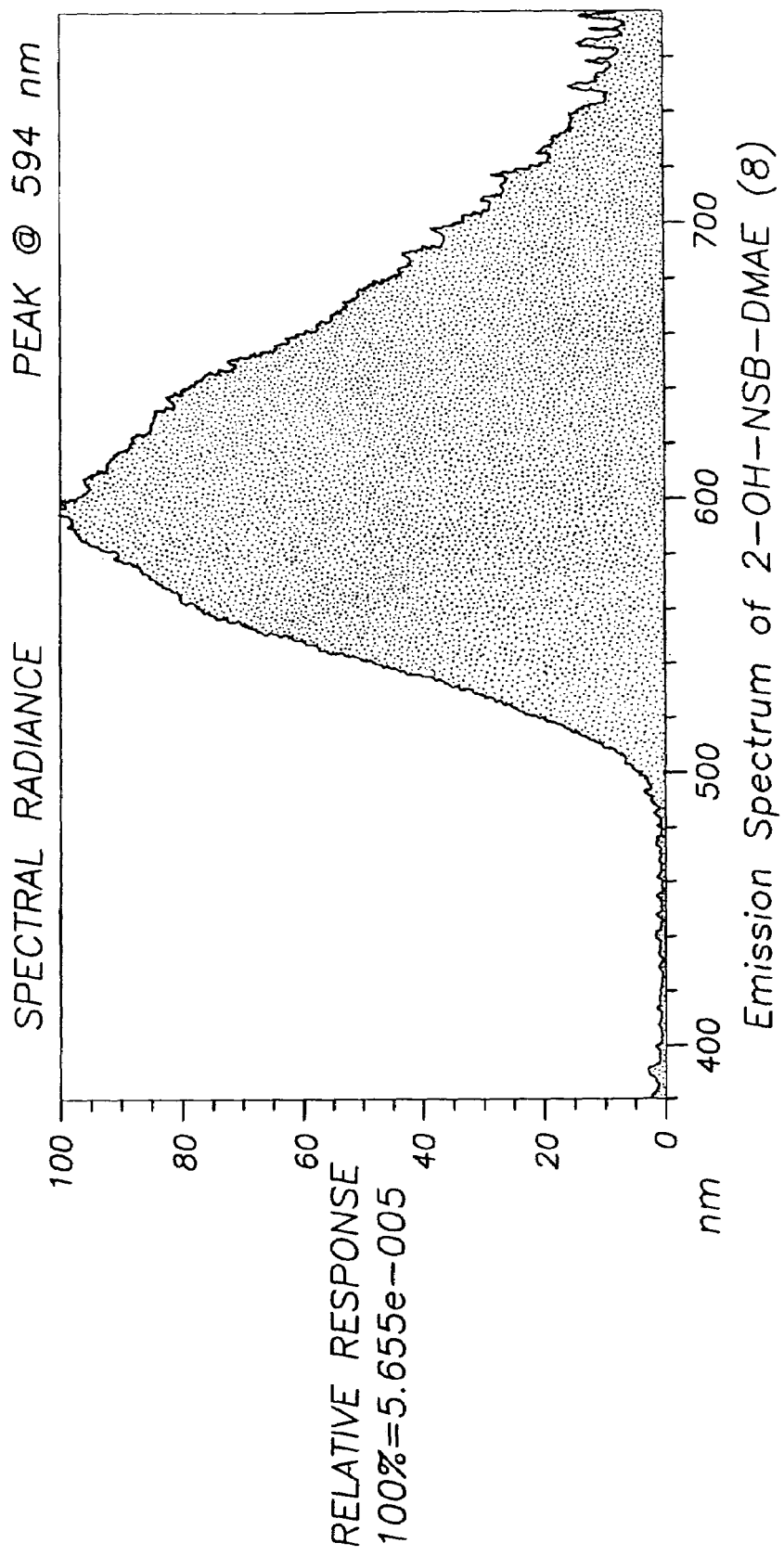
Figure 2I:
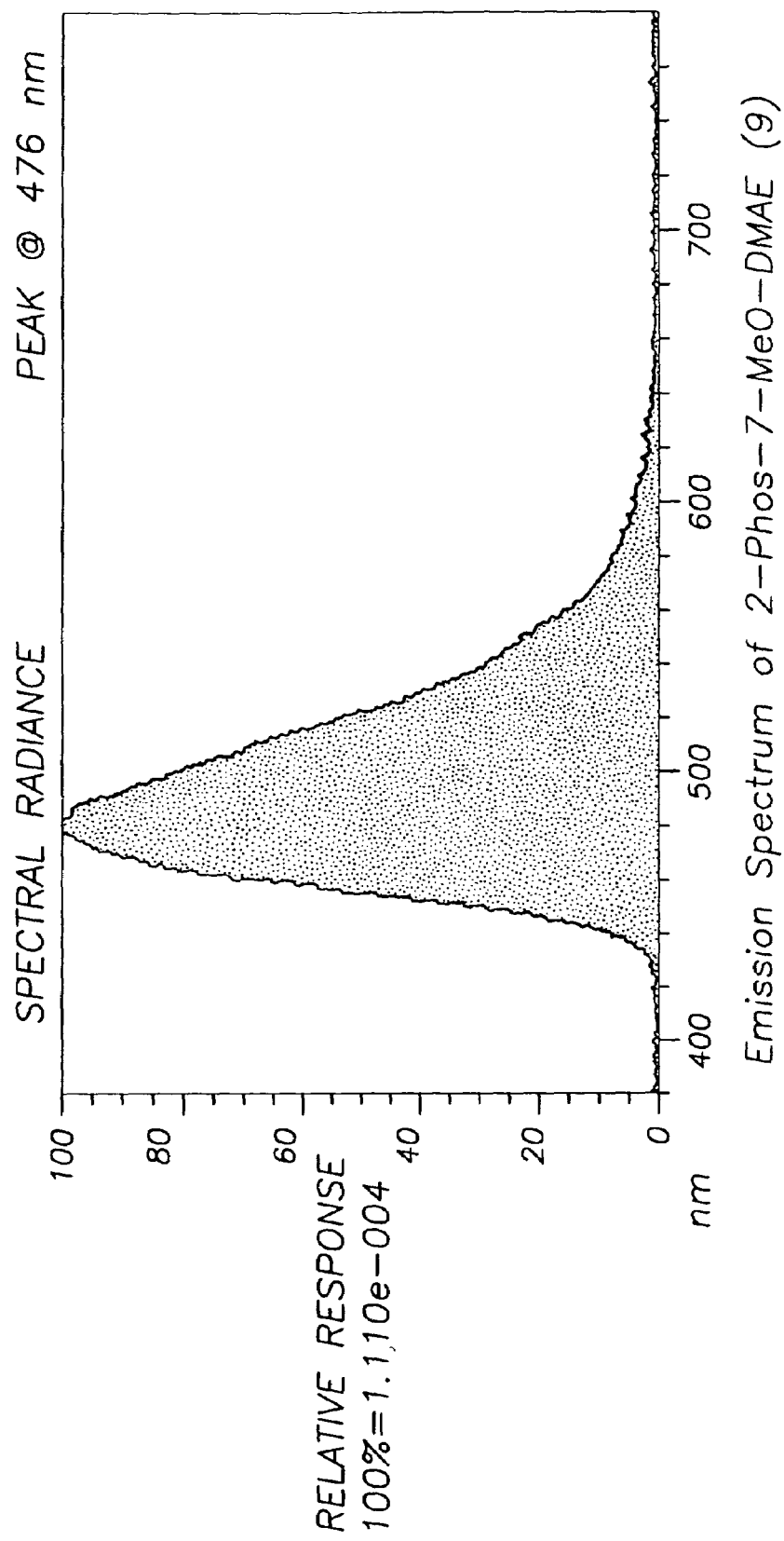
Figure 2J:
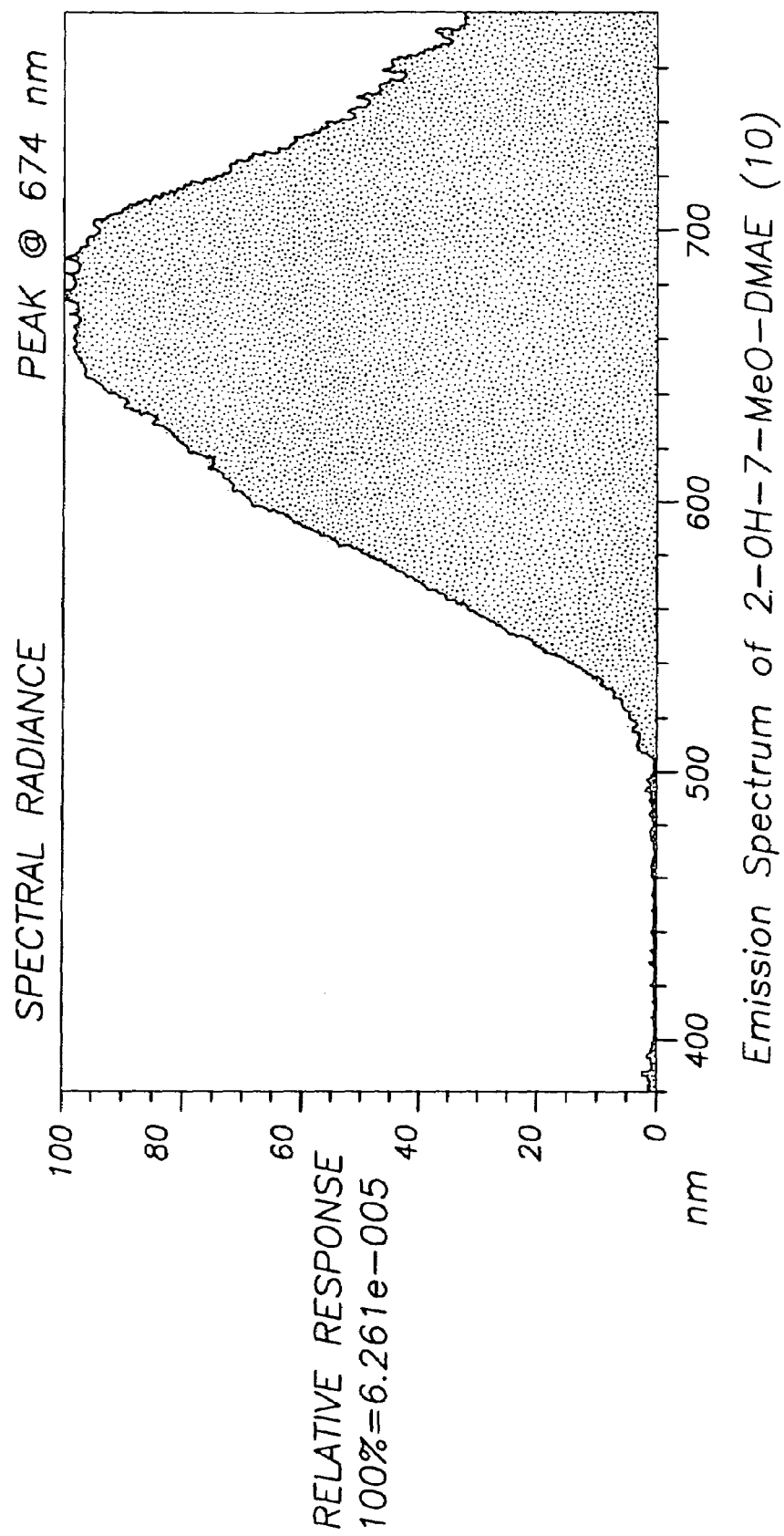
Figure 2K:
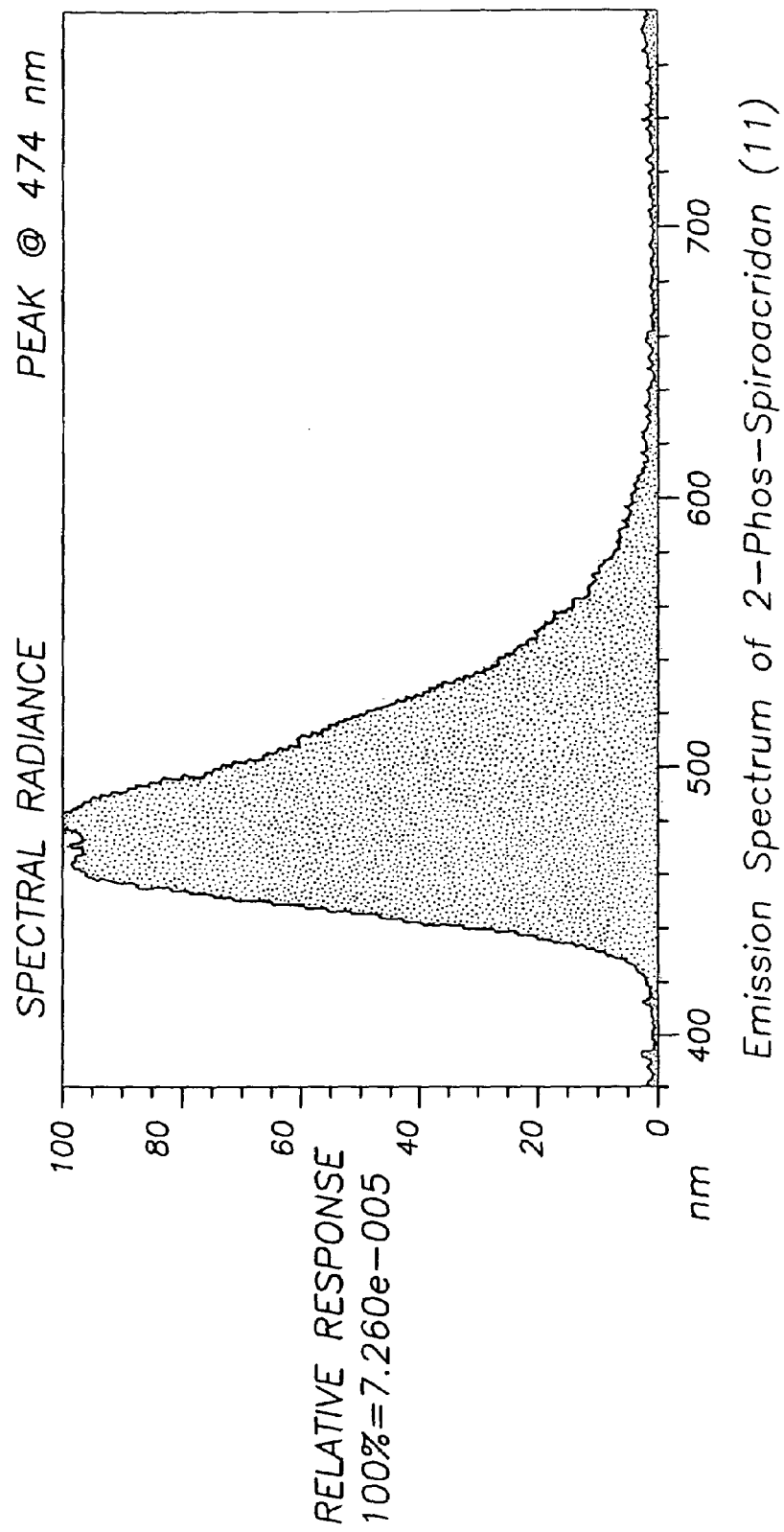
Figure 2L:
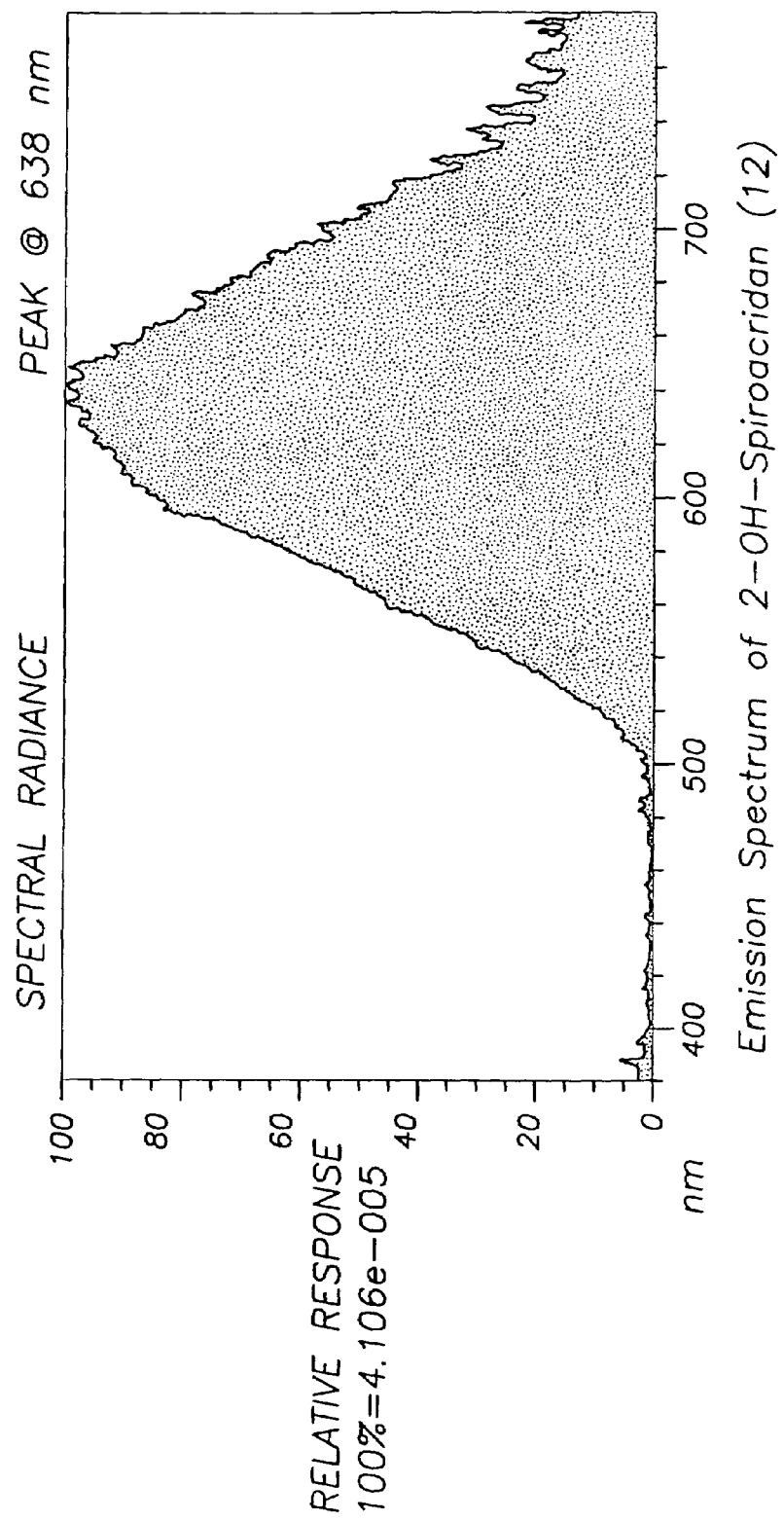

As disclosed in the section of Examples, 2-Phos-DMAE (1) is an excellent substrate of hydrolytic alkaline phosphatase (AP). In alkaline aqueous medium of a wide pH range, it is readily dephosphorylated by AP to form 2-OH-DMAE (2) as illustrated in Reaction B. Both 1 and 2 are chemiluminescent. As disclosed in FIGS. 2A–2B and also in Table 1, it has been unexpectedly discovered that 1 and 2 emit light at different emission maxima when they are treated with hydrogen peroxide in strong alkaline solution, respectively. Specifically, compound 1 emits a strong, visible blue light at λmax 478 nm while compound 2 emits a strong, visible orange light at λmax 602 nm, thus resulting in a bathochromic shift of emission maximum by 128 nm. Several pairs of analogs (3 and 4, 5 and 6, 7 and 8), as well as a pair of spiroacridans (11 and 12), whose structures are given in FIG. 1, also have the same light emission characteristics. Compounds 7 and 8 also carry additional hydrophilic groups on the nitrogen of the acridinium nucleus.

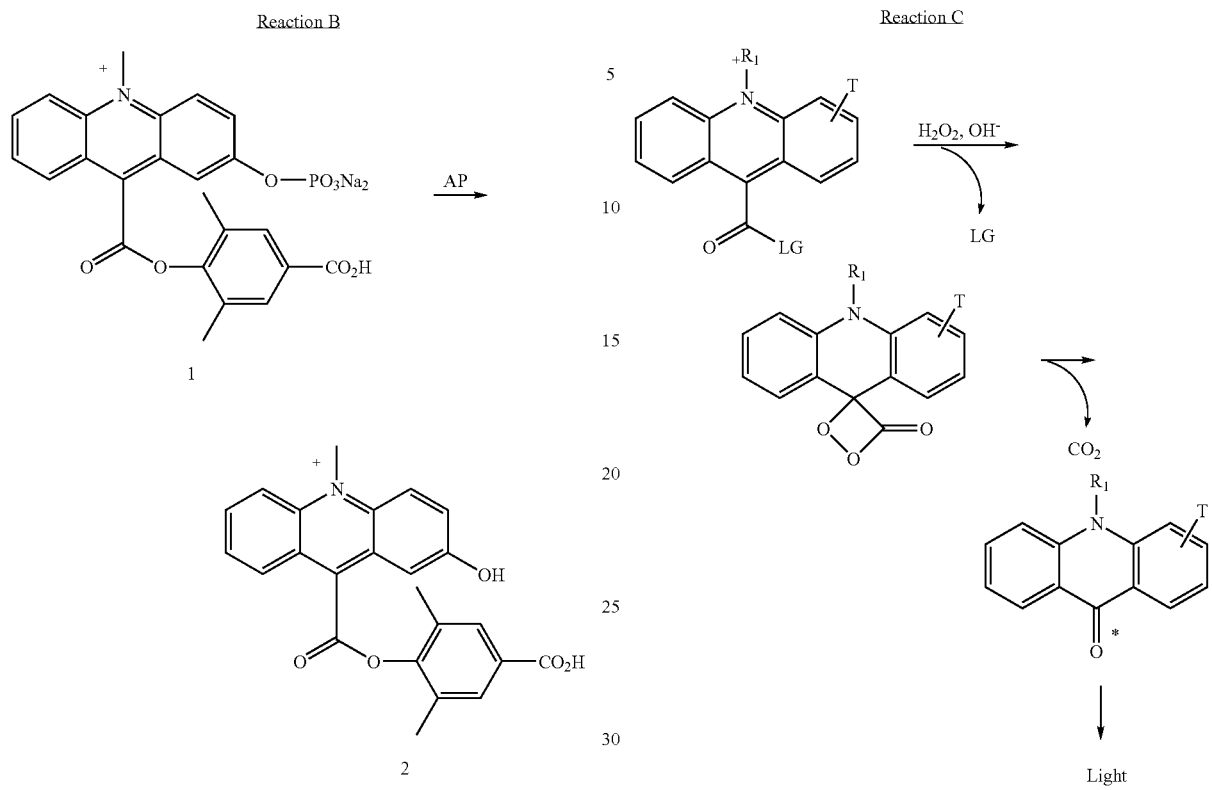

As illustrated in Reaction C, the chemiluminescent reaction of the acridinium compound is triggered by hydrogen peroxide in strong alkaline solution. Formation of the high energy dioxetanone follows the departure of the leaving group LG. The highly strained dioxetanone intermediate decomposes to the acridone, a portion of which is formed in an electronically excited state. When the excited acridone reverts to a ground state, light emission occurs. The emission wavelength is determined by the energy gap between the first excited state and the ground state, which in turn is determined by the specific structure of the acridone having various functional groups T. As disclosed in WO 00/09487, which is fully incorporated herein by reference, there are several factors which can influence the energy gap between the first excited state and the ground state of the acridone, and thus affect the emission wavelength. One of the factors is the direct attachment of the requisite functional group T to one of the peri-positions of the acridinium nucleus. It has been discovered and disclosed in the aforementioned WO 00/09487 that when a hydroxyl group is placed at the (2) or (7) position, such as in 2-OH-DMAE (2), the compound emits light at λmax 604 nm in strong alkaline solution. This is because in a strong alkaline solution, the hydroxyl group becomes deprotonated, and the resulting negatively-charged oxy anion exerts a strong electron donating effect to the acridinium nucleus, consequently decreasing the energy gap between the first excited state and the ground state of the acridone, which causes a bathochromic shift of light emission to 602 nm from 430 nm of the unsubstituted acridinium compound.

In this invention, a phosphoryloxy group at the (2) position of 1 serves as a masked hydroxyl group. This phosphoryloxy group is thermally and hydrolytically stable in aqueous medium with a wide range of pHs where virtually all hydrolytic enzymatic reactions take place. It is also stable in a mixture of hydrogen peroxide and strong alkaline solution for a length of time that is needed for converting acridinium compounds to the light emitting acridones. Because the phosphoryloxy group in 1 is virtually intact in the absence of hydrolytic enzyme during the reaction and also stable to hydrogen peroxide and strong alkaline solution, the electron-donating effect of the directly attached oxygen at the (2) position towards the acridinium nucleus is significantly diminished. Thus, no bathochromic shift of emission wavelength occurs. This is in sharp contrast to the situation of 2-OH-DMAE (2), the product of the reaction in the presence of hydrolytic enzyme. In the latter case, the hydroxyl group at the (2) position is ionized to a negatively-charged oxy anion, which has a strong electron donating effect to the acridinium nucleus, thus causing a significant bathochromic shift of emission wavelength.

It would be desirable that in a system using 1 as a chemiluminescent substrate, a specific hydrolytic enzyme such as AP that is either used as a label or present as a marker of a biomolecule converts a short wavelength emitting 1 to a long wavelength emitting 2. Indeed, upon treatment with hydrogen peroxide and strong alkaline solution, the reaction mixture containing both 1 and 2 produces a mixture of light signals each with its own maximum at 478 nm and 602 nm, respectively. The decrease in the short signal (λmax 478 nm) or the increase in the long signal (λmax 602 nm) directly correlates to the amount of the enzyme.

Another preferred compound selected from Formula VII is 2-Phos-7-MeO-DMAE (9). Unexpectedly, the dephosphorylated product, 2-OH-7-MeO-DMAE (10) in Reaction D was found to have 60–70 nm longer emission maxima than the unmethoxylated compound 2 (2-OH-DMAE), while both of the corresponding 2-phosporylated forms have nearly the same light emission maxima. Thus, the 2-Phos-7-MeO-DMAE and 2-OH-7-MeO-DMAE pair of chemiluminescent substrate and product provide effectively further improved distinction in light emission wavelength. The discovery has led to another preferred set of acridinium-based chemiluminescent substrates, wherein the Formula VII is further defined as above, except the substituents of $R_{3c}$ can be any electron-donating group such as hydroxy, thiol, amino, monoalkylamino, dialkylamino, alkoxy or thioalkyl. The presence of this second electron-donating group further decreases the energy gap between the electronically-excited and ground states of the light-emitting acridone. Consequently, a further red-shift in light emission is observed compared to 2-hydroxy-DMAE. This shift also results in increased spectral distinction of the blue and red-emitting acridinium ester pair.

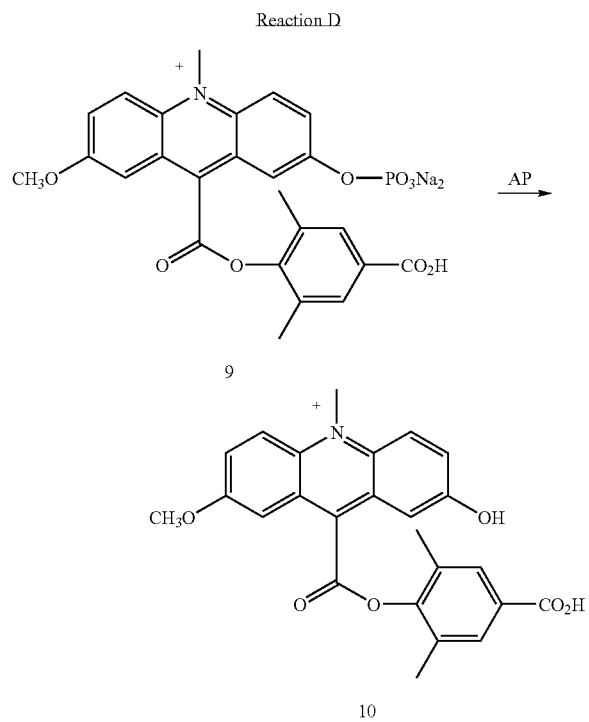

One of the modes of enzyme detection disclosed in this invention is to detect long wavelength signal of the product (2) that arises from enzymatic action. The commonly used methods for light detection include the use of a luminometer, a CCD camera, X-ray film, and a high speed photographic film. Since the hydrolytic enzyme to be detected often exists in a small quantity in the sample, the amount of the product that is generated by the enzyme is relatively small in comparison with the amount of the substrate used in the reaction. Therefore, it is critical to be able to detect such a small amount of this signal in the presence of a strong signal of the substrate.

Figure 3:
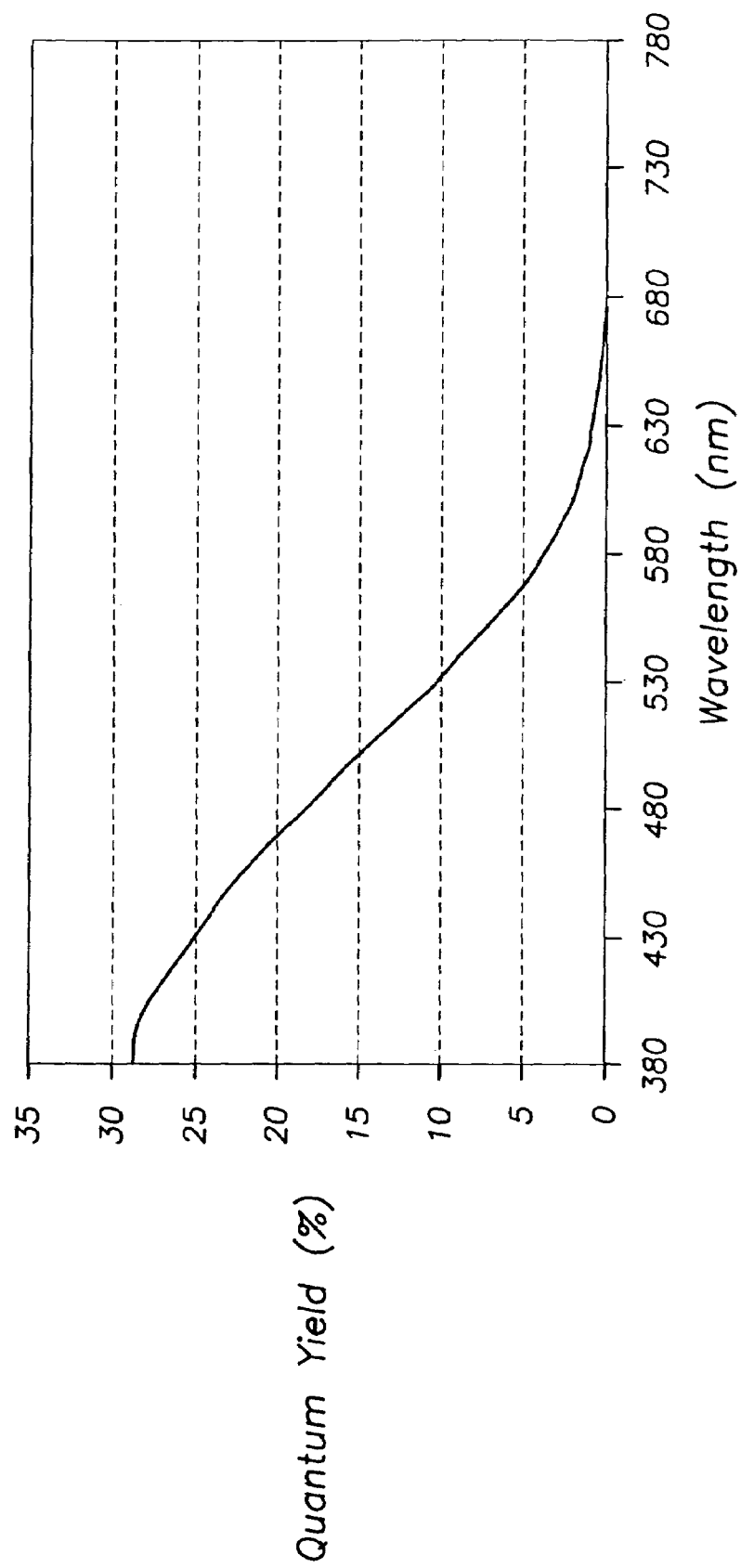
FIG. 3 is a plot of wavelength vs. quantum yield of Hamamatsu photomultiplier tube R268.
Figure 4:
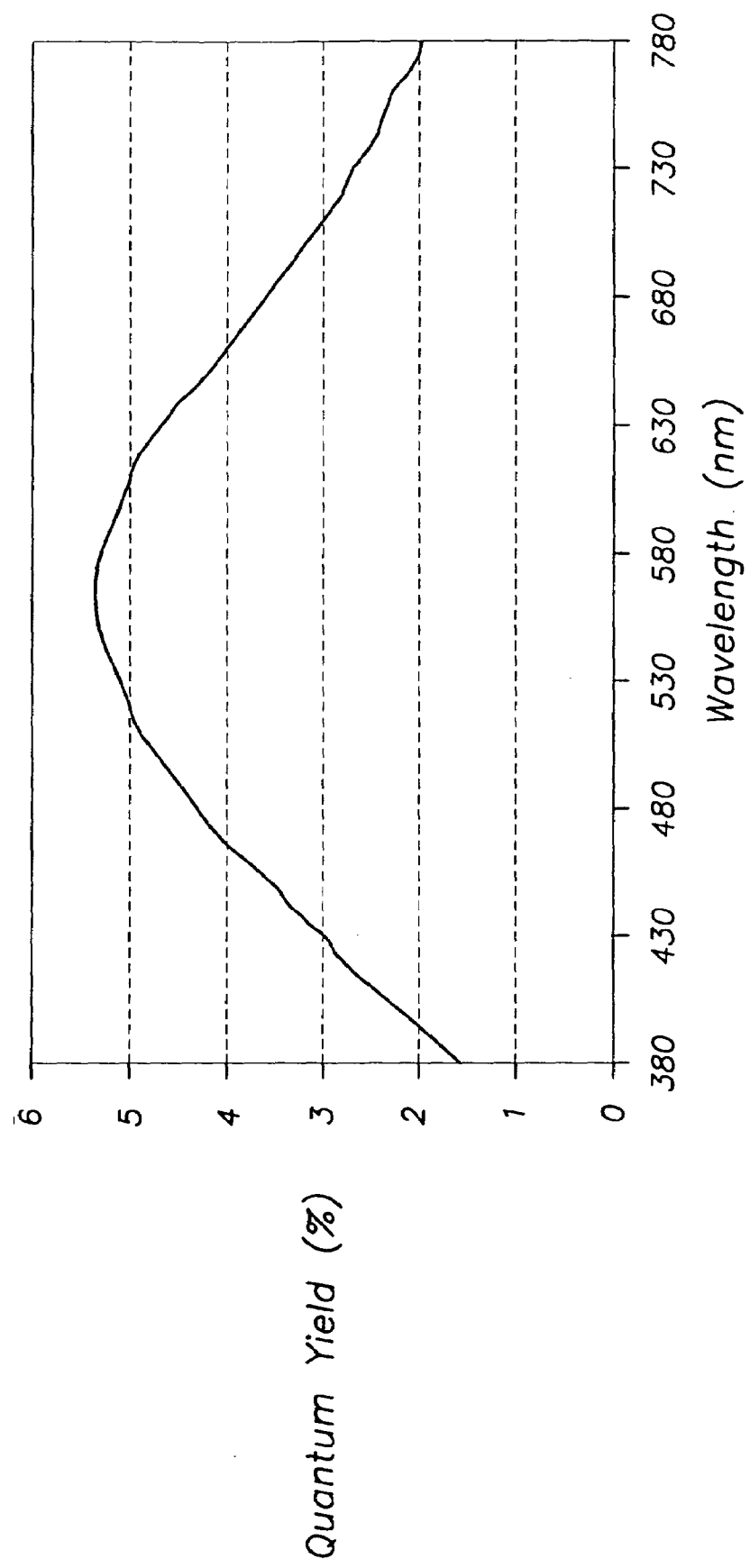
FIG. 4 is a plot of wavelength vs. quantum yield of Hamamatsu photomultiplier tube R2228P.

One important aspect of this invention related to detecting a long wavelength emission signal of the product such as 2 produced by a hydrolytic enzyme is the use of a luminometer having a red-sensitive photomultiplier tube (PMT). (Frequently, this type of PMT is cooled during use in order to reduce system noise.) The most commonly used commercial photomultiplier tubes are made from low dark count bialkali material. It has an excellent quantum yield in the short wavelength region but a very low quantum yield in the long wavelength region. For example, bialkali PMT model R268 from Hamamatsu has a quantum yield of about 22% in the range of 400–500 nm and only ~2% at 600 nm and above, which is not desirable for this specific application. On the other hand, PMT made from multialkali material is relatively more red-sensitive than that made from bialkali material. For instance, multialkali PMT model R2228 from Hamamatu has a quantum yield of 3~5% over the region of 400 to 500 nm, and a quantum yield of ~5% around 600 nm, which is more desirable for this application. The drawback of this PMT is a high dark count, and therefore it has to operate at low temperatures in order to suppress the dark count. FIGS. 3 and 4 show quantum efficiencies of PMTs of bialkali R268 and multialkali R2228P, respectively.

Figure 5:
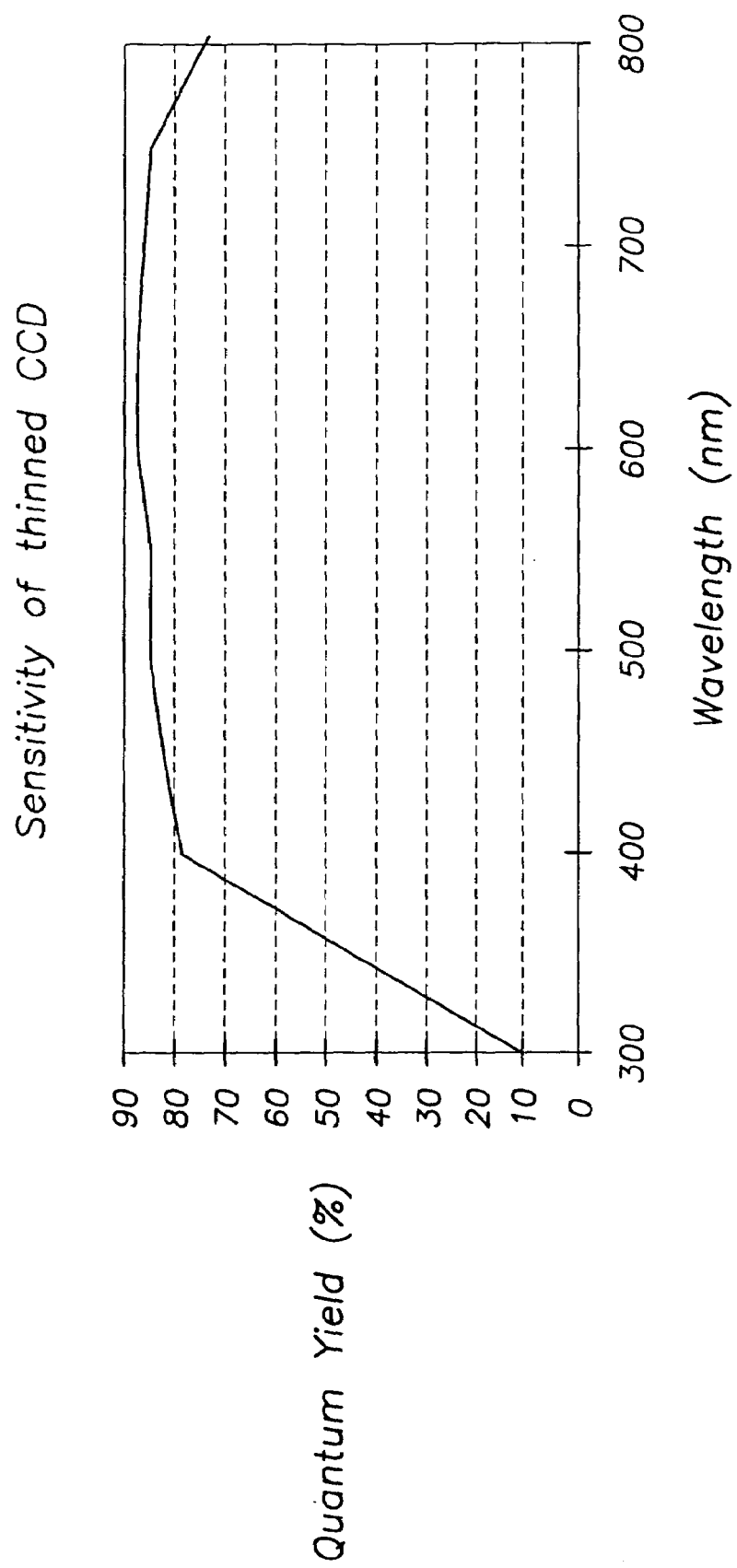
FIG. 5 is a plot of wavelength vs. quantum yield of the thinned, back-illuminated Charge Couple Device (thinned CCD).

Another useful aspect of this invention related to detecting a long wavelength emission signal of the product is the use of a charge-coupled device (CCD) camera, particularly a thinned, back-illuminated cooled CCD. As shown in FIG. 5, said CCD has a ~80% quantum efficiency at 400 nm and ~90% at 700 nm, thus capable of increasing the detectability of long wavelength emission (>550 nm) signal by 10–20 times or more over R268.

Figure 6:
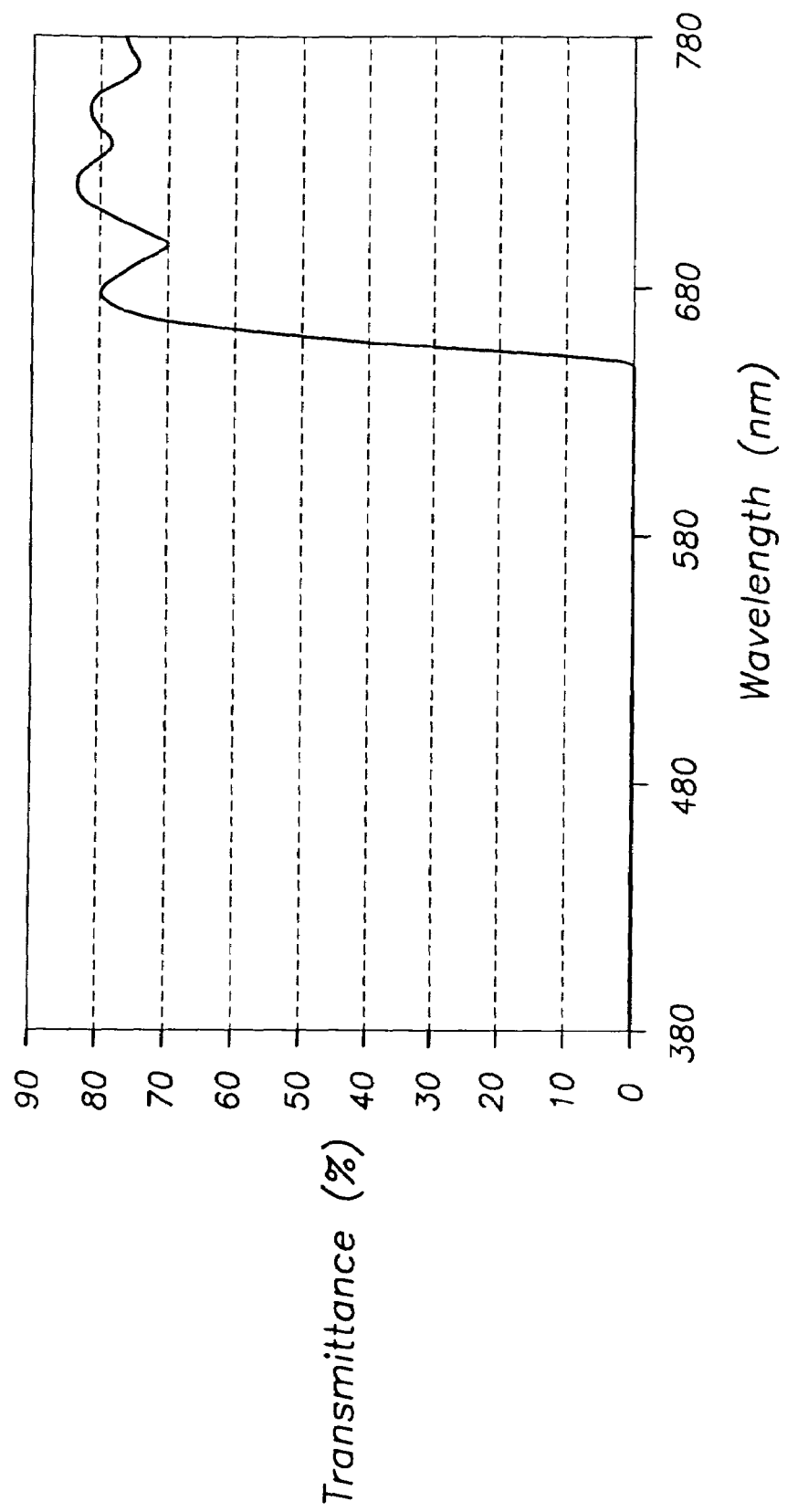
FIG. 6 is a profile of the transmittance of Corion cut-on long wave pass filter LL650 (Lot No. CFS-002645).
Figure 7:
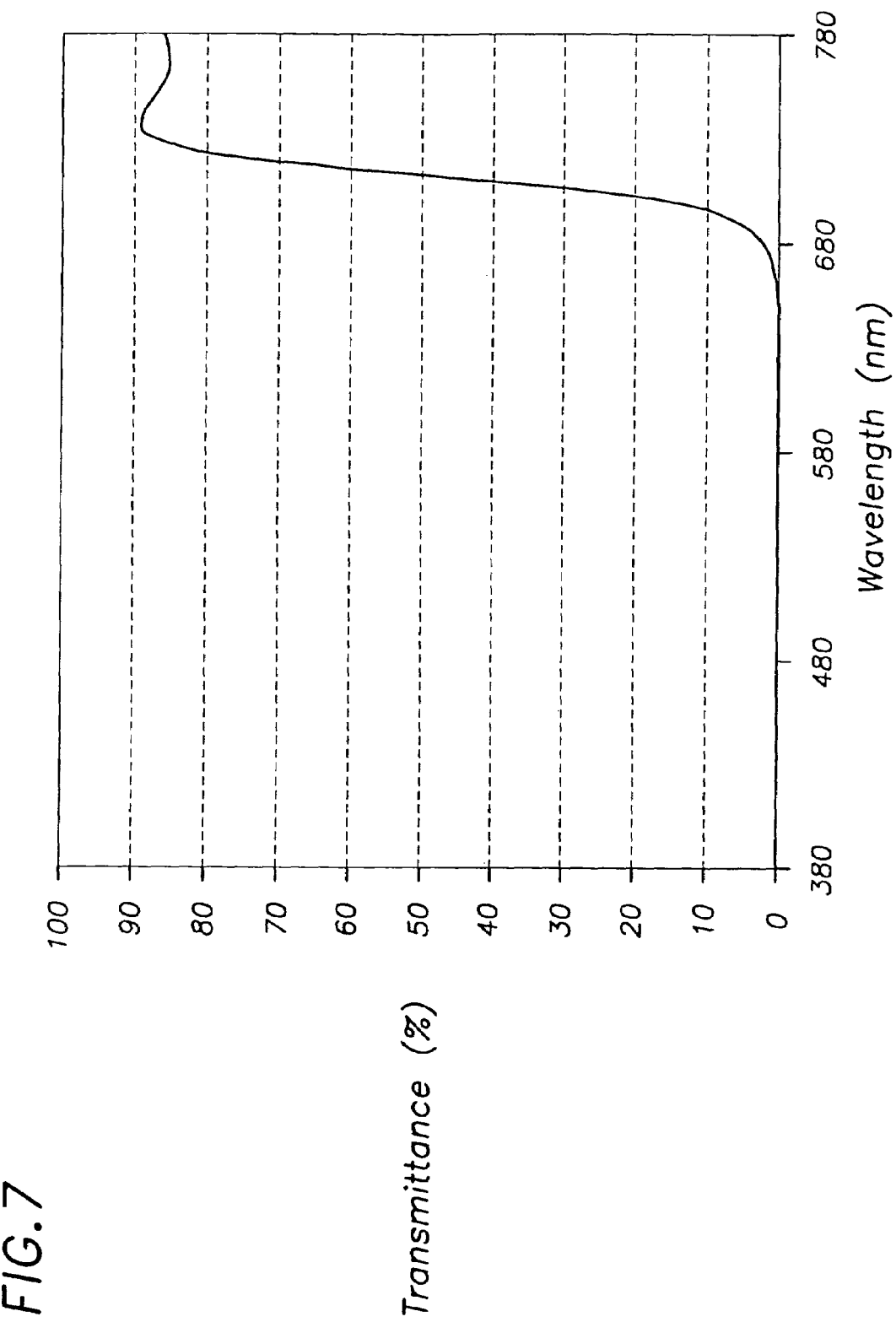
FIG. 7 is a profile of the transmittance of Corion long wave pass filter LL700.

Since both the substrates and products of the present invention are chemiluminescent, an essential aspect of this invention related to detecting a long wavelength emission signal of 2 is the use of a filtering device to block the short wavelength signal from 1. FIGS. 6 and 7 show transmittances of Corion LL700 and LL650 long wave pass filters (Corion, Franklin, MA), respectively.

Figure 8:
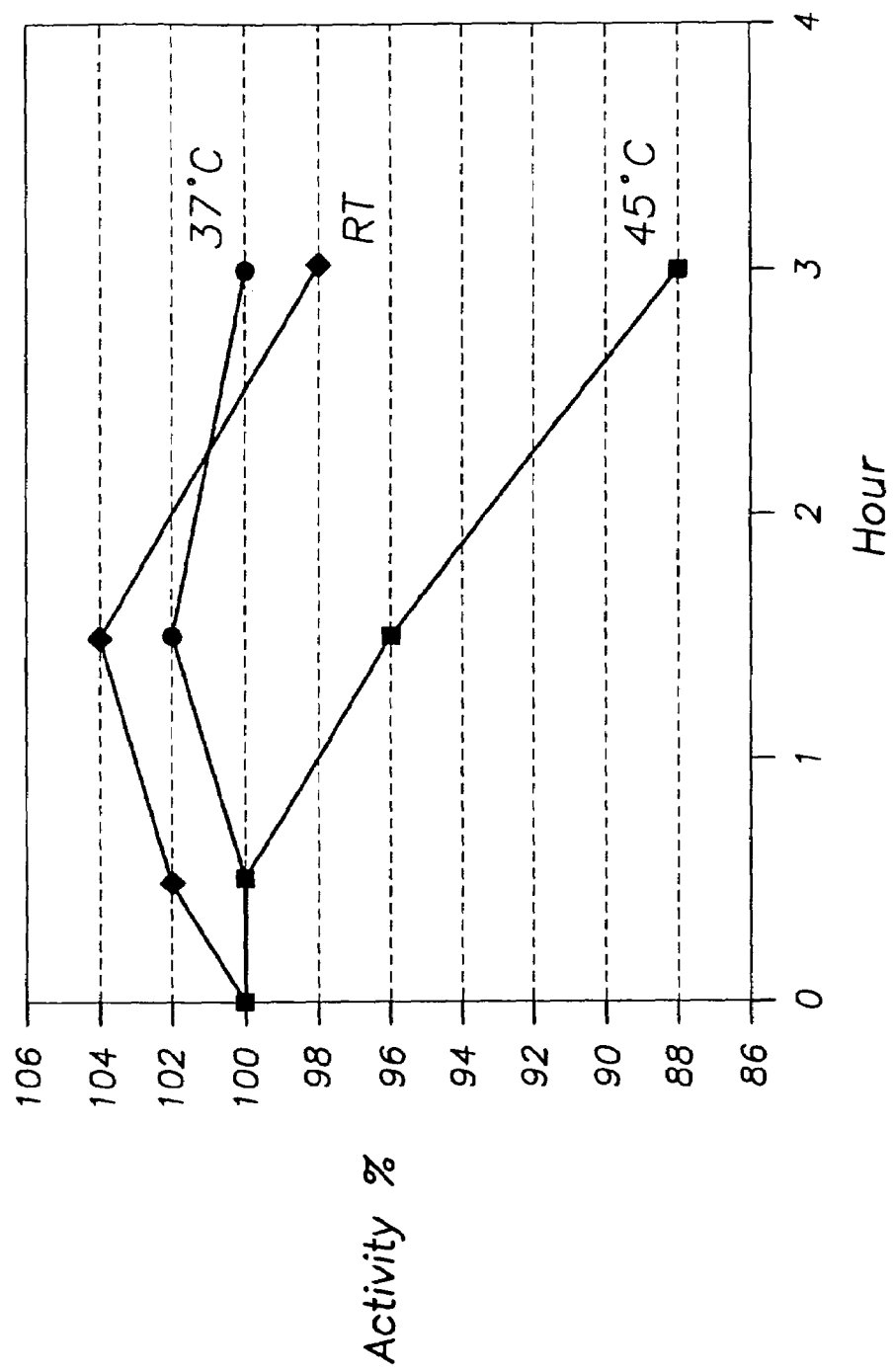
FIGS. 8 and 9 are plots of stabilities of chemiluminescent product (2-OH-DMAE) in pH 10.5, 100 mM Tris buffer containing 1 mM $MgCl_2$ as a function of time.
Figure 9:
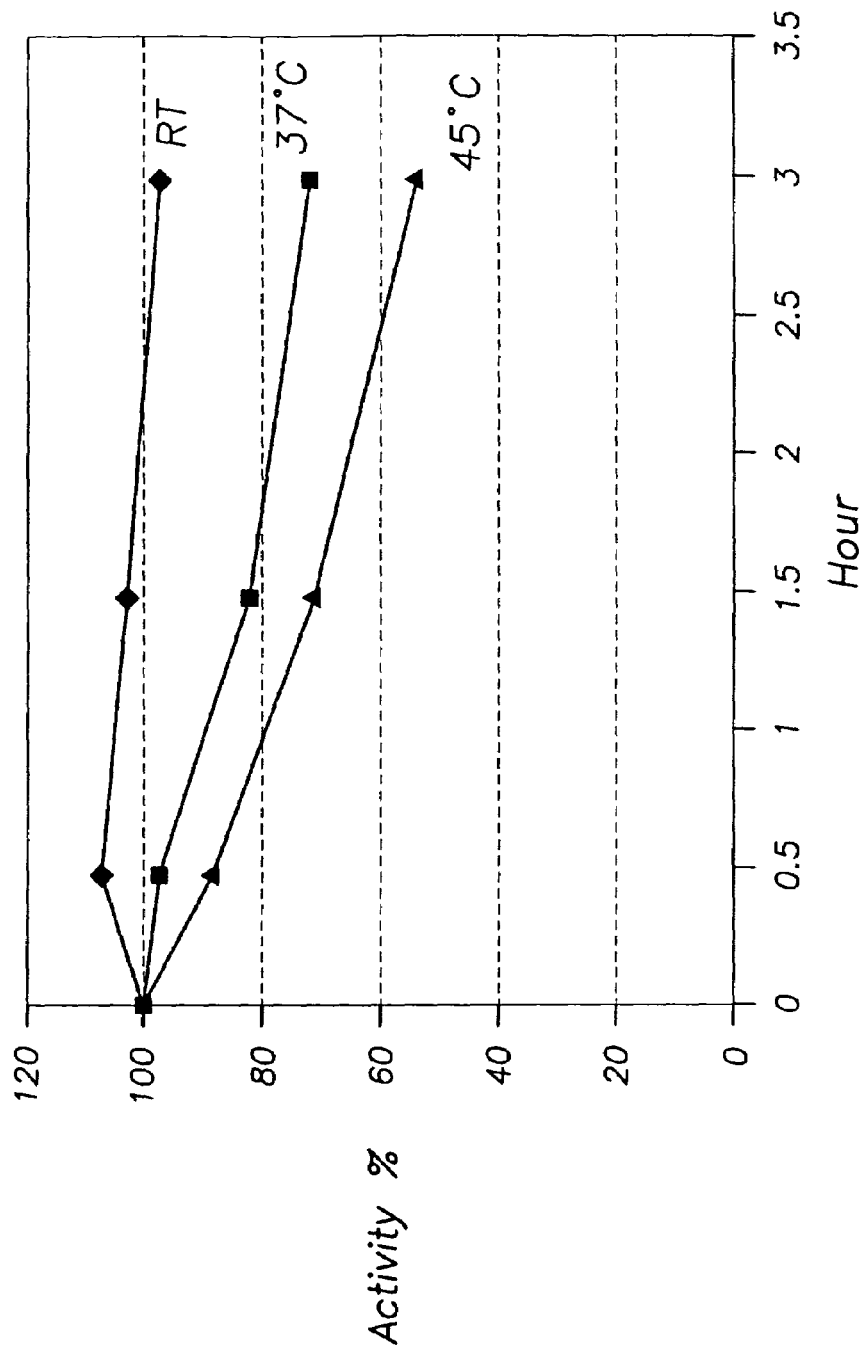

One of the advantages in using chemiluminescent acridinium substrates like 1 to detect hydrolytic enzymes is that the products like 2 generated by the enzyme can be accumulated without undergoing significant decomposition during the enzymatic reaction. FIGS. 8 and 9 show the stability of 2-OH-DMAE (2) in aqueous medium at pHs 9 and 10.5 and at different elevated temperatures.

The sensitivity relating to the detection of a long emission signal of the product generated by a hydrolytic enzyme is largely dependent on the signal differentiation of the product (2) and the substrate (1). It is therefore desirable to reduce background emission of the substrate 2-Phos-DMAE in order to obtain a sensitive system. The generation of light from acridinium compounds is traditionally made by the treatment with acidic hydrogen peroxide solution first, followed by an alkaline surfactant solution. The purpose of the acid is to convert the pseudo-form of acridinium compound to the quaternary form and the surfactant aids in enhancing the quantum yield of the acridinium compound. Preferably, said acidic hydrogen peroxide solution contains hydrogen peroxide at concentration of 0.001 to 5%, and nitric acid at concentration of 0.001 to 1.0 N, and said alkaline surfactant solution contains sodium hydroxide at concentration of 0.01 to 1 N, and AQUARD (CTAB) at 0.01 to 1%. More preferably, said acidic hydrogen peroxide solution contains 0.5% hydrogen peroxide and 0.1 N nitric acid, and said alkaline surfactant solution contains 0.25 N sodium hydroxide and 0.5% AQUARD (CTAB).

An unexpected finding, to the advantage of detecting the long wavelength emission signal from 2, is that under certain conditions the chemiluminescence from 1 is selectively and significantly suppressed, and thereby the overall signal differentiation of 2 over 1 is improved. Specifically, the chemiluminescence of 1 is significantly lowered if the solution is treated with an alkaline solution first and then with hydrogen peroxide solution. More specifically, when a solution of 1 is treated with 0.25 N sodium hydroxide solution containing 0.5% AQUARD, followed by 0.5% hydrogen peroxide, the quantum yield of 1 is lowered by more than 30 fold. In contrast, under the same condition the quantum yield of 2 is basically not affected. This results in an overall improvement of the signal differentiation by 30 fold. Thus, to the advantage of better distinction between the signals of certain chemiluminescent products and their substrates, preferably, said alkaline solution contains sodium hydroxide at concentration of 0.01 to 1.0 N, and AQUARD at concentration of 0.01 to 1%, and said hydrogen peroxide solution contains hydrogen peroxide at concentration of 0.001 to 5%. More preferably, said alkaline solution contains 0.25 N sodium hydroxide and 0.5% AQUARD, and said hydrogen peroxide solution contains 0.5% hydrogen peroxide.

Figure 10:
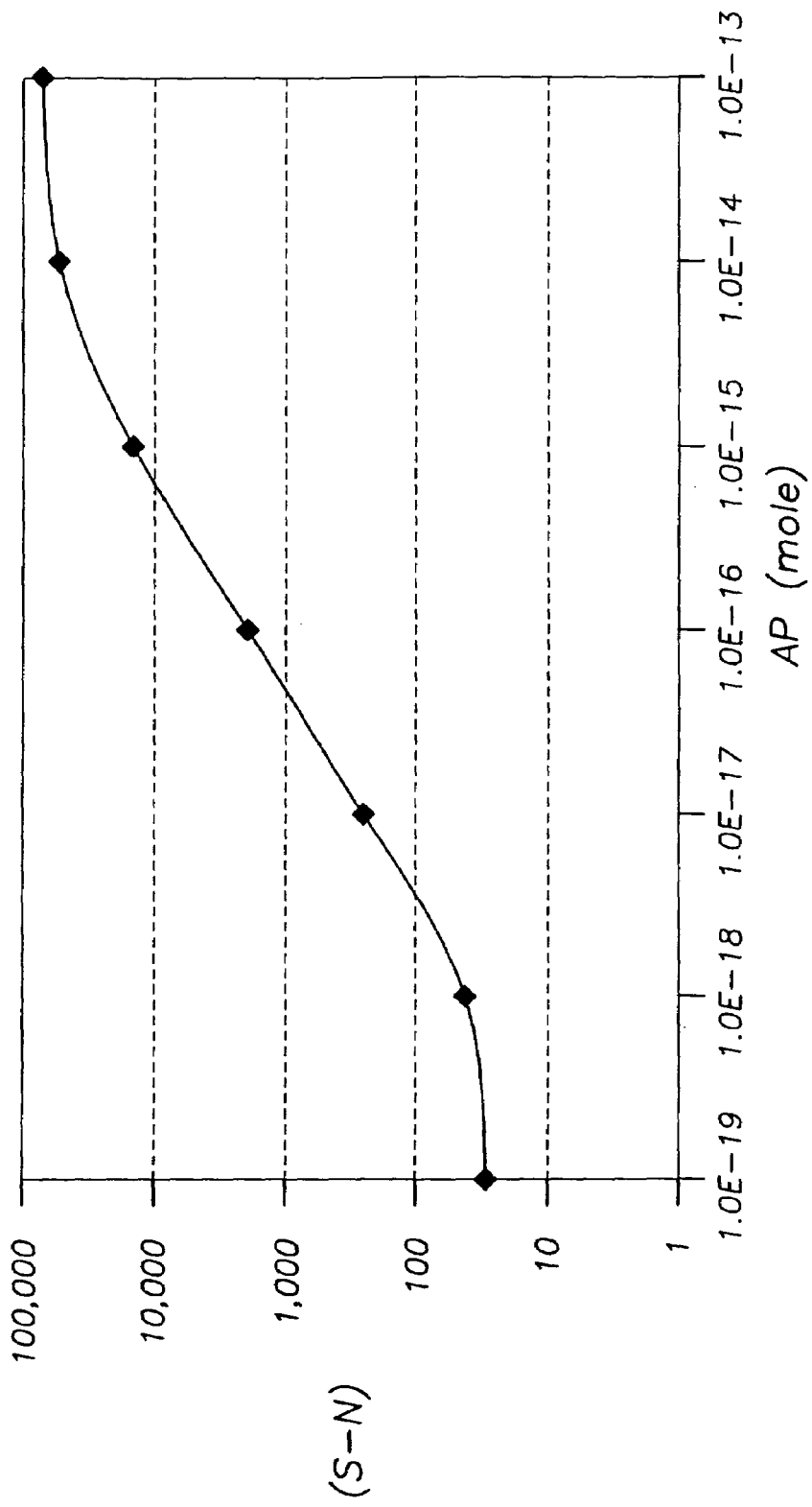
FIG. 10 is a plot showing the detectability of alkaline phosphatase using 2-Phos-DMAE as the substrate. The enzyme reaction was incubated at 45° C. for 0.5 hour. The reaction mixture was flashed with 0.25 N NaOH containing 0.5% CTAB immediately followed by 0.5% $H_2O_2$. The light output was measured for 2 seconds on MLA-1 equipped with R268 PMT and two LL650 long wave pass filters.
Figure 11:
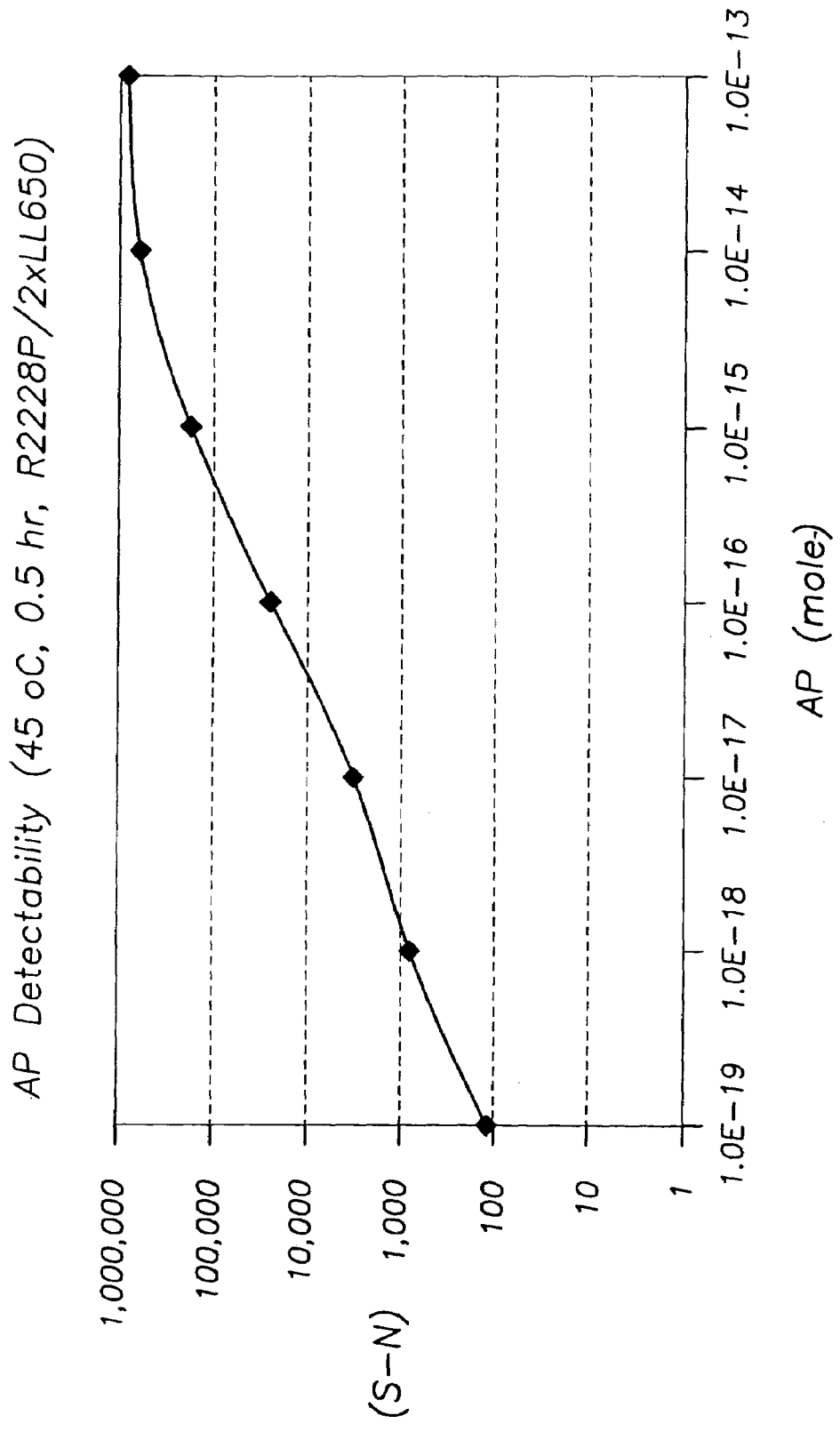
FIG. 11 is a plot showing the detectability of alkaline phosphatase under the same reaction condition as described in FIG. 10, with the exception that the light output was measured on MLA-1 equipped with R2228P PMT and two LL650 long wave pass filters, and the unit was pre-cooled to 4° C.
Figure 12:
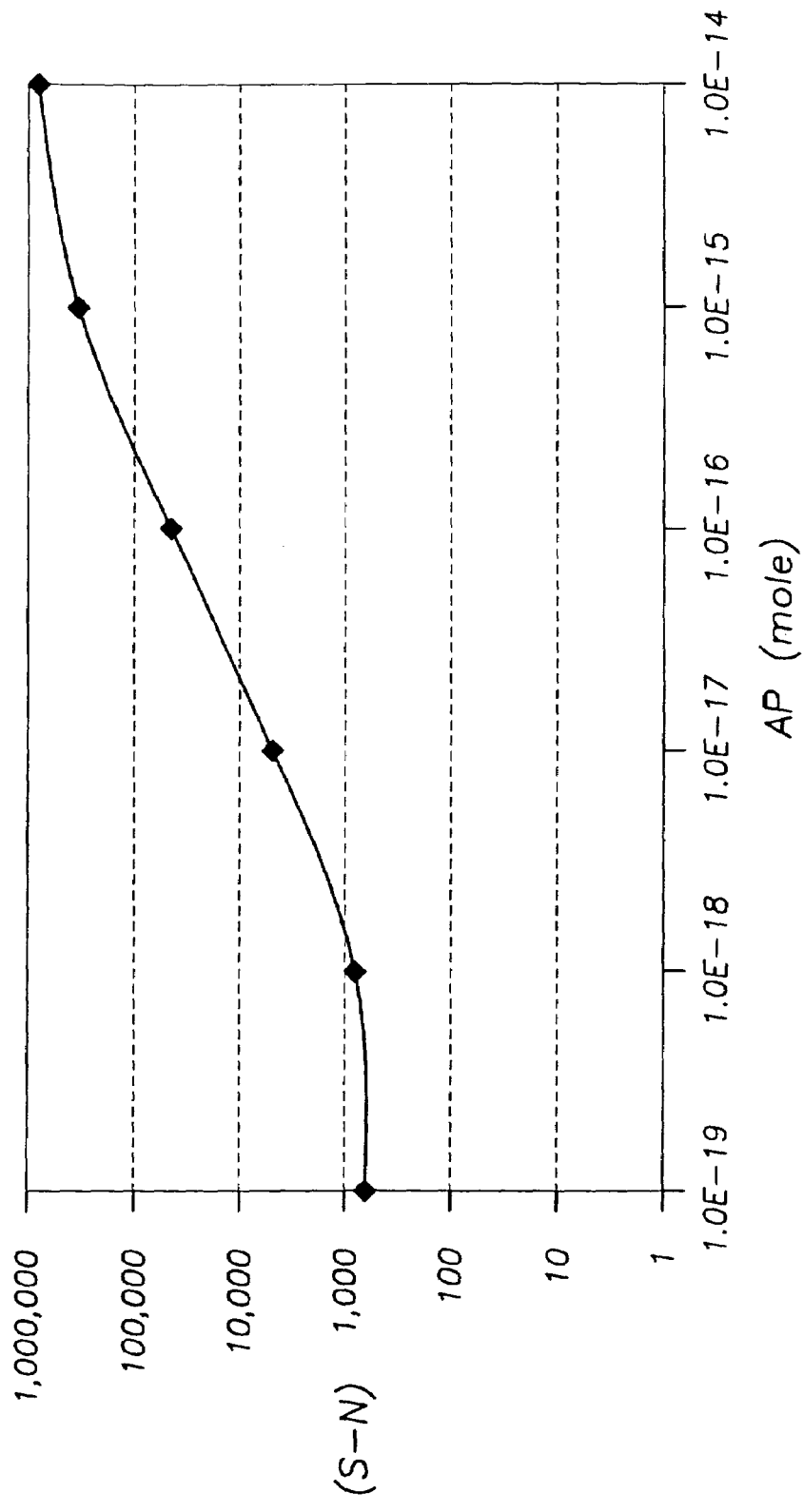
FIG. 12 is a plot showing the detectability of alkaline phosphatase using 2-Phos-DMAE as the substrate. The enzyme reaction was incubated at 45° C. for 1 hour. The reaction mixture was flashed with 0.25 N NaOH containing 0.5% CTAB immediately followed by 0.5% $H_2O_2$. The light output was measured for 2 seconds on MLA-1 equipped with R2228P PMT and a LL700 long wave pass filters, and the unit was pre-cooled to 4° C.

With one or more of the above approaches combined, several assay systems based on the principle of detecting the long emission signal generated by the action of AP on 2-Phos-DMAE (1) are constructed, and disclosed in the section of Examples. One example (Example 17) consists of the incubation of AP standards in a substrate solution containing 0.1 mM 2-Phos-DMAE (1), 1 mM magnesium chloride in 100 mM, pH 9 Tris buffer at 45° C. for 1 hour. The light outputs were measured on a luminometer equipped with a red-sensitive PMT (R2228P) and a long pass filter (LL700), which is placed in a 4° C. cold room. The sample was treated first with 0.25 N sodium hydroxide solution containing 0.5% AQUARD, immediately followed by 0.5% hydrogen peroxide. As shown in FIG. 12, AP is detected at a level below 1×10–18 mole. Another example under the similar condition is given in Example 16 and the result is shown in FIGS. 10 and 11.

Another important method for selectively reducing background of 2-Phos-DMAE (1) is through a selective quenching. Selective quenching, herein and hereafter, refers to the use of one or more compounds or chemical moieties to selectively reduce chemiluminescence of the substrate such as 1 via the mechanism of energy transfer. Referring back to Scheme III, the energy of the excited acridone (donor) resulting from the chemiluminescent reaction of the acridinium compound can be transferred to an adjacent, non-fluorescent molecule (acceptor or quencher). This non-fluorescent molecule reverts to the ground state via a non-radiative pathway to release the energy. The quantum yield of the acridinium compound is quenched or reduced as the result of the quenching. The effectiveness of the quenching depends on the distance, spectral overlap and transition dipole-dipole interaction of the acridinium compound and the quencher. First, the acridinium compound and quencher must be in a close vicinity, preferably at a distance less than 10 nm in order to achieve 20~100% quenching effect, since the effectiveness of energy transfer is inversely proportional to the sixth power of the distance between the donor and acceptor. Secondly, the UV absorption spectrum of the quencher must overlap, at least partially, with the emission spectrum of the acridinium compound. Lastly, even though it is often not easy to control the spatial conformations of the two concerned molecules in order to obtain the effective transition dipole-dipole interaction, a relatively free movement of two spatially close molecules often fulfil this requirement.

There are in general two ways of quenching, intermolecular and intramolecular. Specifically related to this invention, the intermolecular quenching refers to when the quencher and acridinium compound coexist in the same solution, but the two molecules are not linked together. The intramolecular quenching refers to when both the quencher and acridinium compound are covalently linked in one molecule. In the case of intermolecular quenching, the effectiveness of the quenching depends on the concentration of the quencher relative to the concentration of acridinium compound. The concentration of the quencher or substrate or both must be in the range of millimolar in order to achieve effective quenching. However, for the intramolecular quenching, the effectiveness of the quenching is determined by a bonding distance between the two molecules, and that in turn can be warranted by the proper selection of the length of the tether that connects the two.

Another aspect closely related to the selection of a quencher is that the quencher should only selectively or preferentially quench light of 2-Phos-DMAE (1) and have little or no effect on the light emission of 2-OH-DMAE (2). To achieve this, the UV absorption spectrum of the quencher should have a maximum overlap with emission spectrum of 1 but a minimum overlap, or preferably no overlap at all, with emission spectrum of 2. The other criteria for an effective quencher for this application include a large molar extinction coefficient and adequate water solubility. Examples of compounds that are suitable to serve as quenchers are given below, but are not limited to those listed.

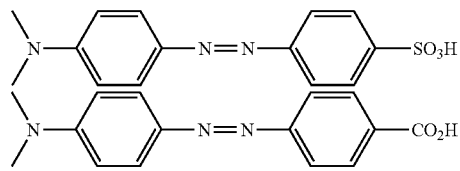

It is an intention of this invention to provide, but not limiting to, one mechanism to selectively reduce the light emission of the substrate via selective quenching. It is understandable that any other approach or mechanism capable of selectively reducing the quantum yield of the chemiluminescent substrates will also fall in the scope of this invention.

The second mode of light detection involves detecting the short emission signal of the substrate (1) that diminishes as the result of the action of enzymatic action. This mode of detection takes advantage of the high quantum yield of bialkali, blue-sensitive PMTs as discussed earlier. In connection with the use of a blue-sensitive PMT, a filtering device that is capable of blocking a long emission signal must be also used in order to block long-wavelength light emission of the product in the hydrolytic enzymatic reaction.

Belonging to Formula II, another important sub-class of chemiluminescent substrates related to this invention are substrates capable of "reverse emission", where Lumi-M-P is capable of emitting long-wavelength light while the product (Lumi-M) is capable of emitting short-wavelength light. One major advantage in this reverse emission mode is that the product is detected at a short emission signal with bialkali, blue-sensitive PMT fitted with a short wave pass filter, where quantum yield of the PMT is as high as 22%.

Chemiluminescent substrates capable of the reverse emission are represented by Formula II where M-P is replaced by Formula X:

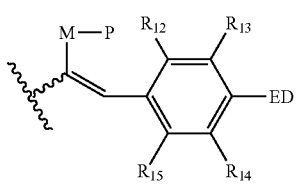

Formula X

As provided in Formula X, preferably M and P are defined in Formula II. ED is an electron-donating group, preferably an ionizable group, which donates an electron pair to the conjugated system and is selected from hydroxyl, —OR, —NR'R", thiol (—SH), —SR, and —CHWn where n=1 or 2, W is an electron withdrawing group including, but not limited to, nitro, nitroso, cyano (—CN), —CHO, —C(O)R, —N$^+$RR'R", —CO$_2$H, —CO$_2$R, —S(O)R, —SO$_2$R, —SO$_2$OR, —SO$_2$NHR, —SO$_2$NR'R"-SO$_3$H, or F, where R is defined in Formula II, R' and R" are hydrogen or low alkyl, and R, R' and R" can all be the same or different. ED is interchangeable with $R_{12}$ or $R_{15}$.

$R_{12}$, $R_{13}$, $R_{14}$ and $R_{15}$ may be identical or different, and are selected from hydrogen, —R, hydroxyl, amino, halides, nitro, nitroso, sulfonate, sulfate, phosphonate, —CO$_2$H, cyano (—CN), —SCN, —OR, —SR, —SSR, —C(O)R, and —C(O)NHR, and R is defined in Formula II; alternatively, any adjacent two groups of $R_{12}$ to $R_{15}$ can form one or more additional fused hydrocarbon aromatic rings or heteroaromatic rings with or without substitutions, and the additional fused hydrocarbon aromatic rings and heteroaromatic rings include, but are not limited to, benzene, naphthlene, pyridine, thiophene, furan, and pyrrole, and so on.

Preferably, $R_{12}$, $R_{13}$, $R_{14}$ and $R_{15}$ are all hydrogen, and ED is hydroxy, and chemiluminescent substrates capable of reverse emission have Formula XI:

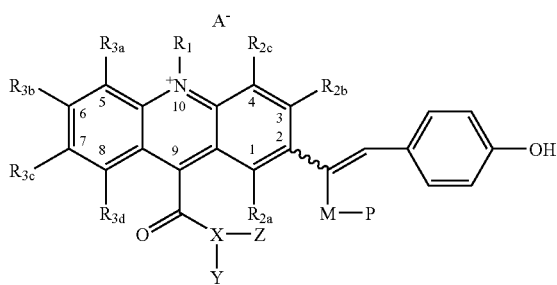

Formula XI

Alternatively, the group represented by Formula X can be located at the $C_3$ position of acridinium nucleus, having Formula XII below:

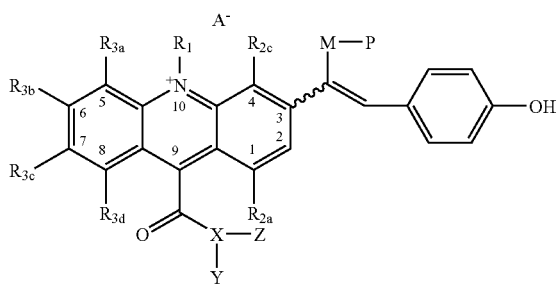

Formula XII

More preferably, in Formula XI and XII, M is oxygen; P is a phosphoryl group, —PO$_3$Na$_2$, where two sodium cations can be exchanged independently with hydrogen, potassium, magnesium, calcium, or other cationic ion(s) or group(s) for maintaining the eletroneutrality of the molecule; $R_{2a-c}$ and $R_{3a-d}$ are hydrogen, $R_1$ is methyl; X is oxygen, Z is omitted, and Y is a polysubstituted aryl moiety of Formula III where $R_4$ and $R_8$ are methyl, $R_5$ and $R_7$ are hydrogen, and $R_6$ is carboxyl (—CO$_2$H). One of the more preferred chemiluminescent substrate capable of reverse emission has structure 13. It is readily converted by alkaline phosphatase to its keto form (14).

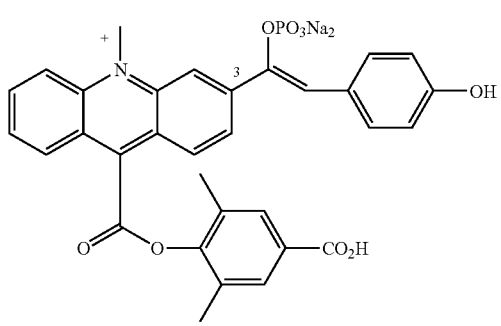

13

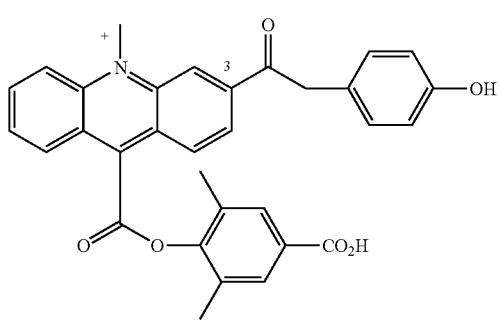

14

Another preferred chemiluminescent substrate capable of reverse emission is the reduced form of compound 13,

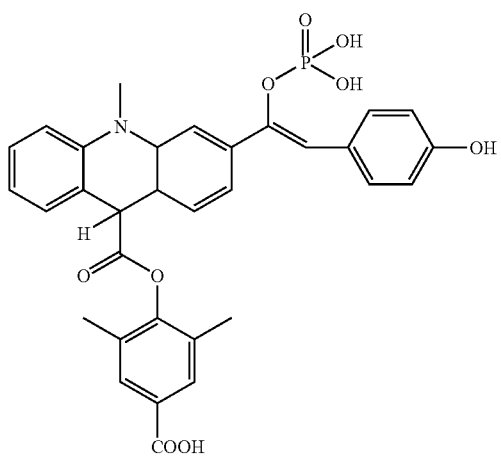

15

-continued

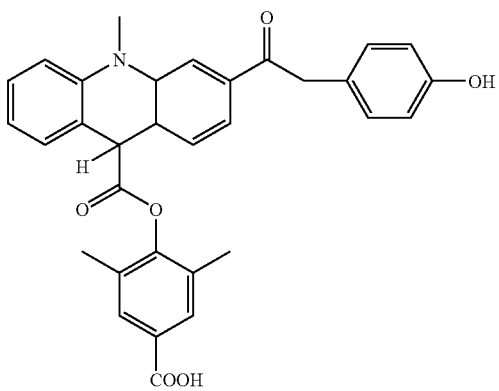

which is shown as 15. Similar to 13, compound 15 is also readily converted by alkaline phosphatase to its keto form (16).

Figure 2M:
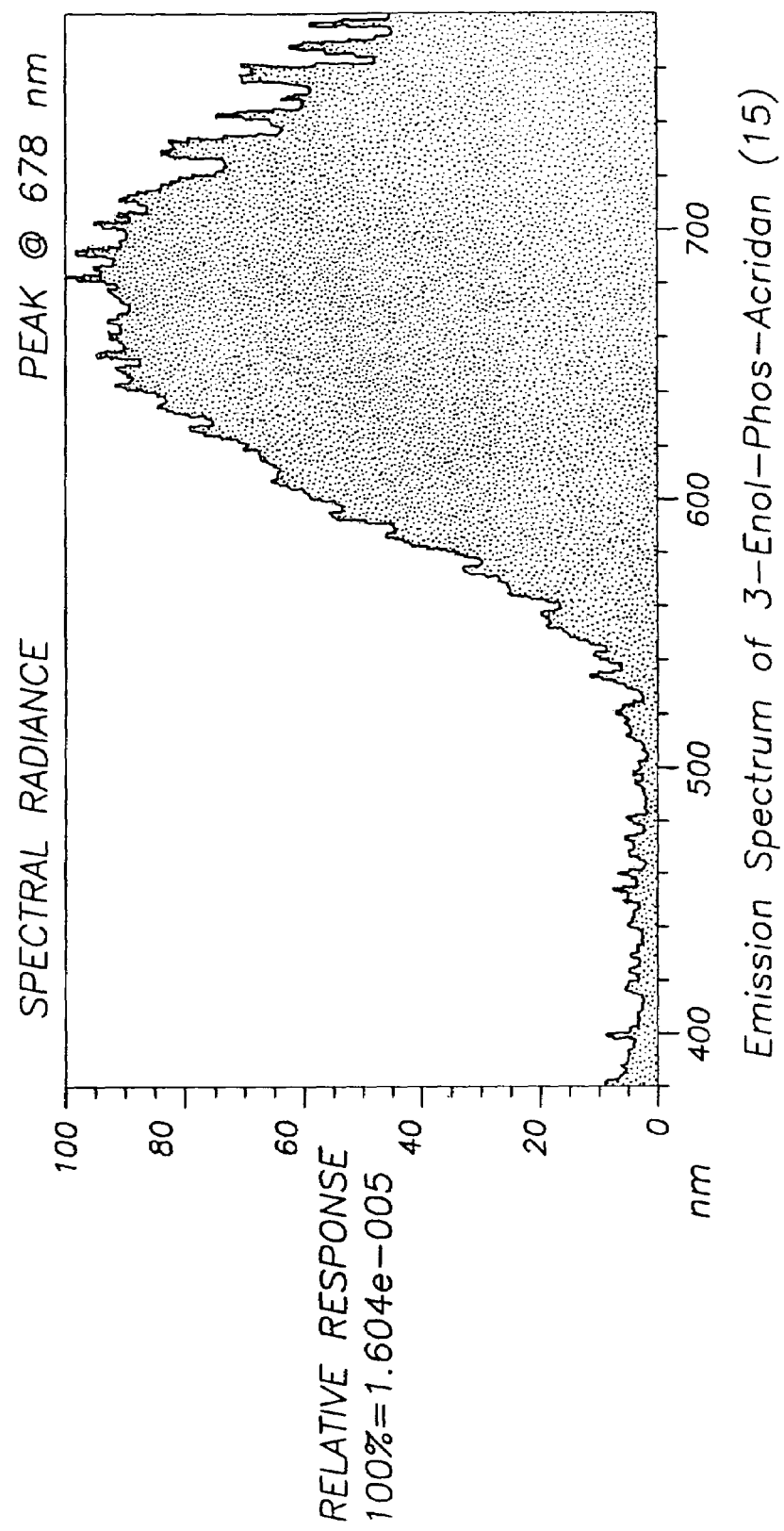
Figure 2N:
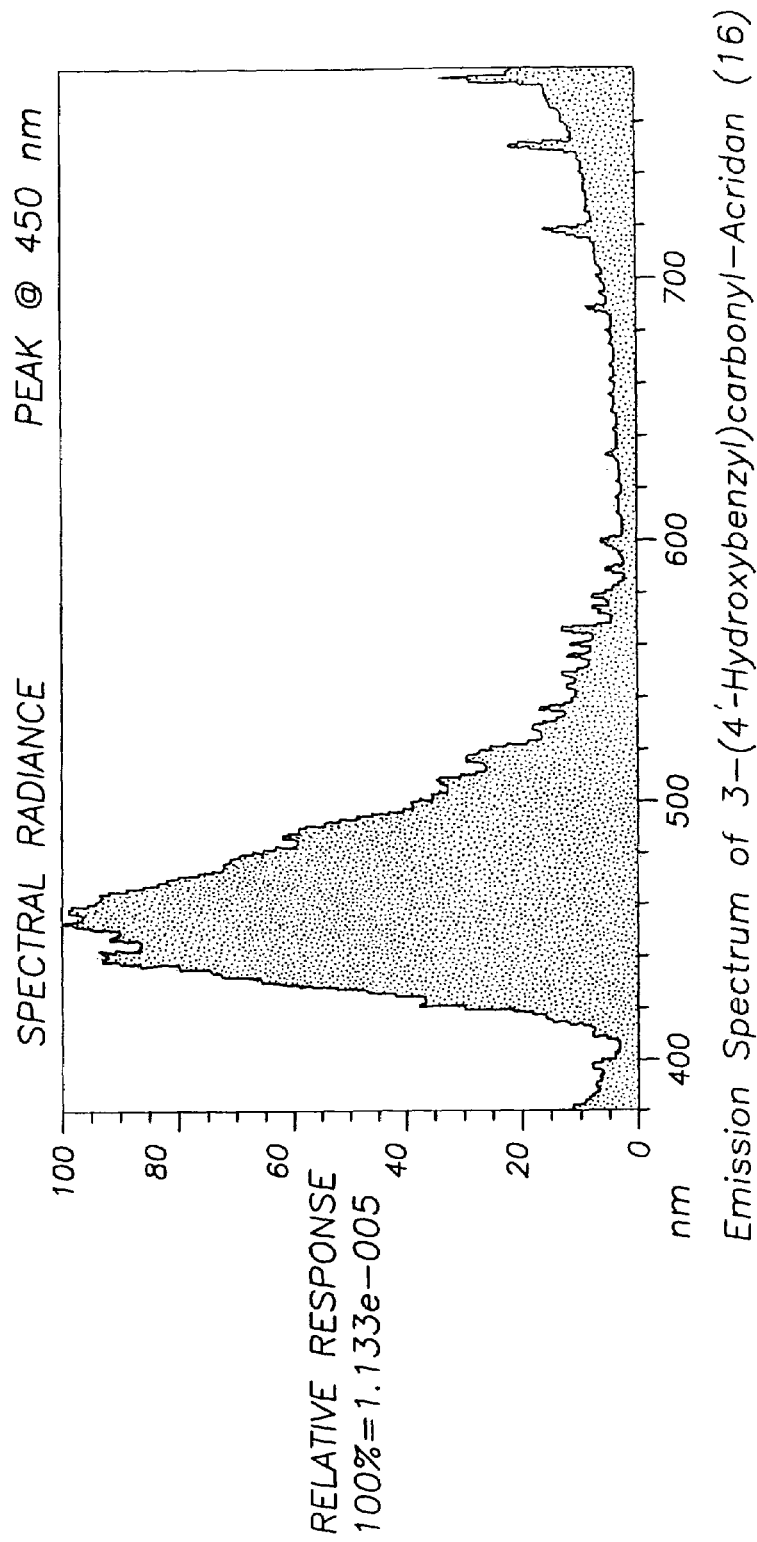
Figure 20:
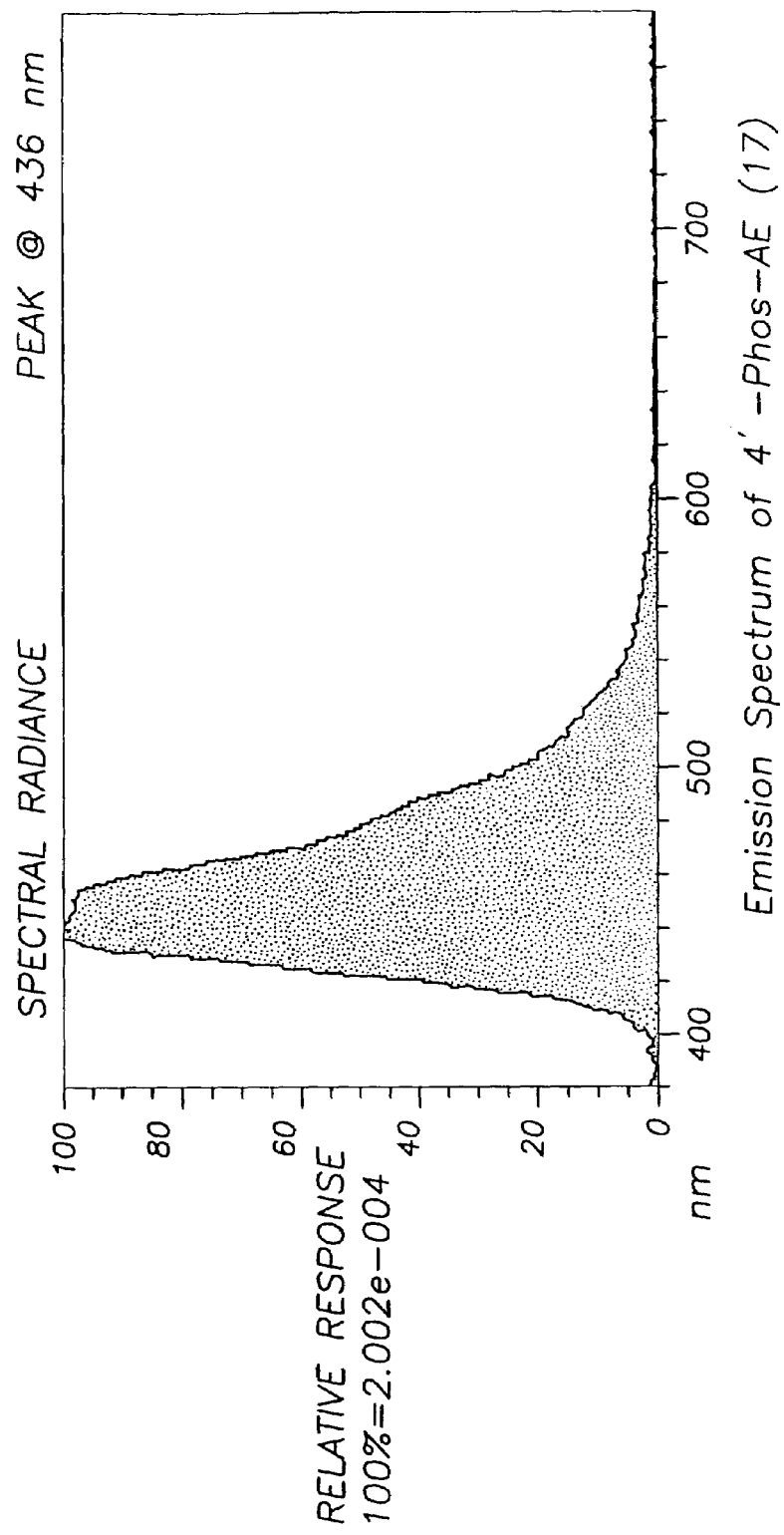

It has been unexpectedly discovered that both compounds 13 and 15 are capable of emitting light at extremely long wavelength. FIG. 2M is the emission spectrum of compound 15 determined by FFFS, showing that it emits light at λmax 678 nm. FIG. 2N is the emission spectrum of compound 16, which is the product of 15 after the treatment with AP. It shows that 16 emits light at λmax 450 nm, giving a net 228 nm of hypsochromic shift from 15.

Hypsochromic shift of emission wavelength due to a number of factors including solvent and chemical substitutional effects on the acridinium compounds has been disclosed in the co-pending WO 00/09487, which is included herein as reference. Distinguishably, one of the discoveries in this invention which relates to a large hypsochromic shift of emission wavelength from 13 to 14 and from 15 to 16 is due to the interruption of electronic conjugation between the acridinium nucleus and the electron-rich aromatic side chain caused by the enzymatic dephosphorylation.

2. Substrates and Products Having Different Emission Kinetics

In addition to spectral distinction as a means of discriminating chemiluminescent substrate from product, enzyme-mediated, alteration of acridinium-ester flash-kinetics is also an effective method to monitor and determine the concentration of the enzyme. This methodology thus provides an alternate 'readout' signal when the enzyme is used as the label in an assay. One approach to modulate acridinium ester light-emission kinetics is to alter the electronic properties of a suitable functional group located on the phenol, as shown in Reaction E. During the chemiluminescent reaction of acridinium esters, cleavage of the phenolic ester is a pre-requisite for formation of the dioxetanone precursor that is ultimately responsible for light emission. If the cleavage of this phenolic ester can be altered in a predictable way by making the phenol a better or poorer leaving group, then the kinetics of light emission from the corresponding acridinium ester can be modulated. For instance, an electron-donating group located ortho or para to the phenolic hydroxy moiety will render the phenol electron-rich, hence a poor leaving group. This will lead to slow light emission. Conversion of the electron-donating group to an electron-withdrawing group will accelerate cleavage of the phenolic ester and fast light emission will be obtained. The conversion of an electron-donating to an electron-withdrawing group or vice versa can be accomplished enzymatically. For instance, it is well known that oxidative enzymes such as peroxidases can oxidize electron-donating groups such as amino to electron-withdrawing groups such as nitroso or nitro groups. On the other hand, hydrolytic enzymes can convert an electron-withdrawing or neutral functional group to an electron-donating group. In this case the kinetics of light emission from an acridinium ester is slowed down by the enzyme label.

Reaction E

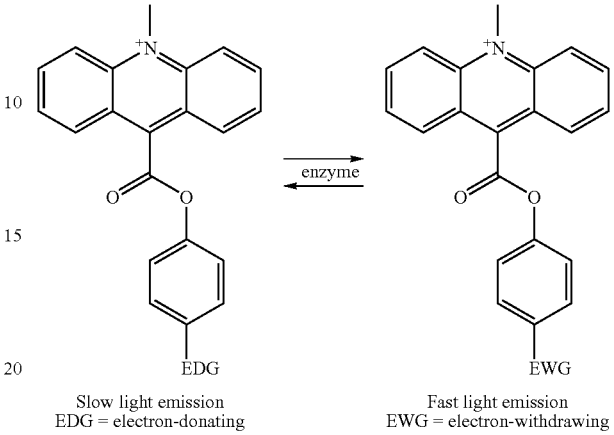

Slow light emission
EDG = electron-donating group

Fast light emission
EWG = electron-withdrawing group

Acridinium esters containing a 4'-hydroxy group on the phenol exhibit slow kinetics in their light emission upon reaction with hydrogen peroxide in strong alkaline solution. This is primarily because the phenol in the acridinium ester containing the 4'-hydroxy group is a poor leaving group. Conversion of this hydroxy group to a phosphate ester attenuates somewhat the electron donating ability of the 4'-oxygen substituent. Light emission from acridinium esters containing a 4'-phospho substituent is relatively faster than their 4'-hydroxy counterparts. Within this category are a subgroup of chemiluminescent acridinium substrates that are capable of emitting light at slower kinetics after the treatment with a hydrolytic enzyme, said subgroup of chemiluminescent acridinium substrates having Formula XIII. Wherein, $R_1$, $R_{2a-c}$, $R_{3a-d}$, $A^-$, M, and P are as defined in Formula II, $R_{2d}$ is as defined for $R_{2a}$, $R_{2b}$, $R_{3b}$, and $R_{3d}$, and $R_5$ and $R_7$ are defined in Formula III. $R_{16}$ and $R_{17}$, identical or different, are the groups selected from hydrogen, methyl, alkyl with low molecular weight, and halides. Preferably, $R_{16}$ and $R_{17}$ are different and one of them is hydrogen. More preferably, both $R_{16}$ and $R_{17}$ are hydrogen.

Formula XIII

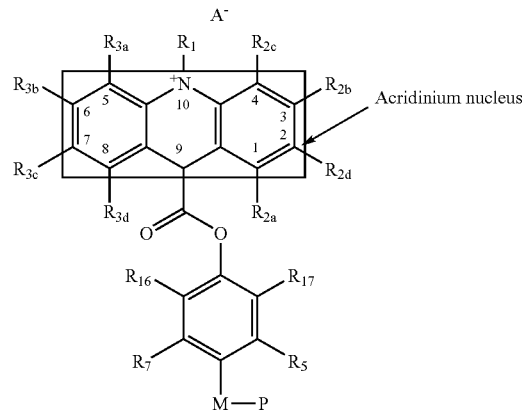

One of the more preferred chemiluminescent acridinium substrates of Formula XIII is compound 4'-Phos-AE (17). As shown in Reaction F, 17 is readily converted by AP to the product 4'-OH-AE (18). It was found that at short measuring times (0.5–0.3 s), 17 emitted light ~190 times faster than 18. While theoretically, either the concentration of the substrate or the product can be measured to estimate enzyme activity, it was found to be more convenient (for effective signal discrimination) to measure the chemiluminescent activity of the substrate, 4'-Phos-AE (17). The chemiluminescent response to the concentration of alkaline phosphatase using 17 as the substrate is given in FIG. 13.

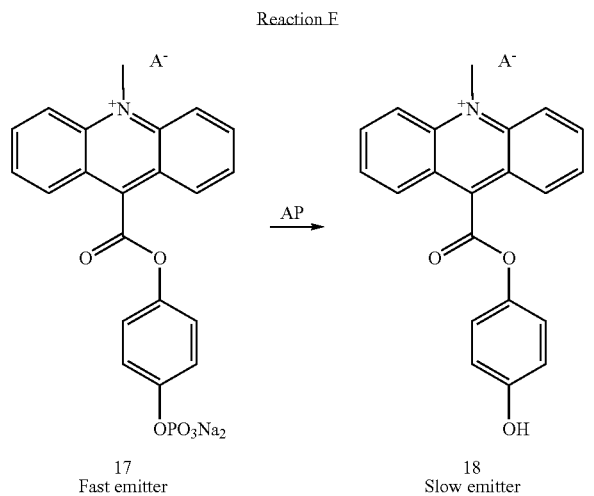

17
Fast emitter

18
Slow emitter

3. Light Emission Spectra

Figure 2P:
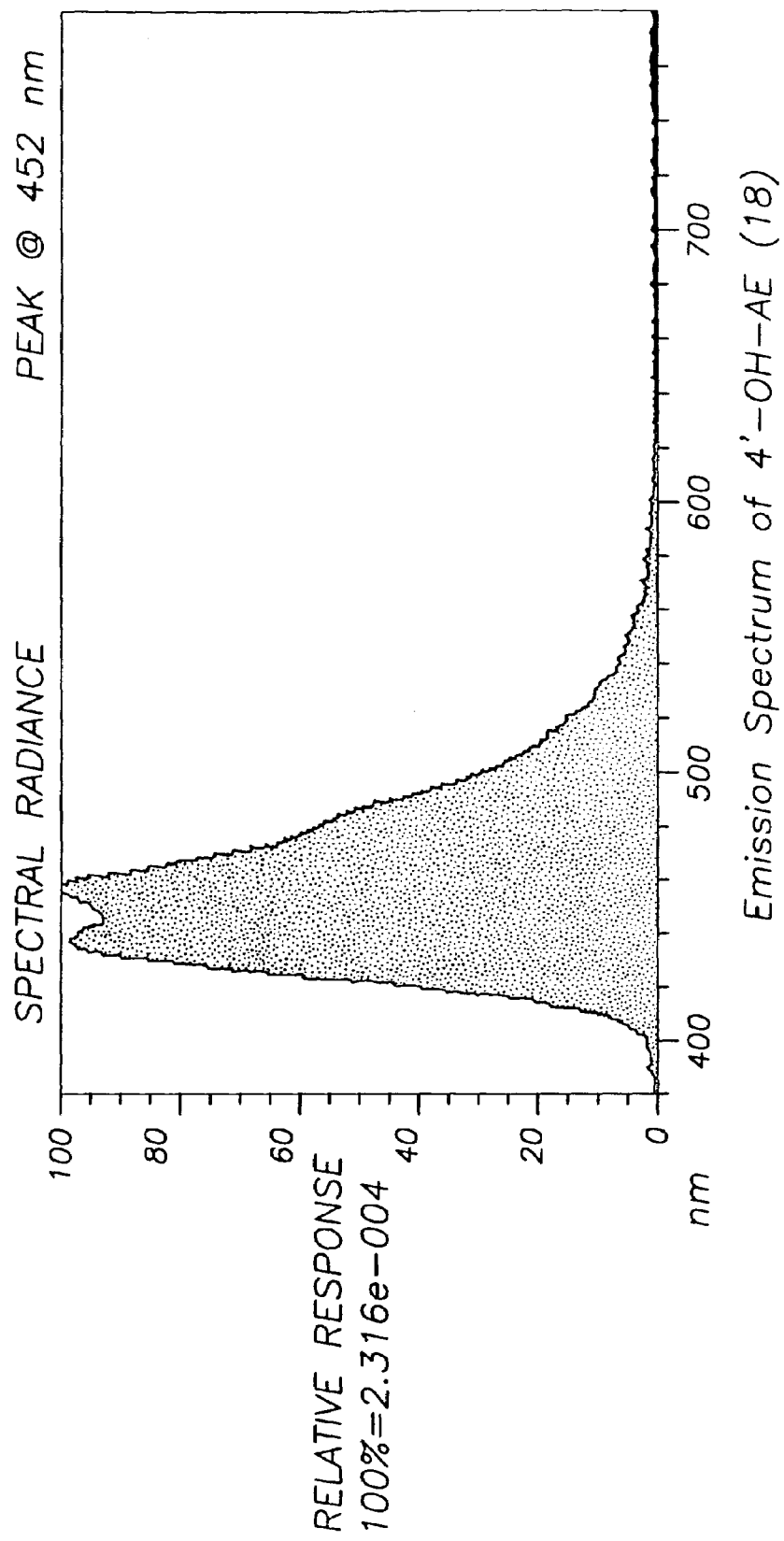

The light emission spectra of compounds 1~12 and 15~18 were determined by a Fast Spectral Scanning System (FSSS) of Photo Research (a division of Kollmorgen Corp.) of Burbank, Calif., U.S.A. The experiment was carried out in a dark room. Each compound was dissolved in acetonitrile or N,N-dimethylformamide. The resulting concentrate was diluted with the same solvent to form the working solution, which upon flashing gave a light emission with an adequate intensity. A typical experiment utilized 10~100 µg or more of the sample in 500 µl of the solvent contained in a 13×100 mm borosilicate test tube. The tube was placed on a test tube rack raised to a proper height. A piece of aluminum foil was placed on the back of the tube to enhance the detectability of the emitted light. The FSSS optical head was placed in front of the tube at an approximate distance of about 130 mm with its lens focused on the liquid in the tube. The sample solution was first treated with 0.35 ml of the Flashing Reagent #1 (Bayer Diagnostics) containing 0.1 N $HNO_3$ and 0.5% $H_2O_2$. The room was then darkened, and 0.35 ml of the Flashing Reagent #2 (Bayer Diagnostics) containing 0.25 N NaOH and 0.5% ARQUAD was added to the reaction mixture immediately. (See U.S. Pat. No. 4,927,769, which is commonly assigned and incorporated herein by reference.) The light which was generated instantaneously following the addition of the Reagent #2 was recorded by FSSS for 5 seconds starting from about one second before the Reagent #2 was added. The various emission spectra determined on FSSS are given in FIGS. 2A–2P, and also summarized in Table 1.

TABLE 1

| Compound | Emission Range* (nm) | Maximum (nm) |
|---|---|---|
| 1 | 430–600 | 478 |
| 2 | 500–780^ | 602 |
| 3 | 430–600 | 474 |
| 4 | 500–780^ | 604 |

TABLE 1-continued

| Compound | Emission Range* (nm) | Maximum (nm) |
|---|---|---|
| 5 | 430–600 | 478 |
| 6 | 500–780^ | 600 |
| 7 | 430–600 | 474 |
| 8 | 500–780^ | 594 |
| 9 | 440–600 | 476 |
| 10 | 520–780^ | 674 |
| 11 | 430–600 | 474 |
| 12 | 510–780^ | 638 |
| 15 | 520–780^ | 678 |
| 16 | 410–580 | 450 |
| 17 | 410–540 | 436 |
| 18 | 410–540 | 452 |

*Range is set for spectral region with signal intensity of above 5% of peak height.
^Emission spectral range goes beyond the scanning limit (380–780 nm) of FSSS.

4. Applications of the Chemiluminescent Enzyme Substrates in Binding Assays

While the specific example of the actual diagnostic assay disclosed here uses 2-Phos-DMAE (1) as a chemiluminescent substrate for alkaline phosphatase, where alkaline phosphatase serves as a label for the detection of human thyroid stimulating hormone (TSH) in serum, it is reasonable to conclude that a variety of hydrolytic enzymes could be used in conjunction with the appropriate chemiluminescent substrates in a variety of assay architectures for detection of either endogenous, diagnostic enzyme markers or other clinically relevant diagnostic markers should the hydrolase be used as a label. Therefore, while we claim those assay architectures as should be obvious or otherwise apparent to those who are skilled in the art of enzymatic, diagnostic assay, we do not restrict our claims to the following descriptions.

a. Conversion of Assay Readout Systems from Colorimetric or Fluorescence Detection to Chemiluminescence Detection:

The co-application of enzyme labels and their dependent luminescent chemistries to bioanalytical techniques has been reported as one of several strategies for developing ultrasensitive clinical detection methodologies (*Clin. Biochem.*, 26, 325, (1993)). Conversion of existing diagnostic test formats from their current methods of calorimetric or fluorometric measurement to the potentially more sensitive method of chemiluminescence detection would have a diverse multiplicity of application in clinical analysis, especially since these calorimetric or fluorometric assays already exist in multitudinous configurations. As mentioned earlier, chromogenic and fluorometric indicator substances have been used in sensitive immunoassays in the form of enzyme substrates for detection of enzymes or the analytes to which these enzymes are directed as labels. The present invention discloses an analytical procedure where in general the chemiluminescent-emission properties of an enzyme substrate are distinguishable from the resultant product and that the enzymatic source for the catalytic conversion of said substrate to product can be used to measure the enzyme activity directly for measurement of either the enzyme or the analytes to which the enzyme would be attached as a label.

b. An analyte, as in the example below on human TSH, is complexed specifically with two different antibodies immobilized on solid phase and tagged with an enzyme label, respectively. The quantity of analyte in a sample should correlate to the quantity of captured label, which in this case is alkaline phosphatase, and should ultimately correlate to the observed magnitude of chemiluminescence. However, we envision more broadly the following scheme of assay architectures generally divided into the two classes referred to independently as immunoassays and nucleic acid assays. We further divide these classes into either homogeneous or heterogeneous assay configurations dependent on the separation of bound from free analyte. Furthermore, we do not restrict our claims to those assay systems currently employing enzymes as labels, i.e., EIA, ELISA, Emit®, etc., but encompass also the realm of clinical diagnostics for which enzymes may be freely substituted for non-enzyme labels, i.e., radioisotopes, chromaphores, fluores, etc.

c. Heterogeneous Chemiluminescent Assay

An enzyme captured by a solid phase matrix, for example, a polystyrene surface, magnetic particle, or combination of both, or precipitating protein, etc., either non-specifically, as with adsorption, or specifically as through the attachment to the solid phase, non-covalently or otherwise, of a (directed) binding partner, including complementary nucleic acid sequence, biotin, antibody, binding protein, receptor, ligand, etc. would be separated from interfering substances through the separation of the solid phase from other assay components prior to application of the chemiluminescent substrate.

The enzyme could be either the endogenous diagnostic marker of interest, a label attached, covalently or otherwise, to a specific binding partner (collectively termed a tracer or probe) which is captured by the solid phase or a secondary reagent required for signal generation or amplification as in enzyme-cycling assays.

Examples of these assay configurations are widely reported in the literature and compendiums of specific constructs have been published (Maggio, E., *Enzyme-immunoassay*, (1990) CRC Press), and (Wild, D., *The Immunoassay Handbook*, (1994) Stockton Press).

A heterogeneous enzyme-immunoassay for the detection of an enzyme phosphatase might be set up in several configurations. The simplest method would be to capture the phosphatase using an antibody which would specifically bind the phosphatase to separable solid phase, washing interfering substances from the solid phase prior to the addition of chemiluminescent phosphorylated substrate. A second method directed toward a protein analyte, could be fashioned in which a sandwich assay utilizing two antibodies, the first of which would be linked to a solid phase as described above, the second would be coupled to the signal generating system, alkaline phosphatase, β-galactosidase etc. The concentration of the enzyme label in the assay is then measured by application of the specific chemiluminescent substrate. Alternatively, in a competitive assay for a small analyte, a chemiluminescence generating enzyme such as alkaline phosphatase can be coupled to the same hapten for use in the assay as a tracer, where an endogenous analyte and the hapten-enzyme conjugate would compete for a limited number of solid phase binding sites using a similar signal readout mechanism as is described above for the sandwich assay.

d. Homogeneous Chemiluminescent Assays

Assays that employ a homogeneous format can also be coupled to the present invention. Homogeneous assay architectures do not require the separation of assay components to discriminate between negative and positive analyte controls and therefore require fewer processing steps than heterogeneous assays. Homogeneous assay technologies such as Emit® and CEDIA™ could be adapted to chemiluminescence detection. Emit® assays for small analytes could be developed in which both a hapten-enzyme conjugate, similar to that described above, and an analyte-specific antibody would be added to a clinical sample. The resultant chemiluminescence would be dependent on the degree of enzyme inhibition occurring with the formation of the antibody-enzyme complex. CEDIA™ assays are envisioned in which a hapten is covalently conjugated to the amino-terminal fragment of recombinant β-galactosidase or the enzyme donor (ED) fragment. Both the hapten-ED conjugate and an analyte specific antibody would then be incubated with the clinical sample in the presence of the carboxy-terminal fragment of β-galactosidase, termed enzyme acceptor (EA) (Engel, W., Khanna, P., *J. Immunol. Methods*, 150, 99 (1992)). The magnitude of resultant chemiluminescence from the supposed enzyme substrate catalysis product, 2-hydroxy-DMAE, would depend on the degree of remaining enzyme inactivation.

e. Chemiluminescent Nucleic Acid Assays

We propose as obvious the application of said chemiluminescent enzyme substrate systems for the labeling and/or detection of nucleic acids in nucleic acid assays.

The invention disclosed herein is illustrated, but not limited, by the following examples.

EXAMPLE 1

Synthesis of (2',6'-dimethyl-4'-benzyl-oxycarbonyl) phenyl 2-hydroxy-10-methyl-acridinium-9-carboxylate trifluoroacetate (2-OH-DMAE-Bn, 4).

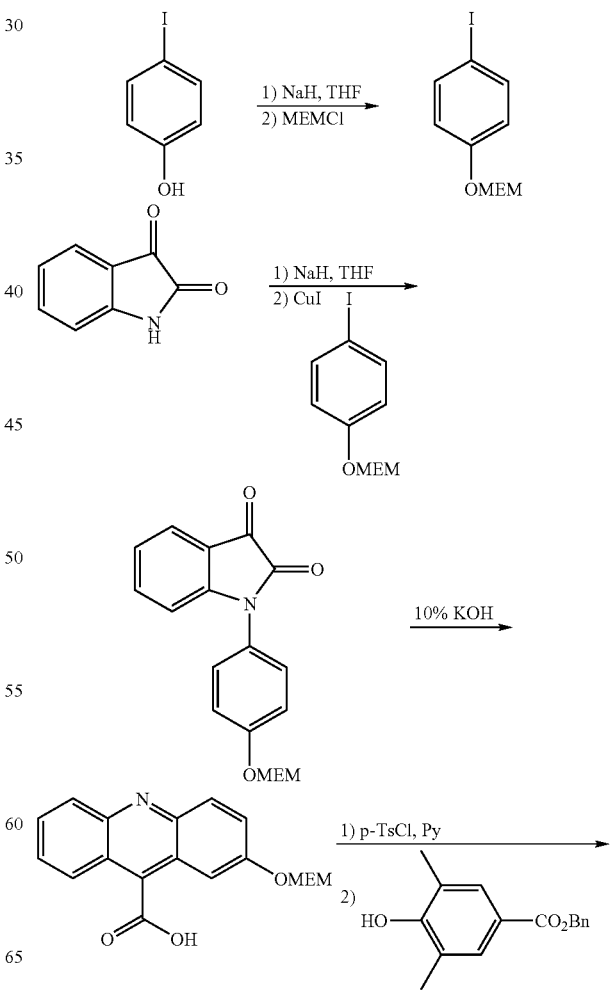

-continued

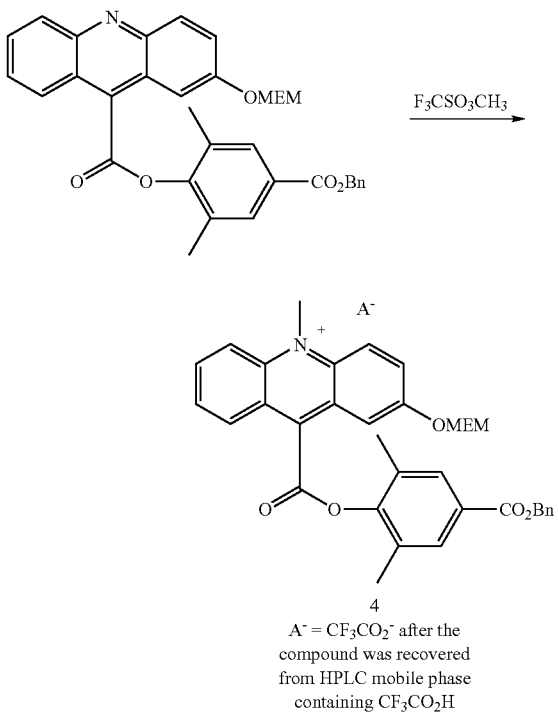

A⁻ = CF₃CO₂⁻ after the compound was recovered from HPLC mobile phase containing CF₃CO₂H

4-Methoxyethoxymethoxy-iodobenzene

A solution of 4-iodophenol (10 g, 45.45 mmol) in 200 ml of anhydrous tetrahydrofuran was treated at 0° C. with sodium hydride (2.36 g, 60% dispersion, 59.09 mmol) for 5 minutes. To the resulting mixture, methoxyethoxymethyl chloride (8.3 ml, 72.73 mmol) was slowly added over a 5-minute period. The mixture was stirred at 0° C. under nitrogen for 30 minutes, warmed to room temperature, and stirred for 24 hours. The solvent was removed under reduced pressure. The residue was taken into 500 ml of ether, washed with 5% sodium hydroxide (4×200 ml), water (4×200 ml), saturated sodium chloride (1×200 ml), and dried over sodium sulfate. Evaporation of the solvent under reduced pressure gave an oily product in 14.1 g. TLC (silica gel, ether): Rf 0.5.

N-(4-Methoxyethoxymethoxy)phenyl isatin

A solution of isatin (4.0 g, 27.2 mmol) in 200 ml of anhydrous N,N-dimethylformaldehyde was treated at room temperature with sodium hydride (1.036 g, 60% dispersion, 32.64 mmol) for 0.5 hour, followed by addition of 4-methoxyethoxymethoxy-iodobenzene (12.57 g, 40.8 mmol) and copper (I) iodide (10.34 g, 54.4 mmol). The resulting mixture was stirred at 160° C. under nitrogen for 17 hours. It was cooled to room temperature, and diluted with 400 ml of chloroform. The resulting mixture was filtrated to remove the inorganic materials. The filtrate was evaporated under reduced pressure to give a crude mixture containing N-(4-methoxyethoxymethoxy)phenyl isatin as a major product. TLC (silica gel, ether): Rf 0.8.

2-Methoxyethoxymethoxy-acridine-9-carboxylic acid

The above crude 4-methoxyethoxymethoxyphenyl isatin, without purification, was suspended in 120 ml of 10% potassium hydroxide. The suspension was refluxed at 150° C. for 5 hours. After cooling to room temperature, the mixture was filtrated to remove the orange impurities. The filtrate was acidified in an ice-water bath with concentrated hydrochloric acid to pH 2. The resulting yellow precipitate was collected and washed with water (4×50 ml) and air-dried. The dried material was further washed with ether (6×50 ml) to yield the desired product in 6.7 g. TLC (silica gel, 30% methanol/chloroform): Rf 0.5.

(2',6'-Dimethyl-4'-benzyloxycarbonyl)phenyl 2-methoxy-ethoxy-methoxy-acdidine-9-carboxylate A suspension of 2-methoxyethoxymethoxy-acridine-9-carboxylic acid (3.6 g, 11 mmol) in 150 ml of anhydrous pyridine was treated with p-toluenesulfonyl chloride (4.183 g, 22 mmol) at 0° C. for 5 minutes to form a homogeneous brown solution. Then, benzyl 3,5-dimethyl-4-hydroxy-benzoate (2.818 g, 11 mmol) was added. The solution was stirred at room temperature under nitrogen for 20 hours. The solvent was removed under reduced pressure. The residue was separated on a silica flash chromatography column packed in hexane. It was eluted with 50% ether/hexane (1 liter) followed by 70% ether/hexane (3 liters). The product fraction was obtained from the 70% ether/hexane eluent. Evaporation of the solvents under reduced pressure gave 3.74 g of the desired product. TLC (silica gel, ether): Rf 0.8.

(2',6'-Dimethyl-4'-benzyloxycarbonyl)phenyl 2-hydroxy-10-methyl-acridinium-9-carboxylate trifluoroacetate A light-yellow solution of (2',6'-dimethyl-4'-benzyloxycarbonyl)phenyl 2-methoxyethoxymethoxy-acdidine-9-carboxylate (400 mg, 0.708 mmol) in 20 ml of anhydrous methylene chloride was treated with methyl trifluoromethanesulfonate (0.4 ml, 3.54 mmol) at room temperature under nitrogen with stirring for 14 hours. The resulting mixture was treated with anhydrous ether (20 ml). The precipitate was collected and washed with ether (4×20 ml) to yield 325 mg of the crude product. MS: (ESI): m/z 492.6 (M⁺). ¹H NMR (300 MHz, MeOD-d₄/CDCl₃): δ2.52 (6H, s), 5.01 (3H, s), 5.42 (2H, s), 7.37–7.51 (5H, m), 7.81 (1H, d, J=2.6 Hz), 7.97 (2H, s), 8.10 (1H, t, J=7.0 Hz), 8.16 (1H, dd, J₁=8.0 Hz, J₂=2.6 Hz), 8.42 (1H, t, J=7.0 Hz), 8.60 (1H, d, J=8.8 Hz), and 8.73 (2H, two overlapping doublets, J~8.0 Hz). The product (25 mg) was further purified on a preparative HLPC column (YMC, 250×30 mm, ODS, 10 μm), eluted in gradient by mixing 0.05% TFA/water (solvent A) and 0.05% TAF/acetonitrile (solvent B) in the following manner: 40 to 60% B in 40 minutes, flow rate 20 ml/minute, monitored at 260 nm. The desired product at retention time of ~30 minutes was collected and crystallized from methylene chloride/ether to give 17 mg of pure 4.

EXAMPLE 2

Synthesis of (2',6'-dimethyl-4'-benzyloxy-carbonyl) phenyl 2-phosphoryloxy-10-methyl-acridinium-9-carboxylate trifluoroacetate (2-Phos-DMAE-Bn, 3)

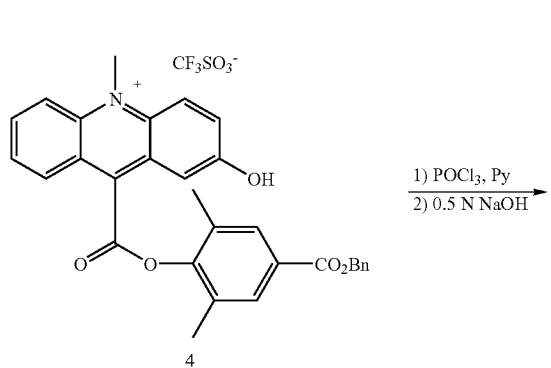

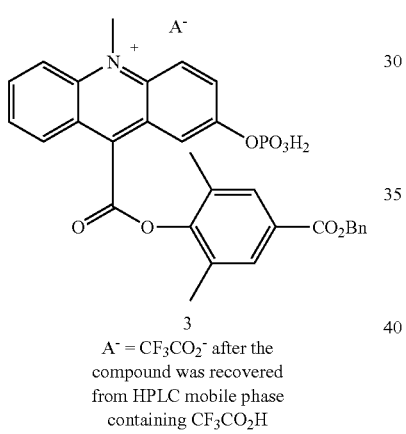

A solution of (2',6'-dimethyl-4'-benzyloxycarbonyl)phenyl 2-hydroxy-10-methyl-acridinium-9-carboxylate trifluoromethane-sulfonate (50 mg, 0.102 mmol) in pyridine (0.5 ml) was cooled to 0° C. and then added dropwise over a 3 minute period to a pre-cooled solution of phosphorous oxychloride (57 μl, 6 eq.) in 0.5 ml of pyridine. The reaction mixture was stirred at 0° C. under nitrogen for 30 minutes. The reaction was quenched with 400 μl of 0.5 N NaOH followed by another 200 μl of 1 N NaOH. The mixture was diluted with 1 ml of water, and then filtrated. The resulting yellow solid was dissolved in mixed DMF and water, and separated on a preparative HPLC column (YMC, 250×30 mm, ODS, 10 μm), eluted in gradient by mixing 0.05% TFA/water (solvent A) and 0.05% TAF/acetonitrile (solvent B) in the following manner: 30 to 60% B in 40 minutes, flow rate 20 ml/minute, monitored at 260 nm. The desired product (3) at retention time of 32 minutes was obtained in 20 mg. MS (MALDI-TOF): m/z 573 (M+1).

EXAMPLE 3

Synthesis of (2',6'-dimethyl-4'-carboxyl)phenyl 2-hydroxy-10-methyl-acridinium-9-carboxylate trifluoroacetate (2-OH-DMAE, 2)

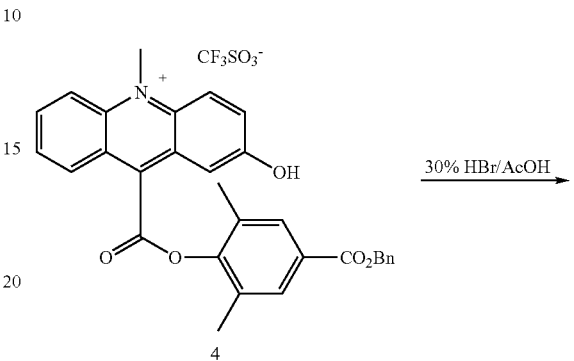

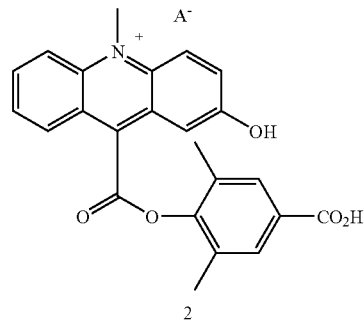

A solution of (2',6'-dimethyl-4'-benzyloxy-carbonyl)phenyl 2-hydroxy-10-methyl-acridinium-9-carboxylate trifluoromethanesulfonate (100 mg) in 4 ml of 30% hydrogen bromide in acetic acid was stirred at 55° C. under nitrogen for 1 hour, and then treated with 10 ml of anhydrous ether. The resulting precipitate was collected and washed with ether (4×10 ml) to give 80 mg of (4-carboxyl-2,6-dimethyl) phenyl 2-hydroxy-10-methyl-acridinium-9-carboxylate bromide. MS (ESI): m/z 402.7 (M+). $^1$H NMR (300 MHz, CD$_3$CN/MeOD-d$_4$): 52.52 (6H, s), 4.95 (3H, s), 7.78 (1H, d, J=2.7 Hz), 7.76 (2H, s), 8.10 (1H, t, J=7.0 Hz), 8.13 (1H, dd, J$_1$=9.9 Hz, J$_{3=2}$=2.7 Hz), 8.40 (1H, d t, J$_1$=2.7 Hz, J$_2$=8.0 Hz), 8.62 (1H, d, J=8.0 Hz), 8.77 (1H, d, J=9.2 Hz), and 8.78 (1H, d, J=9.9 Hz). The further purification of the above product (68 mg) was carried out by preparative HLPC (YMC, 250×30 mm, ODS, 10 μm), eluted in gradient by mixing 0.05% TFA/water (solvent A) and 0.05% TAF/ acetonitrile (solvent B) in the following manner: 10 to 60% B in 40 minutes, flow rate 20 ml/minute, monitored at 260 nm. The desired product (2) at retention time of ~27 minutes was obtained in 46 mg.

EXAMPLE 4

Synthesis of (2',6'-dimethyl-4'-carboxyl)phenyl 10-methyl-2-Phosphoryloxy-acridinium-9-carboxylate bromide (2-Phos-DMAE, 1)

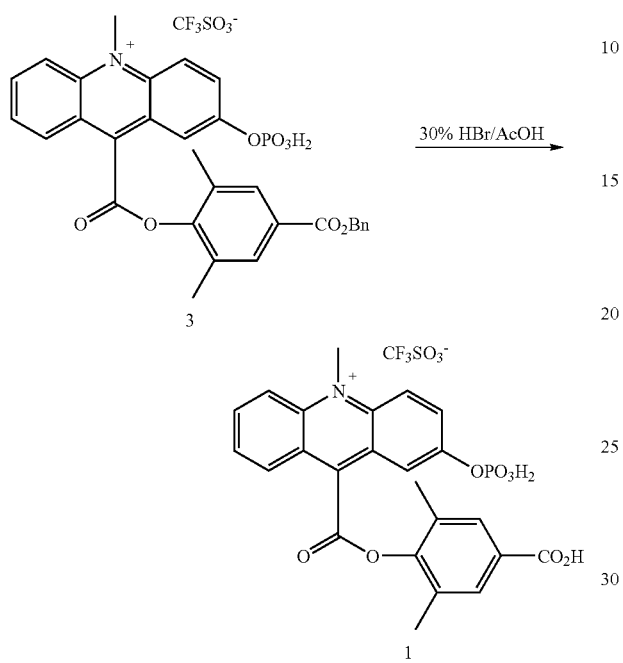

A mixture of (2',6'-dimethyl-4'-benzyloxycarbonyl)phenyl 10-methyl-2-phosphoryloxy-10-methyl-acridinium-9-carboxylate trifluoroacetate (3, 37 mg) and 2.5 ml of 30% hydrogen bromide in acetic acid was stirred at 50° C. under nitrogen for 1.5 hour. The resulting mixture was cooled to room temperature, and treated with ether to form yellow precipitate. It was dissolved in mixed DMF/water with the help of a small amount of triethylamine. The mixture was separated on a preparative HLPC column (YMC, 250×30 mm, ODS, 10 μm), eluted in gradient by mixing 0.05% TFA/water (solvent A) and 0.05% TAF/acetonitrile (solvent B) in the following manner: 10 to 60% B in 40 minutes, flow rate 20 ml/minute, monitored at 260 nm. The fraction at retention time of ~17 minutes was collected and lyophilized to dryness to give pure 1 in 5.3 mg. MS (DALTI-TOF): m/z 482.818 (M+1).

EXAMPLE 5

Synthesis of phenyl 2-hydroxy-10-methyl-acridinium-9-carboxylate trifluoromethanesulfonate (2-OH-AE, 6)

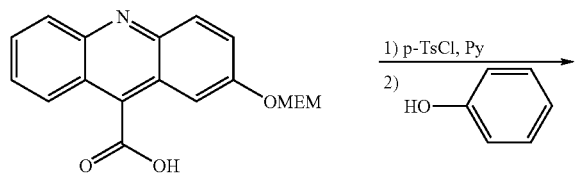

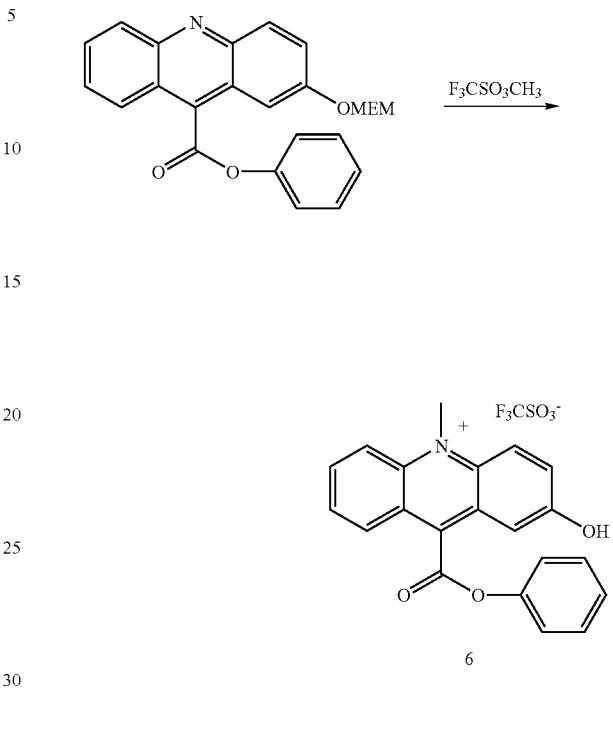

Phenyl 2-methoxyethoxymethoxy-acdidine-9-carboxylate

To a solution of 2-methoxyethoxymethoxy-acridine-9-carboxylic acid (101 mg, 0.308 mmol) in 5 ml of anhydrous pyridine was added p-toluenesulfonyl chloride (117 mg, 0.616 mmol). It was stirred at 0° C. for 5 minutes and at room temperature for an additional 10 minutes before 29 mg (0.038 mmol) of phenol was added. The reaction was stirred at room temperature under nitrogen overnight. The reaction mixture was evaporated under reduced pressure. The residue was suspended in mixed methanol and ethyl acetate and filtrated. The resulting filtrate was reduced to a small volume and separated on 4 preparative silica gel plates (20×20 cm×2 mm thick), which were developed with hexane/ether (2:1). The major product band was collected and eluted with the same solvent system. Removal of the solvents gave 27 mg of the pure product. TLC (silica gel, hexane/ether 2:1): Rf 0.9.

Phenyl 2-hydroxy-10-methyl-acridinium-9-carboxylate tri-fluoromethanesulfonate

A solution of phenyl 2-methoxyethoxymethoxy-acdidine-9-carboxylate (25 mg, 0.062 mmol) in 1.5 ml of anhydrous methylene chloride was treated with methyl trifluoromethanesulfonate (38 μl, 0.336 mmol) at room temperature under nitrogen with stirring overnight. The reaction was diluted with another 0.5 ml of methylene chloride and then treated with anhydrous ether (4 ml). The resulting precipitate was collected and washed with ether to give 6 in 19 mg. MS (ESI): m/z 330 (M+).

EXAMPLE 6

Synthesis of phenyl 10-methyl-2-Phosphoryloxy-acridinium-9-carboxylate trifluoroacetate (2-Phos-AE, 5)

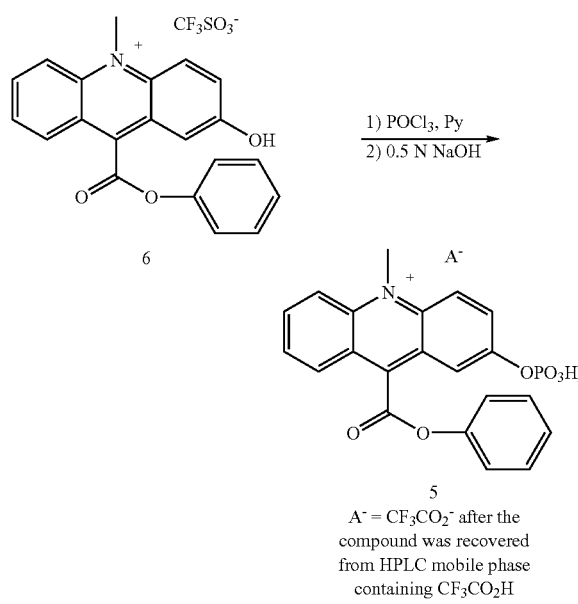

A⁻ = CF₃CO₂⁻ after the compound was recovered from HPLC mobile phase containing CF₃CO₂H A solution of phenyl 2-hydroxy-10-methyl-acridinium-9-carboxylate trifluoro-methanesulfonate (19 mg, 0.040 mmol) in pyridine (0.3 ml) was cooled to 0° C. and then added slowly to a pre-cooled solution of phosphorous oxychloride (22 µl, 0.24 mmol) in 0.3 ml of pyridine. The reaction mixture was stirred at 0° C. under nitrogen for 30 minutes, and quenched with 500 µl of 5% ammonium hydroxide for 10 minutes. The solution was then diluted with 1 ml of water and neutralized with 1 N HCl. The mixture was separated on a preparative HPLC column (YMC, 300×20 mm, ODS, 10 µm), eluted in gradient by mixing 0.05% TFA/water (solvent A) and 0.05% TAF/acetonitrile (solvent B) in the following manner: 10 to 60% B in 40 minutes, flow rate 20 ml/minute, monitored at 260 nm. The desired product (5) at retention time of 18 minutes was obtained in 8 mg. MS (ESI): m/z 410 (M⁺).

EXAMPLE 7

Synthesis of (2′, 6′-dimethyl-4′-carboxyl)phenyl 2-phosphoryloxy-10-sulfobutyl-acridinium-9-carboxylate (2-Phos-NSB-DMAE, 7)

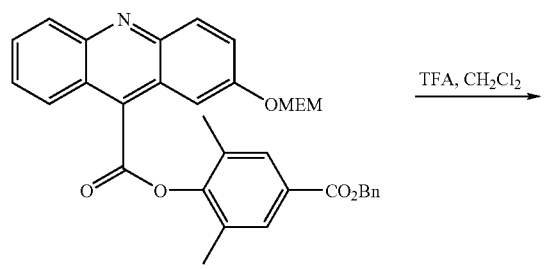

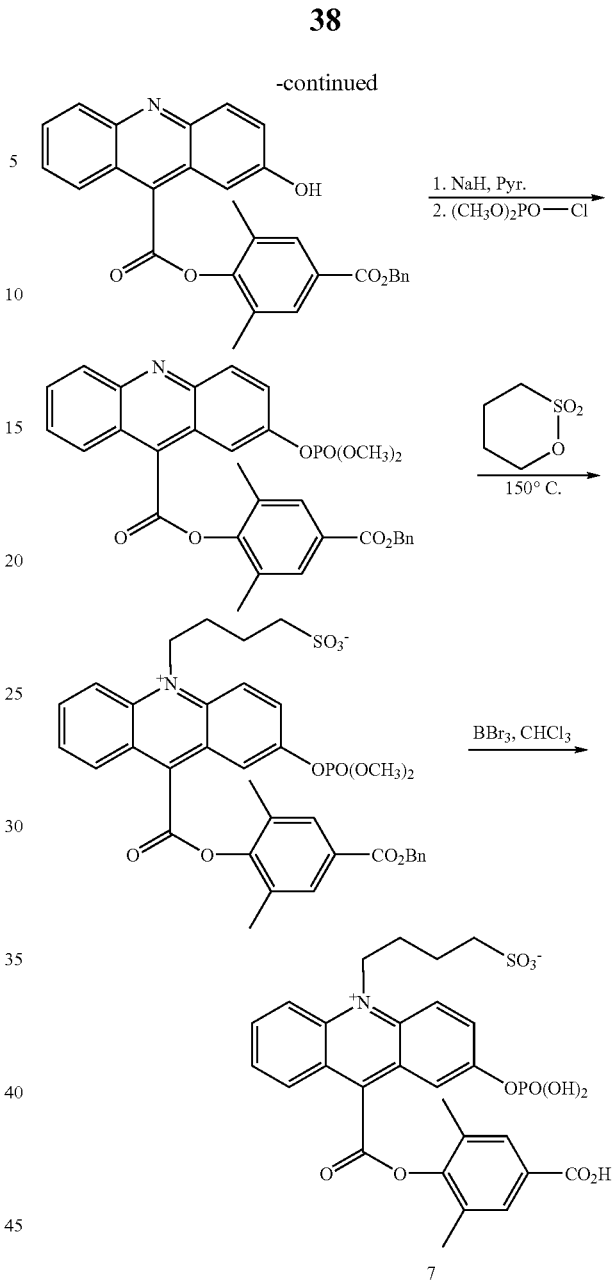

(2′,6′-Dimethyl-4′-benzyloxycarbonyl)phenyl 2-hydroxy-acridine-9-carboxylate

A solution of (2′,6′-dimethyl-4′-benzyloxy-carbonyl)phenyl 2-methoxyethoxymethoxy-acridine-9-carboxylate (960 mg, 1.7 mmol) in methylene chloride (5 ml) was treated with trifluoroacetic acid (5 ml) at room temperature for 19 hours. The reaction mixture was blown to dryness with a nitrogen stream and the residue was suspended in ether. The product was collected and further washed with ether (2×10 ml) to give 610 mg. MS (MALTI-TOF): m/z 479 (M+1).

(2′,6′-Dimethyl-4′-benzyloxycarbonyl)phenyl 2-dimethyl-phosphoryloxy-acridine-9-carboxylate To a solution of (2′,6′-dimethyl-4′-benzyloxycarbonyl) phenyl 2-hydroxy-acridine-9-carboxylate (50 mg, 0.105 mmol) in pyridine (2 ml) at 0° C. under nitrogen was added sodium hydride (5 mg, 0.208 mmol). It was allowed to stir at room temperature for 1 hour before dimethoxychlorophosphate (56 µl, 0.519 mmol) was added. The reaction was continued to stir for 3 hours. The product was isolated from a preparative HLPC column (YMC, 250×30 mm, ODS, 10 µm). The column was eluted in gradient by mixing 0.05% TFA/water (solvent A) and 0.05% TFA/acetonitrile (solvent B) in the following manner: 40 to 80% B in 40 minutes, flow rate at 20 ml/minute, monitored at 260 nm. The fraction at retention time of ~52 minutes was collected and lyophilized to dryness to give the desired product in 45 mg. MS (MALTI-TOF): m/z 587 (M+1).

(2',6'-Dimethyl-4'-benzyloxycarbonyl)phenyl 2-dimethyl-phosphoryloxy-10-sulfobutyl-acridinium-9-carboxylate A mixture of (2',6'-dimethyl-4'-benzyloxycar-bonyl)phenyl 2-dimethylphosphoryloxy-acridine-9-carboxylate (45 mg, 0.0768 mmol) and 1,4-butanesultone (1 ml, 9.78 mmol) was stirred at 150° C. for 6 hours under nitrogen. The resulting thick gum was dissolved in a mixture of acetonitrile/water. The solution was separated on a preparative HLPC column (YMC, 250×30 mm, ODS, 10 µm). The column was eluted in gradient by mixing 0.05% TFA/water (solvent A) and 0.05% TFA/acetonitrile (solvent B) in the following manner: 40 to 80% B in 40 minutes, flow rate at 20 ml/minute, monitored at 260 nm. The fraction at retention time of ~21 minutes was collected and lyophilized to dryness to give the desired product in 1 mg. MS (MALTI-TOF): m/z 723 (M+1).

(2',6'-Dimethyl-4'-carboxyl)phenyl 2-phosphoryloxy-10-sulfo-butyl-acridinium-9-carboxylate A solution of (2',6'-dimethyl-4'-benzyl-oxycarbonyl)phenyl 2-dimethylphosphoryloxy-10-sulfobutyl-acridinium-9-carboxylate (1 mg, 0.00140 mmol) in chloroform (0.5 ml) was treated with boron tribromide (4 µl, 0.0423 mmol). It was stirred at room temperature under nitrogen for 3 hours. The mixture was blown with a nitrogen stream to dryness then dissolved in acetonitrile and water mixture. The desired product was isolated from a semi-preparative HLPC column (Phenomenex, 300×7.8 mm, ODS, 10 µm). The column was eluted in gradient by mixing. 0.05% TFA/water (solvent A) and 0.05% TFA/acetonitrile (solvent B) in the following manner: 10 to 60% B in 40 minutes, flow rate at 2.5 ml/minute, monitored at 260 nm. The fraction at retention time of ~17 minutes was collected and lyophilized to dryness to give the desired product in 0.1 mg. MS (MALTI-TOF): m/z 605 (M+1).

EXAMPLE 8

Synthesis of (2',6'-dimethyl-4'-carboxyl)phenyl 2-hydroxy-10-sulfobutyl-acridinium-9-carboxylate (2-OH-NSB-DMAE, 8)

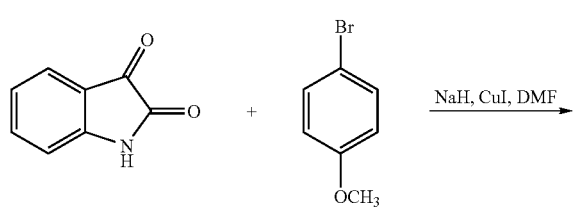

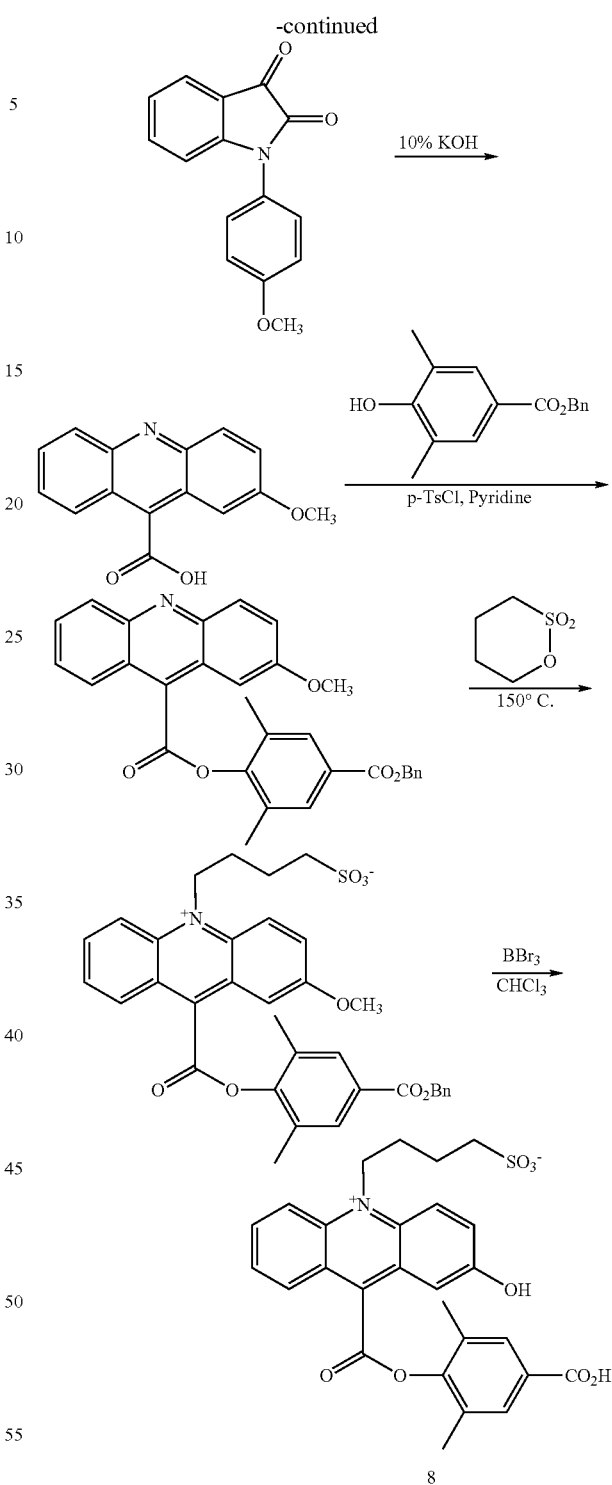

N-(4-methoxyphenyl)isatin

A solution of isatin (2.5 g, 0.017 mol) in anhydrous DMF (50 ml) was cooled to 0° C. under a nitrogen atmosphere and treated with sodium hydride (0.5 g, 1.2 equivalents). A purple solution was formed which was stirred at 0° C. for 30 minutes and then warmed to room temperature. 4-Bromoanisole (2.13 ml, 1 equivalent) was added followed by copper iodide (6.46 g, 2 equivalents). The reaction was heated in an oil-bath at 145° C. for 7 hours. The reaction was then cooled to room temperature and diluted with an equal volume of ethyl acetate. This suspension was filtered and the filtrate was evaporated to dryness. TLC (1:4, ethyl acetate: hexanes) indicated a very clean reaction; Rf (product)=0.5. The crude material was used as such for the next reaction.

2-Methoxy-acridine-9-carboxylic acid

The crude N-(4-methoxyphenyl)isatin from the above was suspended in 10% aqueous potassium hydroxide (150 ml) and refluxed under a nitrogen atmosphere. After 4 hours, the reflux was stopped and the reaction was filtered while still hot. The filtrate was diluted with water (~150 ml) and ice. This solution was then acidified with concentrated hydrochloric acid. A yellow precipitate appeared which was collected by filtration. The precipitate was rinsed with cold water and ether and then air-dried. The dried residue was then transferred to a round-bottom flask with the aid of methanol and the partial solution was evaporated to dryness. The resulting residue was evaporated to dryness from toluene twice. A yellowish-brown powder was recovered in 1.15 g. TLC (1:4, methanol:chloroform) indicated a clean reaction; Rf (product)=0.14. This material was used as such for the next reaction.

2',6'-Dimethyl-4'-benzyloxycarbonylphenyl 2-methoxyacri-dine-9-carboxylate

2-Methoxyacridine-9-carboxylic acid (0.8 g, 0.0032 mol) in anhydrous pyridine (50 ml) was cooled in an ice-bath under a nitrogen atmosphere and treated with p-toluenesulfonyl chloride and 4-benzyloxycarbonyl-2,6-dimethylphenol (0.81 g, 0.0032 mol). The reaction was warmed to room temperature and stirred under a nitrogen atmosphere for 24 hours. The solvent was then removed under reduced pressure and the residue was dissolved in chloroform (10 ml). The product was purified by flash chromatography using 5% ethyl acetate, 25% chloroform, 70% hexanes. Evaporation of the flash fractions containing the product yielded a bright yellow solid in 0.84 g. MS (MALDI-TOF): m/z MS 492.8 (M+1)

(2',6'-Dimethyl-4'-benzyloxycarbonyl)phenyl 0.2-methoxy-10-sulfobutyl-acridinium-9-carboxylate A mixture of (2',6'-dimethyl-4'-benzyloxy-carbonyl)phenyl 2-methoxy-acridine-9-carboxylate (200 mg, 0.407 mmol) in 2 ml of 1,4-butanesultone was stirred at 150° C. for 19 hours under nitrogen. The resulting thick gum was dissolved in a mixed acetonitrile/water solvent. The solution was separated on a preparative HLPC column (YMC, 250× 30 mm, ODS, 10 μm). The column was eluted in gradient by mixing 0.05% TFA/water (solvent A) and 0.05% TFA/ acetonitrile (solvent B) in the following manner: 30 to 60% B in 40 minutes, flow rate at 20 ml/minute, monitored at 260 nm. The fraction at retention time of ~37 minutes was collected and lyophilized to dryness to give the desired product in 58.5 mg. MS (MALTI-TOF): m/z 629 (M+1).

(2',6'-Dimethyl-4'-carboxyl)phenyl 2-hydroxy-10-sulfobutyl-acridinium-9-carboxylate A solution of (2',6'-dimethyl-4'-benzyl-oxycarbonyl)phenyl 2-methoxy-10-sulfobutyl-acridinium-9-carboxylate (50 mg, 0.080 mmol) in chloroform (4 ml) was treated with boron tribromide (50 μl, 0.529 mmol) and was stirred at room temperature under nitrogen for 3 hours. The reaction was blown with a nitrogen stream to dryness then dissolved in acetonitrile and water mixture. The desired product was isolated from a preparative HLPC column (YMC, 250×30 mm I.D., ODS, 10 μm). The column was eluted in gradient by mixing 0.05% TFA/water (solvent A) and 0.05% TFA/ acetonitrile (solvent B) in the following manner: 10 to 60% B in 40 minutes, flow rate at 20 ml/minute, monitored at 260 nm. The fraction at retention time of ~26 minutes was collected and lyophilized to dryness to give the desired product in 18 mg. MS (MALTI-TOF): m/z 525 (M+1). This compound was further purified, using another preparative HLPC column (YMC, 300×20 mm I.D., ODS, 10 μm). The column was eluted in gradient by mixing 0.05% TFA/water (solvent A) and 0.05% TFA/acetonitrile (solvent B) in the following manner: 10 to 60% B in 40 minutes, flow rate at 16 ml/minute, monitored at 260 nm. The pure product was obtained in 4 mg. MS (MALTI-TOF): m/z 525 (M+1).

EXAMPLE 9

Syntheses of (2',6'-dimethyl-4'-carboxyl)phenyl 2-hydroxy-7-methoxy-10-methyl acridinium-9-carboxylate (2-OH-7-MeO-DMAE, 10) and (2',6'-dimethyl-4'-carboxyl)phenyl 2-phosphoryloxy-7-methoxy-10-methyl acridinium-9-carboxylate (2-Phos-7-MeO-DMAE, 9)

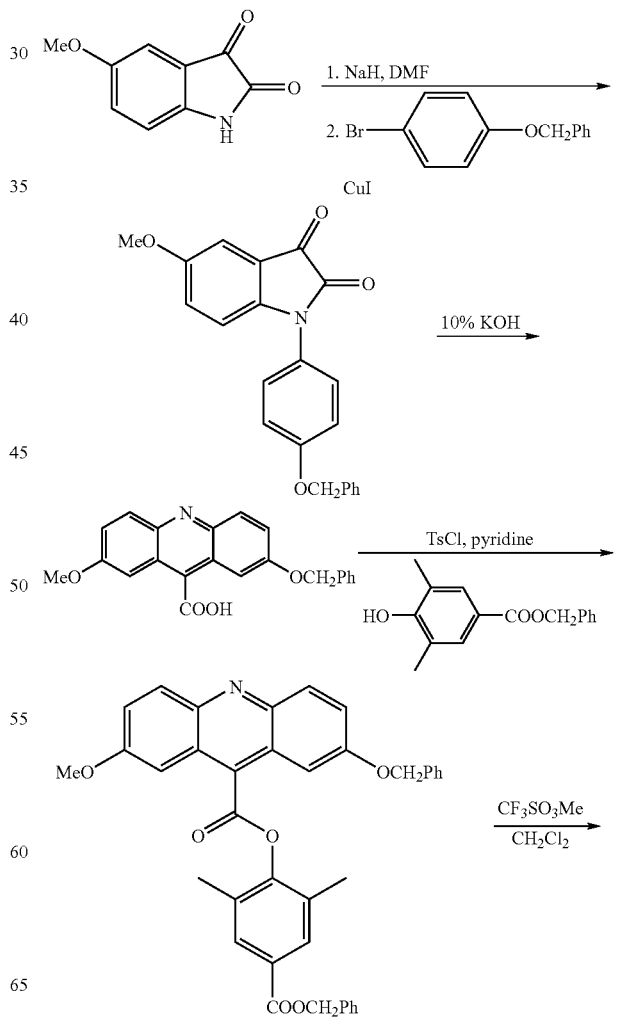

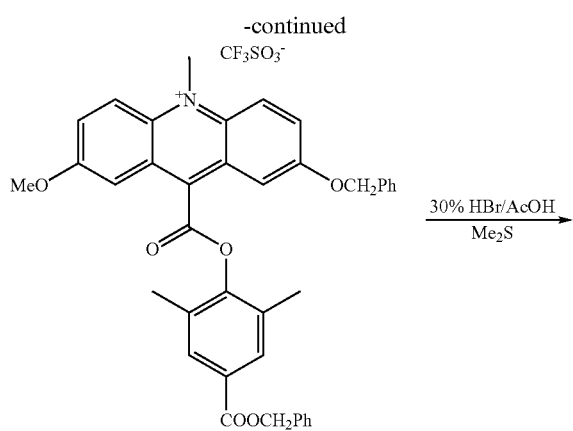

Synthesis of 4-benzyloxybromobenzene

4-Bromophenol (2 g, 0.0116 mol) in acetone (40 ml) was treated with potassium carbonate (1.91 g, 1.2 equivalents) and benzyl bromide (1.44 ml, 1.05 equivalents). The reaction was refluxed under nitrogen. After 5–6 hours of reflux, the reaction was cooled to room temperature and diluted with an equal volume of ethyl acetate. This was diluted further with water and the organic layer was separated, dried over magnesium sulfate and evaporated to dryness to afford a white fluffy powder. Yield=2.36 g (73%).

Synthesis of N-(4'-benzyloxy)phenyl-5-methoxyisatin

5-Methoxyisatin (1.5 g, 0.847 mmol) in anhydrous DMF (50 ml) was cooled in an ice-bath under nitrogen and treated with sodium hydride (0.25 g, 1.2 equivalents). After 15–20 minutes in ice, a solution of 4-benzyloxybromobenzene (2.36 g) in DMF (~3 ml) was added along with CuI (3.23 g, 2 equivalents). The resulting reaction was heated in an oil-bath at 140° C. under nitrogen for 24 hours. The reaction was then filtered and the filtrate was evaporated to dryness. The residue was suspended in ethyl acetate and purified by flash chromatography using 35% ethyl acetate in hexane. Evaporation of the flash fractions afforded the alkylated isatin as an orange-brown solid. Yield=1 g (32%).

Synthesis of 2-benzyloxy-7-methoxyacridine-9-carboxylic acid

The N-alkylated isatin from above (1 g) was suspended in 10% potassium hydroxide (100 ml and refluxed under nitrogen for 4 hours. The reaction was then filtered while still hot and the filtrate was cooled in ice. This was acidified carefully with a mixture of ice and concentrated HCl until a thick yellow precipitate separated out. The precipitate was allowed to stand for ~15 minutes and was then collected by filtration. After rinsing with ether, the product was thoroughly air dried. Yield=0.75 g (75%).

Synthesis of (2',6'-dimethyl-4'-benzyloxycarbonyl)phenyl 2-benzyloxy-7-methoxy-acridine-9-carboxylate 2-Benzyloxy-7-methoxy-acridine-9-carboxylic acid (0.36 g, 0.001 mol) in anhydrous pyridine (30 ml) was cooled in an ice-bath under nitrogen and treated with p-toluenesulfonyl chloride (0.39 g, 2 equivalents) followed by 4-carbobenzyloxy-2,6-dimethylphenol (0.3 g, 1.2 equivalents). The reaction was warmed to room temperature and stirred for 16 hours under nitrogen. The solvent was then removed under reduced pressure and the residue was dissolved in chloroform (~60 ml). The chloroform solution was washed with 3% aqueous ammonium chloride. It was then dried over magnesium sulfate and evaporated to dryness. The crude product was purified by preparative TLC using 70% hexane, 27% chloroform, 3% methanol and isolated as a yellow solid. Yield=0.31 g (50%). MALDI-TOF MS 599.02 obs. (597.67 calc.).

Synthesis of (2',6'-dimethyl-4'-benzyloxycarbonyl)phenyl 2-benzyloxy-7-methoxy-10-methyl-acridinium-9-carboxylate trifluoromethanesulfonate The acridine ester from above (0.31 g, 0.52 mmol) was dissolved in dichloromethane (5 ml) and treated with methyl trifluoromethanesulfonate (0.575 ml, 10 equivalents). The reaction was stirred at room temperature for 16 hours. Ether (150 ml) was then added and the precipitated product was collected by filtration and air dried. Yield=0.23 g. MALDI-TOF MS 613.33 obs. (612.7 calc.).

Synthesis of (2',6'-dimethyl-4'-carboxyl)phenyl 2-hydroxy-7-methoxy-10methyl-acridinium-9-carboxylate (10)

The acridinium ester from above (0.124 g) was stirred in a mixture of methyl sulfide and 30% HBr/AcOH (1:1, 4 ml).

After 4 hours, ether was added to precipitate the product which was collected by filtration and air dried. This was dissolved in methanol and analyzed by analytical HPLC using a 3.9×300 mm c18 column and a 30 minute gradient of 10–100% acetonitrile/water each containing 0.05% TFA at a flow rate of 1 ml/min and UV detection at 260 nm. The product was found to elute at 15 minutes while the starting material eluted at 24 minutes. Approximately, 60% of the crude material was purified by preparative HPLC and the HPLC fractions were lyophilized to dryness. Yield=42 mg (80%). MALDI-TOF MS 432.87 obs. (432.45 calc.).

Synthesis of (2',6'-dimethyl-4'carboxyl)phenyl 2-phos-phoryloxy-7-methoxy-10-methyl-acridinium-9-carboxylate (9)

Crude deblocked acridinium ester from above (80 mg) was dissolved in pyridine (25 ml) and treated with phosphorus oxychloride (3×75 µl, ~15 equivalents) at 0° C. under nitrogen. The reaction was stirred for 1 hour and then quenched with water (3 ml) and stirred for an additional hour at room temperature. The reaction was then concentrated to a small volume. HPLC analysis using the same conditions as above but with a 40-minute gradient of 10–60% acetonitrile/water (each with 0.05% TFA) showed product eluting at 20 minutes with starting material eluting at 24 minutes. The product was isolated by preparative HPLC and the HPLC fractions were lyophilized to dryness. Yield=3 mg yellow powder. MALDI-TOF MS 513.00 obs. (513.26 calc.).

EXAMPLE 10

Synthesis of 2-OH-Spiroacridan (12) and 2-Phos-Spiroacridan (11)

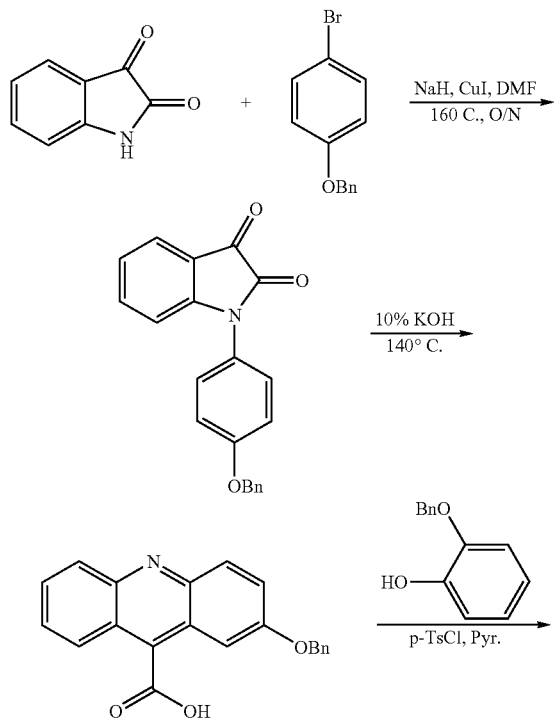

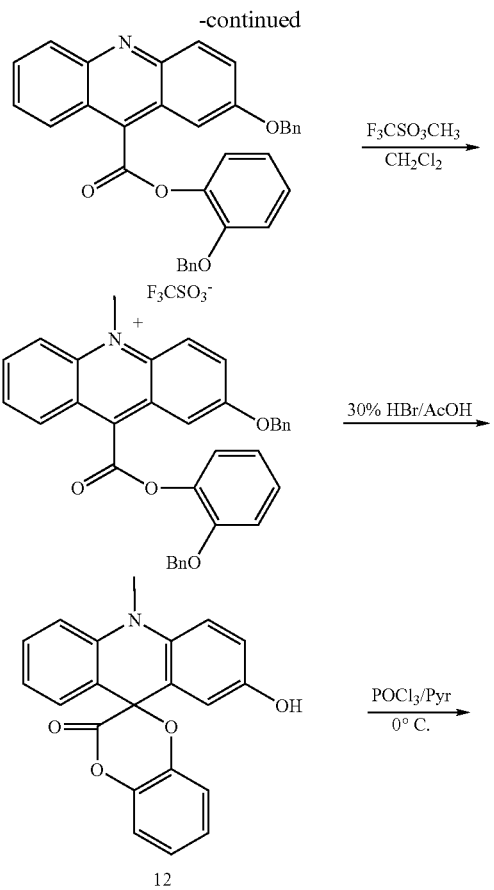

N-(4'-Benzyloxy)phenylisatin

To a solution of isatin (4 g, 27.2 mmol) in DMF (50 ml) under nitrogen at room temperature was added NaH (871 mg, 34.5 mmol). The reaction color changed from orange to purple. It was stirred at room temperature for 30 min before 4-benzyloxyphenyl bromide (10.21 g, 38.8 mmol) and CuI (10.34 g, 54.4. mmol) were added. It was refluxed at 160° C. in an oil-bath for 20 hours under nitrogen. After cooling to room temperature, the reaction was poured into chloroform (400 ml), and filtrated. The filtrate was concentrated to dryness under reduced pressure to give the desired product as a brown gum. It was used in the next step without further purification.

2-Benzyloxyacridine-9-carboxylic acid

The above mixture in 10% KOH/H$_2$O (220 ml) was refluxed at 130° C. for 20 hours. The reaction was filtered while warm, and the filtrate was cooled to 0° C. before it was acidified with concentrated HCl to pH 3. The yellow precipitate was filtered, and the filter cake was washed with water (4×200 ml). It was dried under reduced pressure at 50° C. for 20 hours. The desired product was obtained in 1.8 g. It was confirmed by MS (MALTI-TOF): m/z 331 (M+1).

(2'-Benzyloxy)phenyl
2-benzyloxyacridine-9-carboxylate

A solution of 2-benzyloxyacridine-9-carboxylic acid (306 mg, 0.93 mmol) in pyridine (30 ml) was treated with p-toluenesulfonyl chloride (276 mg, 1.45 mmol) at room temperature under nitrogen for 30 min before 2-(benzyloxy) phenol was added. The reaction was stirred at room temperature for 20 hours. It was concentrated to dryness under reduced pressure. The resulting material was purified on a flash column eluted with gradient solvent system of ethyl acetate/hexane starting at 10%. The product came out at 20%. The desired fractions were combined and concentrated to dryness under reduced pressure to give 226 mg of the desired product. It was confirmed by MS (MALTI-TOF): m/z 513 (M+1).

(2'-Benzyloxy)phenyl
2-benzyloxy-10-methyl-acridine-9-carboxylate
trifluoromethanesulfonate A solution of (2'-benzyloxy)phenyl 2-benzyloxyacridine-9-carboxylate (109 mg, 0.213 mmol) in dichloromethane (5 ml) was treated with methyl trifluoromethanesulfonate (260 μL, 2.30 mmol) under nitrogen at room temperature for 20 hours. The reaction was blown to dryness with nitrogen followed by suspending in ether. The yellow precipitate was washed with more ether (4×10 ml). The resulting solid was dried under reduced pressure to give 71.35 mg of the desired product.

2-OH-Spiroacridan (11)

A mixture of (2'-benzyloxy)phenyl 2-benzyloxy-10-methyl-acridine-9-carboxylate (30 mg, 0.043 mmol) in 30% HBr/AcOH (400 μL) was stirred at 45° C. for 1 hour. It was blown with nitrogen to dryness followed by suspending in ether. The solid was filtered, washed with more ether (4×10 ml), and dried under reduced pressure to give 17 mg of the desired product. A portion of this product (11 mg) was purified on a preparative HLPC column (YMC, 250×20 mm I.D., ODS, 10 μm). The column was eluted in gradient by mixing 0.05% TFA/water (solvent A) and 0.05% TFA/acetonitrile (solvent B) in the following manner: 10 to 60% B in 40 minutes, flow rate at 16 ml/minute, monitored at 260 nm. The fraction at retention time of ~25 minutes was collected and lyophilized to dryness to give the pure product in 7.3 mg. It was confirmed by MS (MALTI-TOF): m/z 347 (M+1).

2-Phos-Spiroacridan (12)

To a solution of the above 2-OH-Spiroacridan (5.66 mg, 0.016 mmol) in pyridine (0.5 ml) at 0° C. under nitrogen was added POCl$_3$ (7.65 μl, 0.082 mmol). It was stirred at the same temperature for 1 hour then quenched with water (0.5 ml) and stirred for another 15 min. It was concentrated to dryness under reduced pressure, followed by purification on a preparative HLPC column (YMC, 250×20 mm I.D., ODS, 10 μm). The column was eluted in gradient by mixing 0.05% TFA/water (solvent A) and 0.05% TFA/acetonitrile (solvent B) in the following manner: 10 to 60% B in 40 minutes, flow rate at 16 ml/minute, monitored at 260 nm. The fraction at retention time of ~18 minutes was collected and lyophilized to dryness to give the pure product in 2.3 mg. It was confirmed by MS (MALTI-TOF): m/z 427 (M+1).

EXAMPLE 11

Synthesis of (2',6'-dimethyl-4'-carboxyl)phenyl
3-(β-phosphoryloxy-4'-hydroxystyryl)-10-methyl
acridinium-9-carboxylate trifluoromethanesulfonate
(3-Enol-Phos-DMAE, 13) and its corresponding
acridan (3-Enol-Phos-acridan, 15)

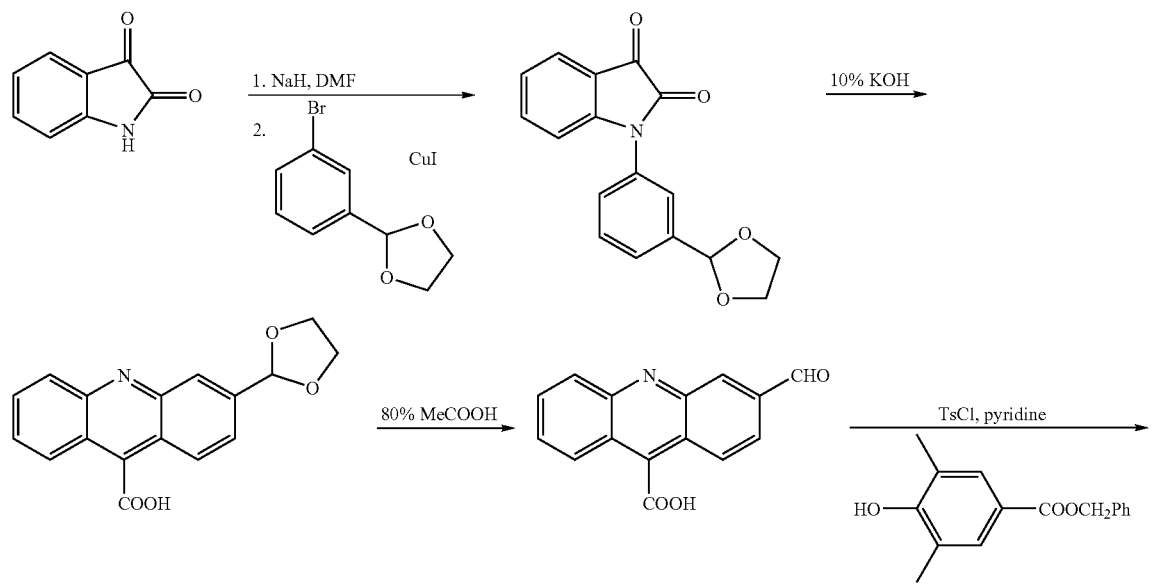

-continued
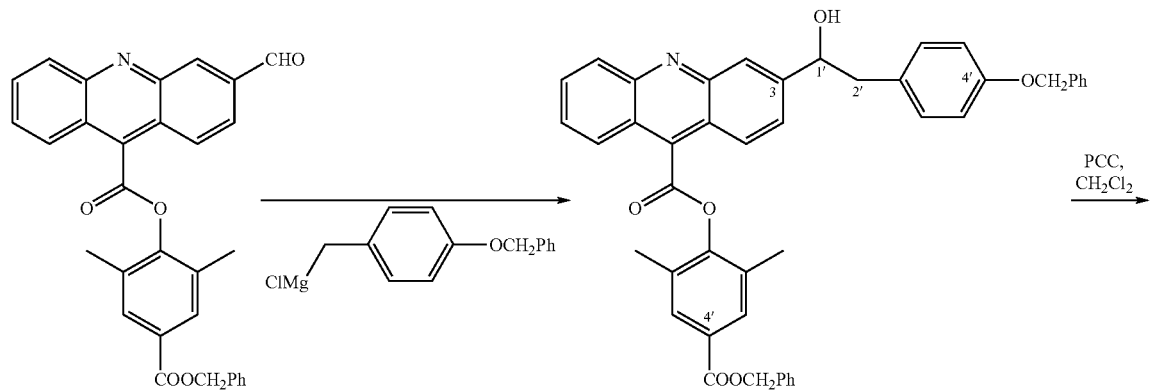
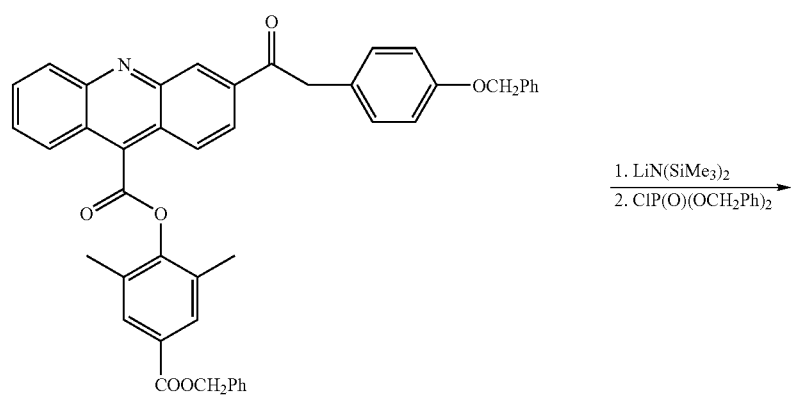
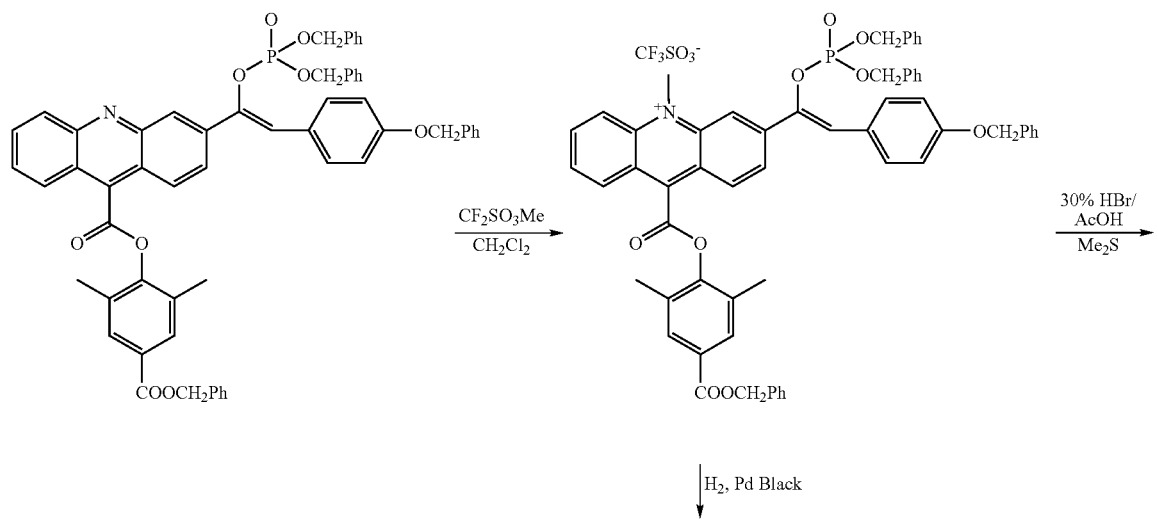

-continued

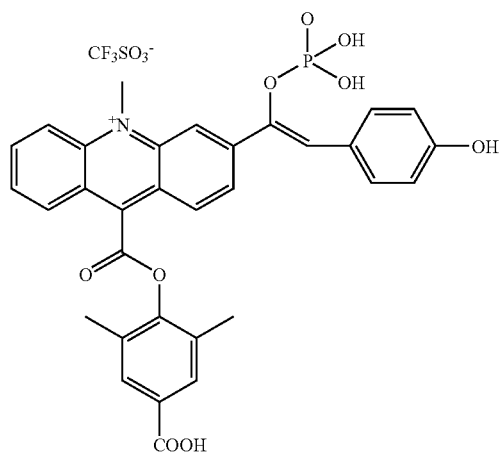

13

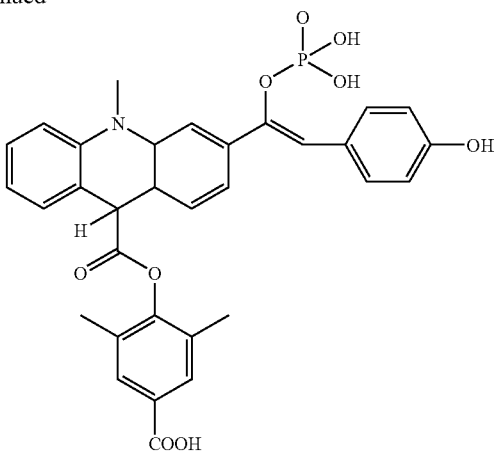

15

Synthesis of N-[3-(1,3-dioxolyl)phenyl]isatin

Isatin (3.2 g, 0.0218 mol) was dissolved in anhydrous DMF (75 ml) and cooled in an ice-bath under a nitrogen atmosphere. To this cold solution, sodium hydride (0.575 g, 0.0239 mol) was added and the reaction was stirred at 0° C. for 1.5 hours. This solution was then treated with 2-(3-bromophenyl)-1,3-dioxolane (5 g, 1 equivalent) followed by CuI (8.3 g, 2 equivalents). The resulting suspension was heated in an oil-bath under nitrogen at 130–140° C. for 16 hours. It was then cooled to room temperature and diluted with an equal volume of chloroform. This suspension was filtered and the filtrate was concentrated under reduced pressure. A viscous brown oil was recovered which was suspended in xylenes (150 ml) wand evaporated to dryness. The residue was used as such for the next reaction. TLC (5% methanol in chloroform) showed clean conversion; Rf (product)=0.86.

Synthesis of 2-(9'-carboxyacridin-3'-yl)-1,3-dioxolane

Crude N-[3-(1,3-dioxolyl)phenyl]isatin from above was suspended in 10% KOH (150 ml) and the resulting suspension was refluxed under nitrogen for 4.5 hours. The reaction was then cooled to room temperature and filtered. The filtrate was diluted with ice and acidified with 20–30% HCl until weakly acidic. A yellow precipitate separated out which was collected by filtration and air dried. Yield ~5 g, yellow sticky solid which was used as such for the next reaction.

Synthesis of acridine-9-carboxylic acid-3-carboxaldehyde

Crude 2-(9'-carboxyacridin-3'-yl)-1,3-dioxolane (~5 g) was suspended in 80% aqueous acetic acid (100 ml). This suspension was heated at 80° C. under nitrogen for 16 hours. A yellow precipitate had appeared in the reaction. The reaction mixture was then cooled to room temperature and diluted with anhydrous ether (~500 ml). The precipitated solid was collected by filtration, rinsed with ether and air dried. It was then transferred to a round bottom flask, suspended in toluene (50 ml) and evaporated to dryness. This process was repeated once more. A bright yellow solid was recovered. Yield=1.72 g (31% overall). MALDI-TOF MS 252.3 obs. (251.24 calc.).

Synthesis of (2',6'-dimethyl-4'-benzyloxycarbonyl) phenyl acridine-9-carboxylate-3-carboxaldehyde Acridine-9-carboxylic acid-3-carboxaldehyde (0.3 g, 0.0012 mol) in pyridine (50 ml) was cooled in an ice-bath under nitrogen and treated with p-toluenesulfonyl chloride (0.456 g, 0.00239 mol). The reaction was stirred at 0° C. for 15 minutes and then 2,6-dimethyl-4-benzyoxycarbonyl-phenol (0.306 g, 1 equivalent) was added. The reaction was warmed to room temperature and stirred for 48 hours under nitrogen and then concentrated under reduced pressure. The residue was dissolved in chloroform which was then washed with aqueous bicarbonate and aqueous ammonium chloride. The organic layer was separated, dried over magnesium sulfate and concentrated under reduced pressure. The crude residue (0.6 g) was purified by preparative TLC on silica using 10% ethyl acetate in chloroform; Rf (product)=0.6. Yield=0.24 g (41%); bright yellow solid. MALDI-TOF MS 490.78 obs. (489.53 calc.); $^1$H-NMR (CDCl$_3$): δppm 2.46 (s, 6H), 5.40 (s, 2H), 7.37–7.50 (m, 5H), 7.78 (m, 1H), 7.94 (m, 3H), 8.12 (d, 1H, J=9.3 Hz), 8.39 (d, 1H, J=8.6 Hz), 8.45 (d, 1H, J=8.6 Hz), 8.51 (d, 1H, J=9.2 Hz), 8.79 (s, 1H), 10.31 (s, 1H).

Synthesis of (2',6'-dimethyl-4'-benzyloxycarbonyl) phenyl 3-[1'-hydroxy-2'-(4'-benzyoxyphenyl)ethyl]-acridine-9-carboxylate Benzyloxybenzyl chloride (1 g, 0.0043 mol) in anhydrous THF (20 ml) was treated with Mg turnings (~0.5 g) which had been broken into smaller pieces to expose fresh surfaces. Upon slight warming, the Grignard reaction started and was cooled with cold water until the reaction was complete. The solution of the Grignard reagent was then cooled in a dry ice-acetone bath and then added slowly via a syringe to a solution of the aldehyde from above (0.5 g, 0.001 mol) in THF (10 ml) which had been cooled thoroughly in a dry ice-acetone bath under nitrogen. The reaction was stirred at −78° C. for 30 minutes by which time TLC showed complete consumption of the starting material. The reaction was then diluted with ethyl acetate (50 ml) and the resulting solution was poured into cold aqueous ammonium chloride (~2%, 200 m). The organic layer was separated, dried over magnesium sulfate and evaporated to dryness. The crude residue was purified by preparative TLC on silica using 1:4 ethyl acetate in hexane. The product was recovered as a yellow solid and was used as such for the next reaction. Yield=0.38 g (54%).

Synthesis of (2',6'-dimethyl-4'-benzyloxycarbonyl) phenyl 3-(4'-benzyloxyphenylacetyl)-acridine-9-carboxylate The alcohol from above (0.38 g, 0.55 mmol) in dichloromethane (30 ml) was treated with PCC (0.18 g, ~5 equivalents). The reaction was stirred at room temperature under nitrogen. After 1 hour an additional 10 equivalents PCC was added. After 2 hours, the reaction was diluted with ethyl acetate (25 ml) and filtered. The filtrate was concentrated under reduced pressure. The residue was purified by preparative TLC on silica using 5% ethyl acetate in chloroform. The product was recovered as a bright yellow solid. Yield=80 mg (20%). $^1$H-NMR (CDCl$_3$): δppm 2.46 (s, 6H), 4.47 (s, 2H), 5.04 (s, 2H), 5.39 (s, 2H), 6.97 (d, 2H, J=8.7 Hz), 7.26–7.49 (m, 10H), 7.76 (dd, 1H), 7.90 (dd, 1H), 7.95 (s, 2H), 8.23 (d, 1H, J=9.3 Hz), 8.39 (d, 1H, J=8.7 Hz), 8.45 (d, 1H, J=6.9 Hz), 8.48 (d, 1H, J=9.3 Hz), 9.02 (s, 1H). MALDI-TOF MS 687.27 obs. (686.78 calc.).

Synthesis of (2',6'-dimethyl-4'-benzyloxycarbonyl) phenyl 3-(β-dibenzylphosphotriester-4'-benzyloxy-styryl)-acridine-9-carboxylate Dibenzyl phosphite (0.263 g, 0.001 mol) in anhydrous benzene (4 ml) was treated with N-chlorosuccinimide (0.134 g, 1 equivalent). The reaction was stirred at room temperature under nitrogen for 1 hour. The acridine ester ketone from above (80 mg, 0.117 mmol) was dissolved in anhydrous THF (5 ml) and cooled to −78° C. under nitrogen in a dry ice-acetone bath and lithium bis(trimethylsilyl)amide (0.6–0.7 ml of 1.0 M) was added dropwise via a syringe. A purple solution was formed which was stirred in the dry ice-acetone bath for 20 minutes and then the benzene solution of dibenzylphosphochloridate was added dropwise and then warmed to room temperature. After ~15 minutes, the dark purple color of the reaction faded to a dark yellow solution which was diluted with ethyl acetate (25 ml), and then washed twice with aqueous ammonium chloride (~2%). The organic layer was dried over magnesium sulfate and evaporated to dryness. The product was purified by preparative TLC using 2:3 ethyl acetate in hexane. Yield=59 mg (53%), orange-yellow oily solid. $^1$H-NMR (CDCl$_3$): δppm 2.47 (s, 6H), 4.91 (m, 4H), 5.07 (s, 2H), 5.39 (s, 2H), 6.76 (s, 1H, vinyl), 6.97 (d, 2H), 7.15–7.50 (m, 20H), 7.69 (m, 2H), 7.87 (m, 1H), 7.96 (s, 2H), 8.34 (d, 1H), 8.41 (d, 1H), 8.57 (s, 1H). MALDI-TOF MS 947.11 obs. (947.01 calc.).

Synthesis of (2',6'-dimethyl-4'-benzyloxycarbonyl) phenyl 3-(β-dibenzylphosphotriester-4'-benzyloxy-styryl)-10-methyl-acridinium-9-carboxylate trifluoromethanesulfonate The acridine enol-phosphate triester from above (59 mg, 0.0624 mmol) was dissolved in dichloromethane (5 ml) and treated with methyl trifluoromethanesulfonate (71 μl, 10 equivalents). The reaction was stirred at room temperature for 16 hours. HPLC analysis of the reaction mixture on a 3.9×300 mm, C18 column and a 30-minute gradient of 10–100% acetonitrile/water each containing 0.05% TFA at a flow rate of 1 ml/min. and UV detection at 260 nm; indicated product eluting at 19.2 minutes (60% conversion). The product was isolated by preparative HPLC and the HPLC fractions were concentrated under reduced pressure. The acridinium ester was isolated as a purple solid. Yield=29 mg (43%). MALDI-TOF MS 962.11 obs. (962.04 calc.).

Synthesis of (2',6'-dimethyl-4'-carboxyl)phenyl 3-(β-phosphoryloxy-4'-hydroxystyryl)-10-methyl acridinium-9-carboxylate trifluoromethanesulfonate (13)

The tetrabenzyl-protected acridinium ester from above (12.8 mg, 0.012 mmol) was dissolved in methyl sulfide (1 ml) and treated with 30% HBr in acetic acid. The reaction was stirred at room temperature. After 4 hours, ether (20 ml) was added and the precipitated solid was collected by filtration. The product was dissolved in methanol (10 ml) and analyzed by analytical HPLC (see above) which indicated clean conversion to product eluting at ~16 minutes. The product was isolated by preparative HPLC. The HPLC fractions were concentrated to a small volume by rotary evaporation and then lyophilized to dryness. Yield=6 mg (71%). MALDI-TOF MS 601.34 obs. (600.54 calc.).

Synthesis of (2',6'-dimethyl-4'-carboxyl)phenyl 3-(β-phos-phoryloxy-4'-hydroxystyryl)-10-methyl acridan (15)

Crude tetrabenzyl-protected acridinium ester (~40 mg) was dissolved in a mixture of methanol (14 ml), acetone (5 ml) and 0.1 M ammonium acetate pH 6.9 (1.5 ml). This solution was treated with palladium black (18 mg). The resulting suspension was hydrogenated at room temperature using a balloon, and after 3–4 hours, a light green solution was obtained. The reaction was then filtered and the filtrate was concentrated to a small volume and half the material was purified by preparative HPLC using a 25 min. gradient of 30 to 90% methanol in water (each containing 0.05% TFA) on a C18 column (30×250 mm) and UV detection at 260 nm. The product eluted as a broad peak at ~26.5 minutes. The HPLC fraction containing product was concentrated to dryness to afford a purple solid. Yield=8 mg. MALDI-TOF MS 600.25 obs. (601.55 calc.).

EXAMPLE 12

Enzymatic conversion of (2',6'-dimethyl-4'-carboxyl)phenyl 3-(β-phosphoryloxy-4'-hydroxystyryl)-10-methyl acridinium-9-carboxylate trifluoromethanesulfonate (13) to its keto product [3-(4'-Hydroxybenzyl)carbonyl-DMAE, 14]

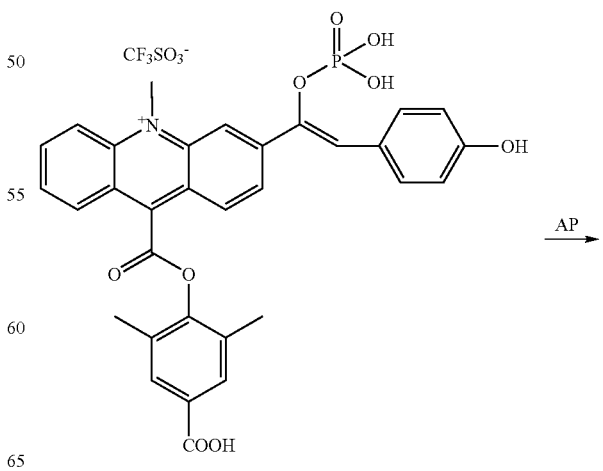

13

-continued

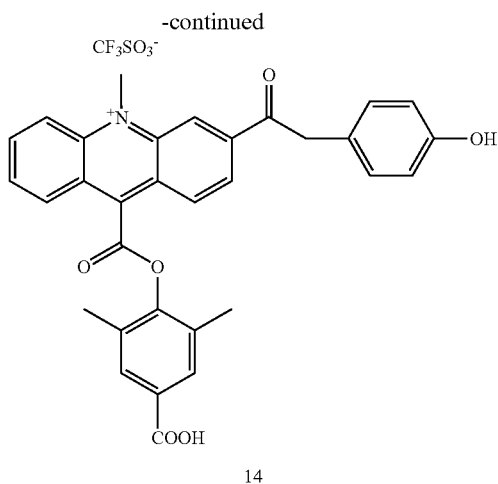

14

A 1 mM DMF solution of the acridinium 3-enol-phosphate (13) was mixed with 150 μL of 100 mM Tris pH 9 also containing 1 mM MgCl$_2$. Alkaline phosphatase (5 μl of a 2 mg/ml solution) was added and the reaction was incubated at room temperature for ~1 hour. HPLC analysis using a 3.9×300 mm C18 column and a 30-minute gradient of MeCN in water, each containing 0.05% TFA, at a flow rate of 1 ml/min and UV detection at 260 nm, indicated a complete conversion; Rt (starting material)=16 min, Rt (product)=20 min. The product was isolated by semi-preparative HPLC using a 7.8×300 mm, C18 column. MALDI-TOF MS of the product indicated this was indeed the keto product (14): m/z 521.36 obs. (520.56 calc.).

EXAMPLE 13

Enzymatic conversion of (2',6'-dimethyl-4'-carboxyl)phenyl 3-(β-phosphoryloxy-4'-hydroxystyryl)-10-methyl acridan (3-Enol-Phos-acridan, 15) to its keto product [3-(4'-Hydroxybenzyl)carbonyl-acridan, 16]

-continued

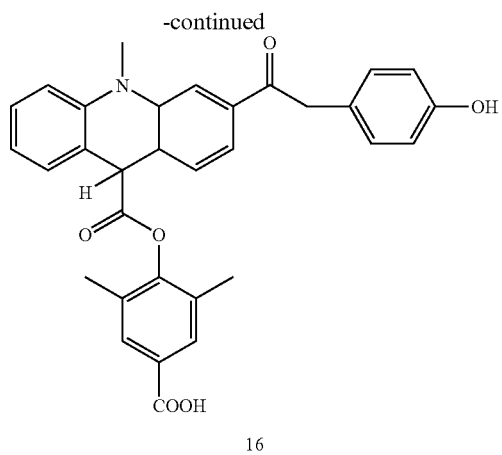

16

A 20 μL DMF solution of the acridan (15) (1.7 mM) was combined with 180 μl of 0.15 M 2-amino-2-methyl-1-propanol pH 10.3 also containing 1 mM magnesium acetate. A clear blue solution was obtained (0.17 mM substrate), which was then treated with alkaline phosphatase ($10^{-10}$ moles). The blue color was discharged instantly. After one hour, HPLC analysis using a C18 column (3.9×300 mm) and a 40-minute gradient of from 10 to 90% MeCN/water each containing 0.05% TFA at a flow rate of 1 mL/min and UV detection at 260 nm indicated a clean conversion to a later eluting product at 21.3 minutes (the starting material elutes at 19.3 minutes). The reaction mixture was then evaluated by the FSSS to determine the light emission spectrum of the product, which is shown in FIG. 2N. The product was isolated by semi-preparative HPLC. MALDI-TOF MS indicated that this was indeed the acridan keto compound (16): m/z 521.67 obs. (521.56 calc.).

EXAMPLE 14

Synthesis of 4'-hydroxyphenyl 10-methyl acridinium-9-carboxylate trifluoromethanesulfonate (4'-OH-AE, 18)

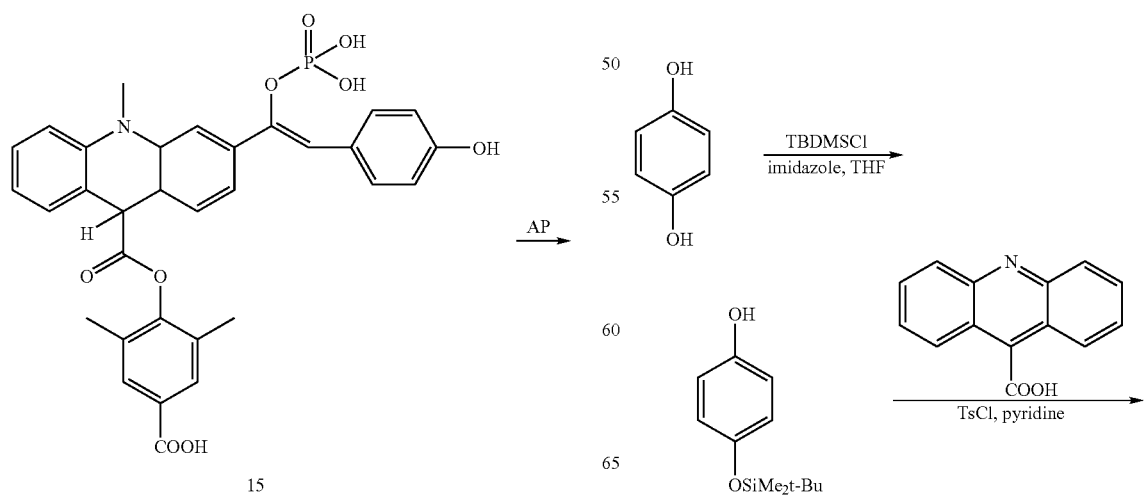

-continued

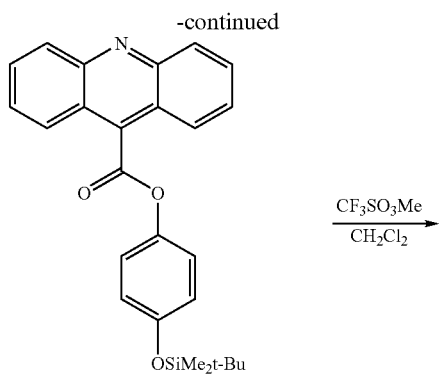

Synthesis of 1,4-dihydroxybenzene mono-tert-butyldimethyl-silyl ether

Hydroquinone (0.5 g, 0.0045 mol) in THF (25–30 ml) under nitrogen was treated with imidazole (0.434 g, 1.5 equivalents) and tert-butyldimethylchlorosilane (0.686 g, 1 equivalent). The reaction was stirred at room temperature under nitrogen. A precipitate appeared instantly upon addition of the chlorosilane. After 3–4 hours, the reaction was diluted with ethyl acetate and washed with aqueous sodium bicarbonate (~2%) and brine. It was then dried over magnesium sulfate and evaporated to dryness. The product was purified by preparative TLC using 25% ethyl acetate in hexanes. The product was obtained as an oil. Yield=0.5 g (50%).

Synthesis of 4'-tert-butyldimethylsilyloxyphenyl acridine-9-carboxylate

Acridine-9-carboxylic acid (0.29 g, 0.0013 mol) in anhydrous pyridine (10 ml) was cooled in ice under nitrogen and treated with p-toluenesulfonyl chloride (0.595 g, 2 equivalents). After ~10 minutes stirring in ice, hydroquinone mono-tertbutyldiemethylsilyl ether (0.29 g) was added. The reaction was warmed to room temperature and stirred under nitrogen for 16 hours. The reaction was then evaporated to dryness. The residue was dissolved in ethyl acetate (50 ml) and washed with aqueous sodium bicarbonate (~2%). The ethyl acetate layer was dried over magnesium sulfate and evaporated to dryness. The crude product was purified by preparative TLC on silica using 25% ethyl acetate in hexanes. Yield=0.25 g (45%). MALDI-TOF MS 431.61 obs. (429.58 calc.).

Synthesis of 4'-hydroxyphenyl 10-methyl acridinium-9-carboxylate trifluoromethanesulfonate (18)

The acridine ester from above 90.25 g, 0.58 mmol) in dichloromethane (~10 ml) was treated with methyl trifluoromethanesulfonate (0.66 ml, 10 equivalents). The reaction was stirred at romm temperature for 16 hours. Ether was then added to precipitate the product which was collected by filtration. A yellow powder was obtained. Yield=0.19 g. MALDI-TOF MS 330.68 obs. (330.36 calc.).

EXAMPLE 15

Synthesis of 4'-phosphophenyl 10-methyl acridinium-9-carboxylate trifluoromethanesulfonate (4'-Phos-AE, 17)

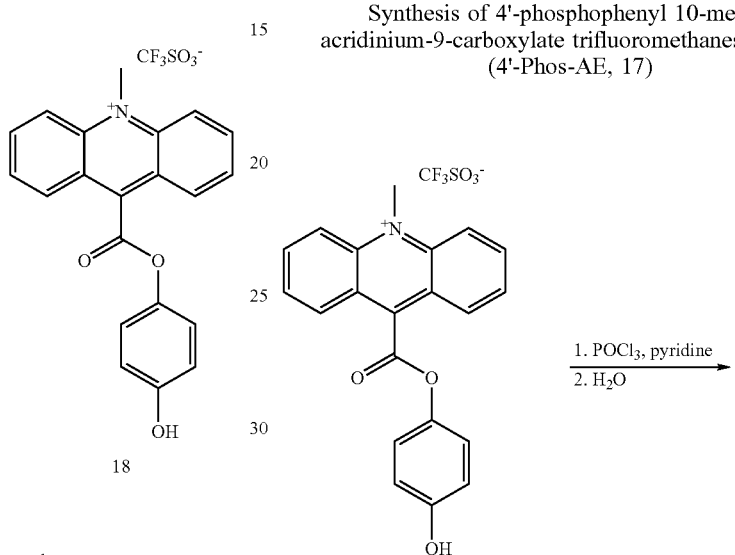

4'-Hydroxyphenyl 10-methyl acridinium-9-carboxylate trifluoromethanesulfonate from above (32 mg, 0.069 mmol) was dissolved in pyridine (1 ml) and cooled in an ice-bath under nitrogen. Phosphorus oxychloride (45 µl, 5 equivalents) was added and the reaction was stirred in ice for 30 minutes. The reaction was then poured into ice-cold water (950 ml) containing 0.25 ml 5N NaOH. After stirring briefly, this solution was extracted with chloroform and then ethyl acetate. The aqueous solution was then lyophilized to dryness. A bright yellow powder was obtained which was analyzed by HPLC on a 3.9×300 mm C18 column and a 40 minute gradient of 10–90% acetonitrile/water, each containing 0.05% TFA at a flow rate of 1 ml/min. and UV detection at 260 nm. The product eluted at 12 minutes with very little starting material at 15 minutes. The product was purified by preparative HPLC and the HPLC fraction was lyophilized to dryness. Yield=14 mg yellow, fluffy powder. MALDI-TOF MS 411.13 obs. (410.33 calc.).

EXAMPLE 16

Alkaline Phosphatase Assay Using 2-Phos-DMAE (1) (45° C., 0.5 hour)

The substrate solution of 2-Phos-DMAE (1) was prepared at 0.1 mM in 100 mM, pH 9.0 Tris buffer containing 1 mM $MgCl_2$. The alkaline phosphatase standards, Sigma Cat. No. P-3681, activity 4900 units (DEA)/mg protein, were prepared in water. Two μl each of alkaline phosphatase standards was incubated with 48 μl of the substrate solution at 45° C. for 0.5 hour, with 2 μL of water as a zero control. The solutions were then diluted 100 fold with 100 mM, pH 9.0 Tris buffer containing 1 mM $MgCl_2$, respectively. Each diluent (25 μl) was flashed, in 5 replicates, with 300 μl of 0.25 N NaOH containing 0.5% CTAB immediately followed by 300 μl of 0.5% $H_2O_2$. The light outputs were measured for 2 seconds on Bayer Diagnostics Magic Lite Analyzer 1 (MLA-1) equipped with R268 PMT and two LL650 long wavelength pass filters (Corion, Lot No. CFS-002645). The result is shown in FIG. 10. The diluents were also flashed on MLA-1 equipped with R2228P PMT and two LL650 long wavelength pass filters, and the unit was pre-cooled in a cold room (4° C.). The result is given in FIG. 11.

EXAMPLE 17

Alkaline Phosphatase Assay Using 2-Phos-DMAE (1) (45° C., 1 hour)

According to Example 16, an assay of alkaline phosphatase was carried out by adding 5 μl of the AP standard to 95 μl of the substrate solution. The solutions were incubated at 45° C. for 1 hour, and then diluted 100 fold with the Tris buffe. The diluent (25 μl) was flashed in 3 replicates with 300 μl of 0.25 N NaOH containing 0.5% CTAB immediately followed by 300 μl of 0.5% $H_2O_2$. The light outputs were measured for 2 seconds on MLA-1 equipped with R2228P PMT and a LL700 long wavelength pass filters, and the unit was pre-cooled in a cold room (4° C.). The result is given in FIG. 12.

EXAMPLE 18

Alkaline Phosphatase Assay Using 4'-phosphoryloxyphenyl-10-methyl acridinium-9-carboxylate (4'-Phos-AE, 17)

Figure 13:
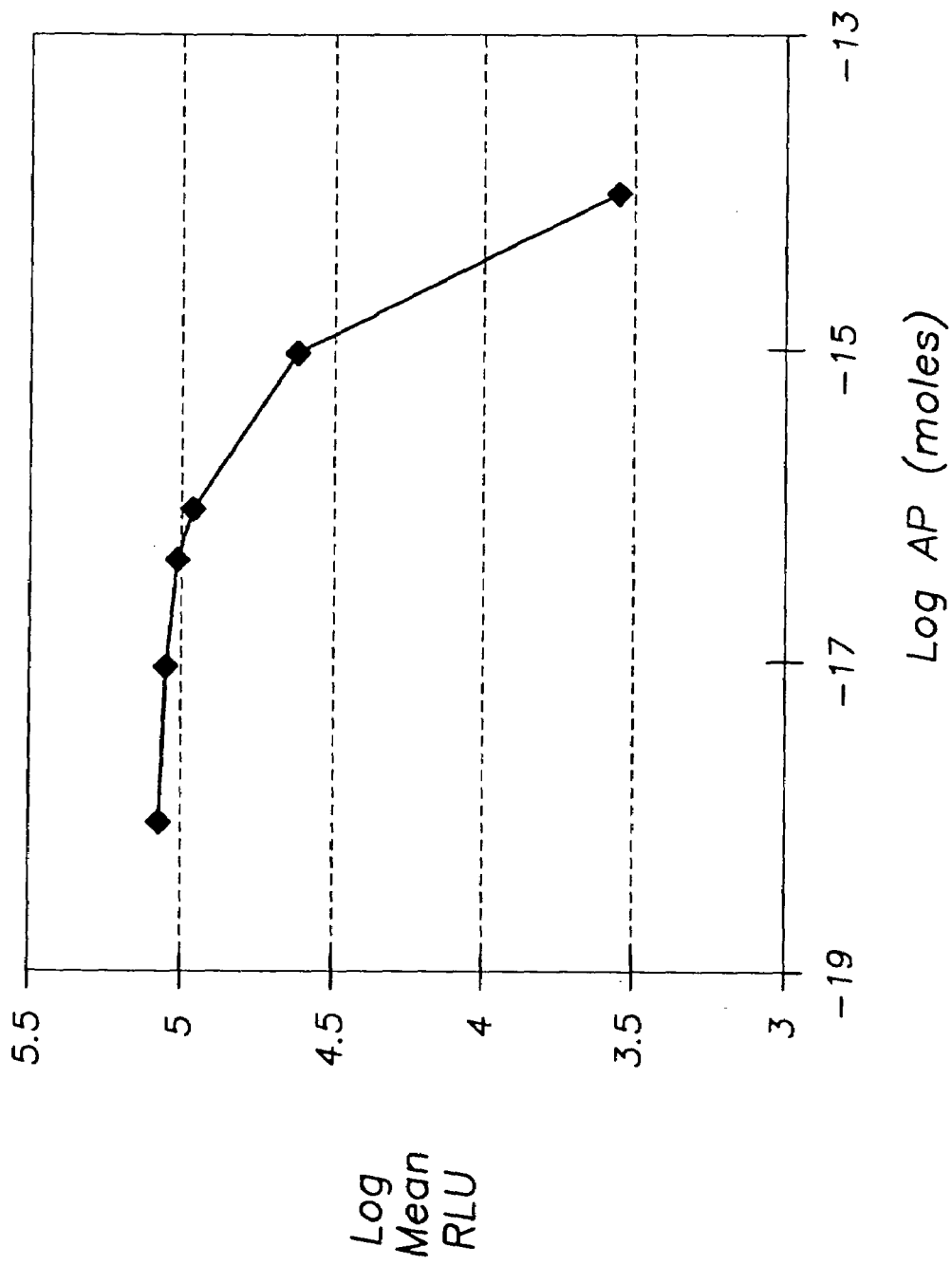
FIG. 13 is a plot of showing the detectability of alkaline phosphatase using 4'-Phos-AE (FIG. 1Q) as the substrate.

Treatment of a solution of 4'-Phos-AE (17, 0.1 mM,) in 100 mM Tris pH 9, 1 mM $MgCl_2$ with varying concentrations of alkaline phosphatase was carried out. The reactions were incubated for 3–4 hours at room temperature and were then sequentially diluted $10^4$-fold into 'flash buffer' which contains 10 mM phosphate pH 8 with 150 mM NaCl, 0.1% BSA and 0.05% sodium azide. Chemiluminescence of a 25 μL solution was measured on a Bayer Diagnostics' Magic Lite Ananlyzer (MALL) equipped with a BG38 filter. A measuring time of 0.3 s was employed. Evaluation of the chemiluminescent activity of the reactions indicated a steady decrease in total chemiluminesence with increasing concentrations of enzyme. Thus, as the concentration of enzyme is increased, a greater proportion of the fast-emitting substrate 4'-Phos-AE is converted to the slow-emitting product 4'-OH-AE (18) leading to an overall decrease in light output (at a short measuring time). The dose-response curve was also found to be sigmoidal in shape (a log-log plot is shown in FIG. 13). Alkaline phosphatase was easily detected at $5 \times 10^{-17}$ moles (0.1 ml reaction volume) in this assay.

EXAMPLE 19

Preparation of Anti-αTSH-Alkaline Phosphatase Conjugate

Thiolation of Murine, Monoclonal Anti-TSH

Murine, monoclonal antibody (32 nmole, 4.95 mgs) with binding affinity for the α-subunit of human thyroid stimulating hormone (TSH) was derivatized with 2-iminothiolane (0.32 pmole, 10 equivalents) in 0.10 M $Na_2HPO_4$, 0.15 M NaCl, 5.0 mM EDTA, pH 8.1 for 1 h. at ambient temperature. The thiolated anti-αTSH was isolated in the void volume of a Sephadex® G-25 fine column (1.5 cm i.d.×80 mLs) in 0.10 M $Na_2HPO_4$, 0.15 M NaCl, 5.0 mM EDTA, pH 7.0. The yield was 4.65 mgs protein (93.4% recovery). Thiol incorporation as determined by MALDI-TOF MS was 3.8 per anti-αTSH.

Maleimide Activation of Alkaline Phosphatase

Calf intestinal alkaline phosphatase (EC 3.1.3.1) (39 nmole, 5.50 mgs) with a specific activity of 3,880 pNPP U/mg was derivatized with sulfosuccinimydyl 4-(N-maleimidomethyl) cyclohexane 1-carboxylate (sulfo-SMCC) (89 nmole, 2.3 equivalents) in 0.10 M $Na_2HPO_4$, 0.15 M NaCl, 5.0 mM EDTA, pH 7.0 for 1 h. at ambient temperature. The maleimido-alkaline phosphatase was isolated by retentive, centrifugal ultrafiltration on a 30 kD molecular weight cutoff filter with multiple buffer exchange cycles in 0.10 M $Na_2HPO_4$, 0.15 M NaCl, 5.0 mM EDTA, pH 7.0. The yield was 4.64 mgs protein (84.4% recovery). Maleimide incorporation as determined by MALDI-TOF MS was 1.0 maleimide per alkaline phosphatase.

Conjugation of Maleimido-Alkaline Phosphatase to Thiolated Anti-αTSH

Maleimido-alkaline phosphatase (12 nmole, 0.62 equivalents) was coupled to thiolated anti-αTSH (19.4 nmole) in 0.10 M $Na_2HPO_4$, 0.15 M NaCl, 5.0 mM EDTA, pH 7.0 for-16 h. at 4° C. The conjugate was isolated by SEC on a Sephadex® G-200 column (1.5 cm i.d.×125 mLs, 40–120 μm) in 0.10 M Tris, 0.15 M NaCl, pH 7.4 at ambient temperature. Univalent conjugation was confirmed by MALDI-TOF.

EXAMPLE 20

A Heterogeneous, Immunoassay Demonstrating 2-Phos-DMAE (1) Utility as a Substrate for the Chemiluminescent Detection of TSH in Human Serum.

Diagnostic assay applicability of 2-Phos-DMAE as a chemiluminescent substrate was evaluated using a divalent, sandwich enzyme-immunoassay (EIA) formulated for the clinical quantitation of TSH in serum. In this assay the alkaline phosphatase-anti-αTSH conjugate (henceforth referred to as a tracer) should bind specifically to the selected analyte, the α-subunit of intact human TSH, present in a patient sample or a TSH-containing standard (Bayer Diagnostics Corp., Walpole, Mass.), to form a noncovalently associating antibody-antigen complex. The tracer-analyte complex is in turn captured by a magnetic bead solid phase, covalently coupled to a second, murine, monoclonal antibody with binding affinity for the β-subunit of intact human TSH. Bound tracer is magnetically separated from unbound tracer, and quantified by enzymatic hydrolysis of the applied chemiluminescent substrate. Standard curve data were used to calculate the TSH concentration of several control samples.

The tracer was diluted to a working concentration of 1.0 nM in ACS™ TSH3 Lite Reagent Buffer (Bayer Diagnostics Corp., Walpole, Mass.). The TSH assay was initiated when 100 μl of the tracer were mixed with 200 μl of either a TSH standard or control. Eight TSH standards were used, containing TSH in concentrations of 0.000, 0.120, 0.740, 1.92, 3.86, 8.99, 19.9, and 49.6 μI.U./ml (Bayer Diagnostics Corp., Walpole, Mass.). Three controls were also assayed. These were Ligands 1, 2 and 3 from Bayer Diagnostics, which contained TSH in mean concentrations of 0.60, 5.1 and 18.4 μI.U./ml, respectively. The mixtures were collectively vortexed thrice for five seconds at setting number five on a Corning, Inc. model 4010 Multi-Tube Vortexer. Data points were acquired in triplicate. The assay mixtures were then incubated for thirty minutes at room temperature, after which 225 μl of anti-βTSH MLP solid phase (~56 μgs) was added to each assay. The assay mixtures were vortexed thrice as described above and incubated for thirty minutes at room temperature. The solid phase was magnetically separated from the supernatant by the three-minute application of an array of permanent magnets in a Bayer Magic Lite Assay Rack. The supernatant was decanted from the solid phase. Residual supernatant was removed by blotting for three minutes and then again for one minute. The solid phase was washed with two separate 1.0 ml volumes of water and suspended in 100 μl of substrate solution containing 0.10 mM 2-Phos-DMAE (1) in 100 mM Tris, 1.0 mM $MgCl_2$, pH 9.0. The enzyme reaction was carried out for 1 h. at 45° C. and was stopped with the addition of 2.0 ml of flashing buffer containing 10 mM sodium phosphate, 0.15 M sodium chloride, 0.05% (w/v) sodium azide, 0.1% (w/v) BSA. The chemiluminescent reaction was initiated with the sequential addition of 300 μl each of Flash Reagent 1 (0.25 N sodium hydroxide, 0.5% (w/v) N,N,N,N-hexadecyltrimethylammonium chloride surfactant) and Flash Reagent 2 (0.5% (w/v) hydrogen peroxide) to 25 μl of the diluted reaction mixture on a Bayer Diagnostics Magic Lite Analyzer equipped with two Corion LL-650 optical filters. Chemiluminescence data were collected as photons detected by the Magic Lite Analyzer and expressed in relative light units (RLUs).

Method of Calculation for Sandwich Assay Parameters.

Arithmetic means for RLUs resulting from a specific analyte concentration, represented here as μ, were calculated from three replicates. Non-tracer assay reagents also contribute a small though sometimes significant number of RLUs. Hence, a control reaction, containing all assay reagents except tracer, was run in parallel to determine non-tracer reagent background, represented here as n. Arithmetic mean RLUs, μ, were corrected to represent RLUs obtained from the tracer only, represented here as B, where B=μ−n. Where the analyte concentration was highest, the corrected arithmetic mean RLU value for that point was denoted as Bmax. A direct but non-linear relationship exists between the analyte concentration present in the standard and the detected RLUs. Consequently, the same direct sigmoidal correlation also relates the analyte concentration to the resultant % B/Bmax and may be accurately expressed in the empirical linear form as $$b = -\log\frac{y_\infty - y}{y - y_0} - m\log x$$

where x is the analyte concentration, and y is the observed signal generated either as % B/Bmax or RLUs (Ref. A, B and C). A. Rodbard, David, *Ligand Analysis*, (1981); and Langon, J., Clapp, J., (Eds.), *Masson Publishing, Inc.*, New York, pp. 45–101; B. Nix, Barry, *The Immunoassay Handbook*, (1994); and Wild, David (Ed.), Stockton Press, Inc., New York, pp. 117–123; and C. Peterman, Jeffrey H., *Immunochemistry of Solid-Phase Immunoassay*; (1991); and Butler, J. (Ed.), *CRC Press, Inc.*, Boca Raton; pp. 47–65.

Additionally, there are four more parameters, namely the regression constant, b, the regression coefficient, m, the assymptotic nonspecific binding (NSB) at zero dose (analyte concentration), $y_\infty$, and the assymptotic infinite limit response for an infinitely high dose, $y_\infty$. The latter three of these parameters were calculated directly using the iterative, weighted, four-parameter logistic (4PL-WTD) analysis function of the DOSECALC.EXE Rev.1.73 program (Bayer Diagnostics Corp., Walpole, Mass.). The arithmetic mean of the regression constant b was determined over the entire range of analyte concentrations as calculated from the dose response expression re-written as $$b = -\log\frac{y_\infty - y}{y - y_0} - m\log x$$

Analyte concentrations of unknowns were subsequently calculated using the dose response equation arranged as $$x = 10^{\frac{\log[(y_\infty - y)/(y - y_0)] + b}{-m}}$$

Figure 14:
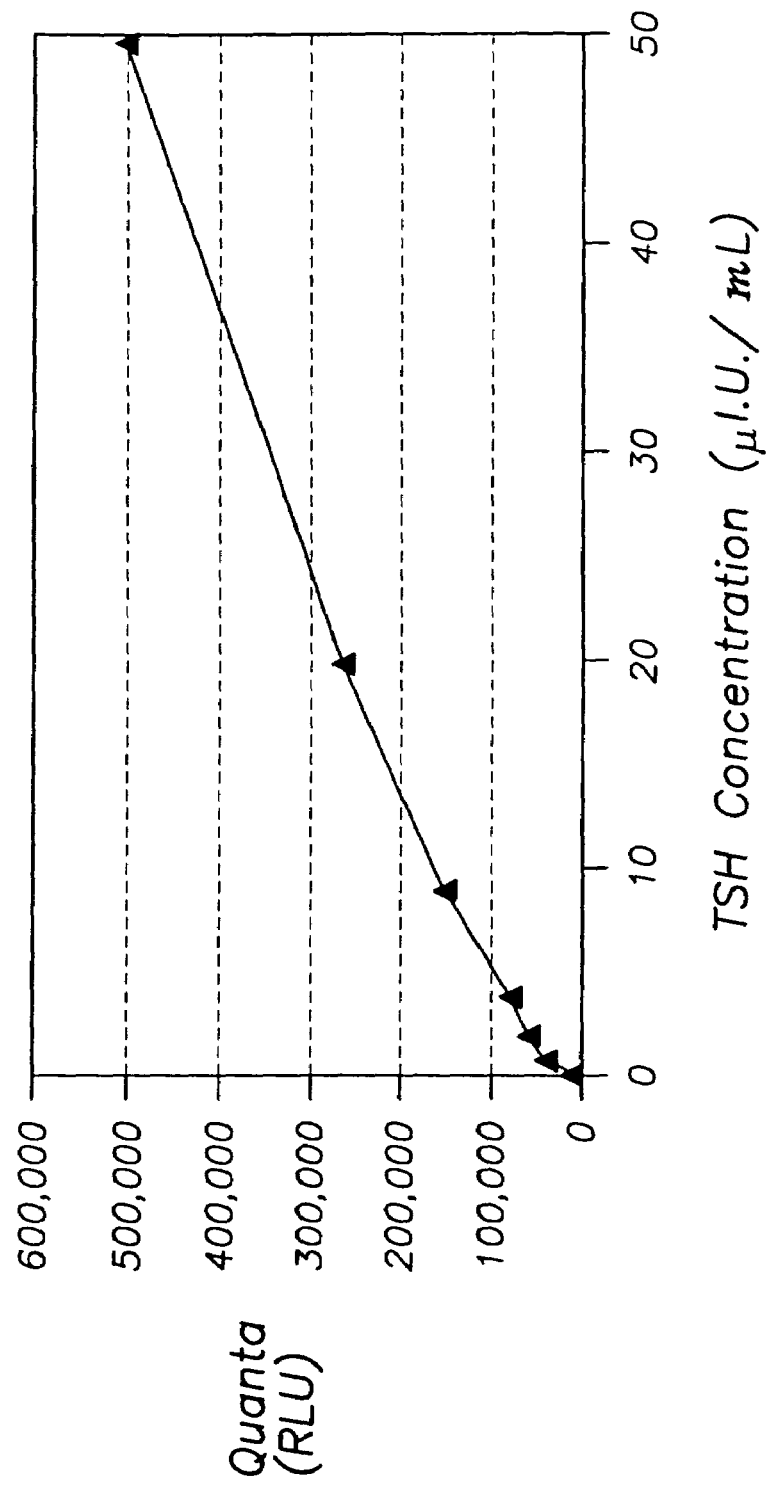
FIG. 14 is a plot of the standard curve of TSH immunoassay using 2-phos-DMAE (1) as the chemiluminescent substrate and alkaline phosphatase as the label.

TSH enzyme-immunoassay standard curve using 2-Phos-DMAE (1) as a chemiluminescent substrate. TSH assay data were plotted as chemiluminescence versus TSH concentration, which is shown in FIG. 14. Dynamic range extended for two orders of magnitude of analyte concentration: satisfactory in this case for the accurate determination of TSH concentration for the three control serum standards.

Assay accuracy in determination of TSH concentration. SH concentrations were calculated for the Bayer Diagnostics Ligands 1, 2 and 3 using the weighted 4PL function. Calculated values closely matched the established values stated in the associated product literature. Therefore, the chemiluminescent substrate, 2-Phos-DMAE, has demonstrable utility for the accurate determination of TSH concentration in human serum.

| Expected vs. Calculated TSH Concentration for TSH Controls | | | |
|---|---|---|---|
| TSH Concentration | Chiron Diagnostics Ligands | | |
| (μI.U./ml) | 1 | 2 | 3 |
| Expected Range* | 0.4–0.6 | 3.1–5.1 | 14.0–23.4 |
| Determined | 0.5 | 3.9 | 16.8 |

*Reported in Abbott IMx TSH kit (MEIA)

What is claimed is:

1. A chemiluminescent substrate of a hydrolytic enzyme, said substrate having the structure

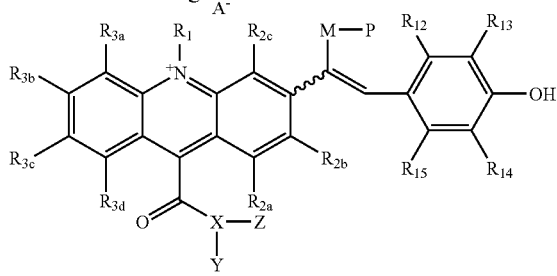

wherein

P is PO₃B wherein B is a divalent cation selected from cations of the group consisting of Ca and Mg, or two monovalent cations selected from the group consisting of Na, H, K M is oxygen;

$R_1$ is an alkyl, alkenyl, alkynyl or aralkyl containing 0 to 20 heteroatoms;

$R_{2a}$, $R_{2b}$, $R_{2c}$, $R_{3a}$, $R_{3b}$, $R_{3c}$ and $R_{3d}$ can be the same or different and are selected from the group consisting of hydrogen, methyl, methoxy, halide and cyano (—CN);

$R_{12}$, $R_{13}$, $R_{14}$ and $R_{15}$ can be the same or different and are selected from the group consisting of hydrogen, —R, substituted or unsubstituted aryl, halides, nitro, sulfonate, sulfate, phosphonate, —CO₂H, —C(O)OR, cyano (—CN), —SCN, —OR, —SR, —SSR, —C(O)R, —C(O)NHR, ethylene glycol and polyethylene glycol, where R is an alkyl group having 1 to 6 carbon atoms;

$A^-$ is a counter ion for the electroneutrality of the quaternary nitrogen of the acridinium compound, said $A^-$ not being present if said $R_1$ substituent contains a strongly ionizable group that can form an anion and pair with the quaternary ammonium cationic moiety; and X is selected from the group consisting of O, N and S, such that, when X is O or S, Y is selected from the group consisting of phenyl, (2'-methyl)phenyl, (2'-methoxy)phenyl, (2',6'-dimethyl)phenyl, (2',6'-dimethoxy)phenyl, (2'-methyl-6'-methoxy)phenyl, (2',6'-dimethyl-4'-benzyloxycarbonyl)phenyl, (2',6'-dimethoxy-4'-benzyloxycarbonyl)phenyl, (4'-methyl)phenyl, (2'-methyl-6'-methoxy-4'-benzyloxycarbonyl)phenyl, (2',6'-dimethyl-4'-carboxyl)phenyl, (2',6'-dimethoxy-4'-carboxyl)phenyl and (2'-methyl-6'-methoxy-4'-carboxyl)phenyl, and Z is omitted, and when X is nitrogen, Z is —SO₂—Y', Y is as defined above, Y' being defined the same as Y above, or Y and Y' can each be a branched or straight-chain alkyl containing 0 to 20 carbons, halogenated or unhalogenated, a substituted aryl or heterocyclic ring system, and Y and Y' can be the same or different.

2. The chemiluminescent substrate of claim 1 wherein any adjacent two groups of $R_{12}$, $R_{13}$, $R_{14}$ and $R_{15}$ can form one or more additional fused hydrocarbon aromatic rings or heteroaromatic rings with or without substitutions, said rings selected from the group consisting of benzene, naphthlene, pyridine, thiophene, furan and pyrrole.

3. The chemiluminescent substrate of claim 1 wherein said counter ion $A^-$ is selected from the group consisting of $CH_3SO_4^-$, $FSO_3^-$, $CF_3SO_3^-$, $C_4F_9SO_3^-$, $CH_3C_6H_4SO_3^-$, halide, $CF_3COO^-$, $CH_3COO^-$, and $NO_3^-$.

4. The chemiluminescent substrate of claim 1 wherein $R_1$ is selected from the group consisting of methyl, carboxymethyl and sulfoalkyl.

5. The chemiluminescent substrate of claim 4 wherein $R_1$ is selected from the group consisting of sulfopropyl and sulfobutyl.

6. The chemiluminescent substrate of claim 1 wherein P is PO₃B.

7. The chemiluminescent substrate of claim 1 wherein $R_{2a}$, $R_{2b}$, $R_{2c}$, $R_{3a}$, $R_{3b}$, $R_{3c}$ and $R_{3d}$ are hydrogen.

8. The chemiluminescent substrate of claim 1 having the structure

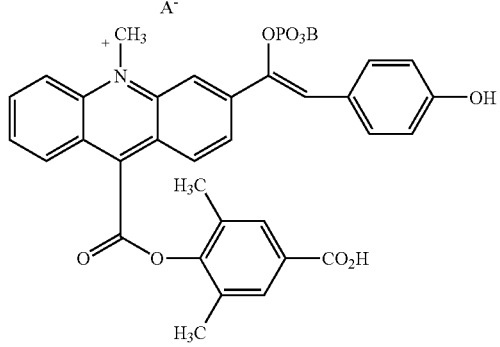

wherein $A^-$ is selected from the group consisting of $CH_3SO_4^-$, $FSO_3^-$, $CF_3SO_3^-$, $C_4F_9SO_3^-$, $CH_3C_6H_4SO_3^-$, halide, $CF_3COO^-$, $CH_3COO^-$ and $NO_3^-$.

9. The chemiluminescent substrate of claim 1 having the structure

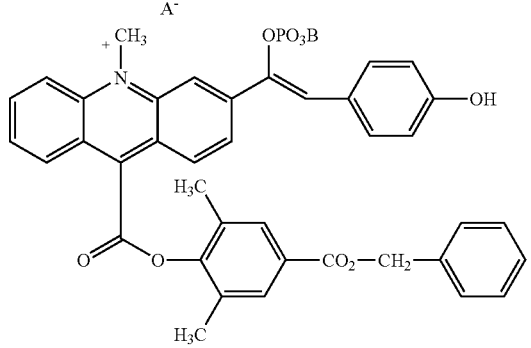

wherein $A^-$ is selected from the group consisting of $CH_3SO_4^-$, $FSO_3^-$, $CF_3SO_3^-$, $C_4F_9SO_3^-$, $CH_3C_6H_4SO_3^-$, halide, $CF_3COO^-$, $CH_3COO^-$ and $NO_3^-$.

10. The chemiluminescent substrate of claim 1 having the structure

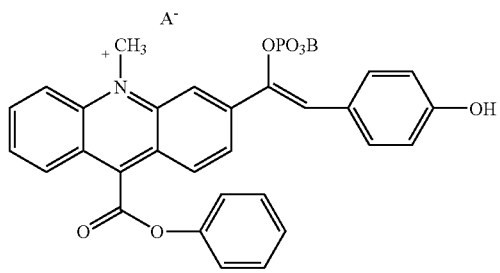

wherein $A^-$ is selected from the group consisting of $CH_3SO_4^-$, $FSO_3^-$, $CF_3SO_3^-$, $C_4F_9SO_3^-$, $CH_3C_6H_4SO_3^-$, halide, $CF_3COO^-$, $CH_3COO^-$ and $NO_3^-$.

11. The chemiluminescent substrate of claim 1 having the structure
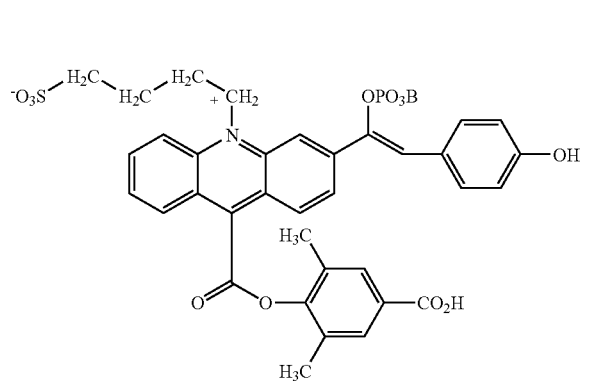
12. The chemiluminescent substrate of claim 1 having the structure
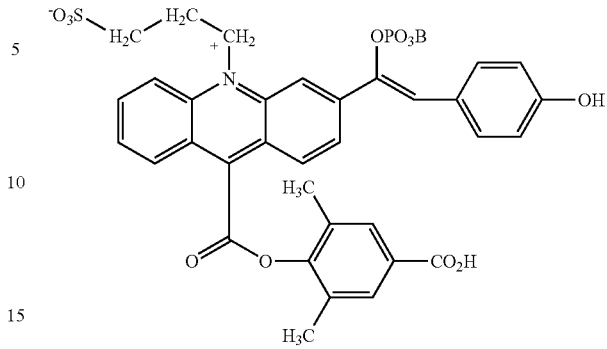
* * * * *